US010730865B2

(12) United States Patent
Evenas et al.

(10) Patent No.: US 10,730,865 B2
(45) Date of Patent: Aug. 4, 2020

(54) COMPOUNDS FOR MODULATING AQUAPORINS

(71) Applicant: APOGLYX AB, Lund (SE)

(72) Inventors: Johan Evenas, Lund (SE); Joakim Larsson, Lund (SE); Klaus Dreisch, Lund (SE)

(73) Assignee: APOGLYX AB, Lund (SE)

( * ) Notice: Subject to any disclaimer, the term of this patent is extended or adjusted under 35 U.S.C. 154(b) by 0 days.

(21) Appl. No.: 16/096,521

(22) PCT Filed: Apr. 28, 2017

(86) PCT No.: PCT/EP2017/060148
§ 371 (c)(1),
(2) Date: Oct. 25, 2018

(87) PCT Pub. No.: WO2017/186893
PCT Pub. Date: Nov. 2, 2017

(65) Prior Publication Data
US 2019/0127360 A1 May 2, 2019

(30) Foreign Application Priority Data
Apr. 28, 2016 (EP) .................. 16167378

(51) Int. Cl.
C07D 417/12 (2006.01)
C07D 403/12 (2006.01)
A61P 19/02 (2006.01)
A61P 3/10 (2006.01)
C07D 417/14 (2006.01)

(52) U.S. Cl.
CPC ............ C07D 417/12 (2013.01); A61P 3/10 (2018.01); A61P 19/02 (2018.01); C07D 403/12 (2013.01); C07D 417/14 (2013.01)

(58) Field of Classification Search
None
See application file for complete search history.

(56) References Cited

FOREIGN PATENT DOCUMENTS

WO 2004/089367 A1 10/2004
WO 2016/066696 A2 5/2016

OTHER PUBLICATIONS

Ito et al., Cancer Science 94(1), 3-8 (2003).*
STN Registry Database entry for CAS RN 333792-18-0; Entered STN May 1, 2001; Accessed Sep. 3, 2019.*
Database Caplus (OnLine), Database Accession No. 2009:846108—CAS Registry No. 717829-21-5, "Method Using Lifespan-Altering Compound for Altering the Lifespan of Eukaryotic Organisms, and Screening for Such Compounds," Inventor: D. Goldfarb, Dec. 22, 2008 (Online).
Extended European Search Report for EP 16167378.5 dated May 30, 2016.
International Search Report of PCT/EP2017/060148 dated Jun. 1, 2017.
Jelen S., et al., "Aquaporin-9 Protein is the Primary Route of Hepatocyte Glycerol Uptake for Glycerol Gluconeogenesis in Mice," J. Biol. Chem., vol. 286, pp. 44319-44325 (Nov. 11, 2011—published online).
Database Caplus (OnLine), Database Accession No. 2013-632163—Wacker, S., et al., "The Identification of Novel, High Affinity AQP9 Inhibitors in an Intracellular Binding Site," Molecular Membrane Biology, vol. 30, No. 3, pp. 246-260 (Mar. 1, 2013—published online) (Abstract).
Wawer M., et al., "Systematic Extraction of Structure-Activity Relationship Information from Biological Screening Data," ChemMedChem, vol. 4, No. 9, pp. 1431-1438 (Jan. 1, 2009).
Written Opinion of PCT/EP2017/060148 dated Jun. 1, 2017.
Written Opinion of PCT/EP2017/060148 dated Jun. 25, 2018.

* cited by examiner

Primary Examiner — Alicia L Otton
(74) Attorney, Agent, or Firm — Polsinelli PC; Ron Galant

(57) ABSTRACT

The invention relates to compounds of formula (I) pharmaceutical compositions thereof and methods for modulating aquaporin 9.

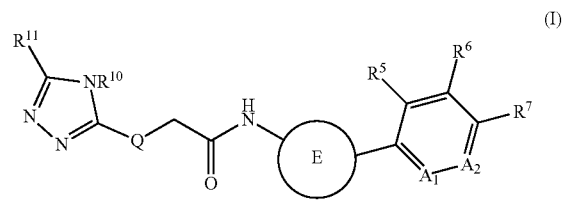

(I)

29 Claims, No Drawings

COMPOUNDS FOR MODULATING AQUAPORINS

FIELD OF THE INVENTION

The present invention relates to compounds for modulating or regulating aquaporins and in particular, Aquaporin 9 (AQP9). The invention also relates to pharmaceutical compositions comprising the compounds disclosed herein and a method of modulating AQP9, such as e.g. with the aim of treating diabetes, in a subject comprising administration of the compounds or pharmaceutical compositions thereof. Thus, present invention also relates to methods of treating a subject in need of a therapy pertaining to modulation of aquaporins and in particular modulation of aquaporin 9 (AQP9).

BACKGROUND

Aquaporins are widely but differentially expressed in plant and animal tissues. These transmembrane channels facilitate passive transport of water and specific solutes, like urea and glycerol, thereby crucially affecting fluid balance in mammalian and other organisms. Members of these channels have been shown to contribute to the pathology of various diseases and disorders, including metabolic disease, inflammatory disease, bone disease, atherosclerosis, allergic diseases, as well as autoimmune pathologies such as rheumatoid arthritis. Mammalian aquaporins can be divided into at least three subfamilies: the aquaporin subfamily that conducts water, the aquaglyceroporins, which allow the passage of water and small uncharged molecules like glycerol and urea, and a third group of unorthodox aquaporins which remain poorly characterized at present.

Aquaporin 3, 7 and 9 belong to the aquaglyceroporins and are structurally related, but expressed in different cells and tissues and thus have been ascribed specific functions. Aquaporin 9 (AQP9) is a glycerol channel that is expressed in liver, lung, and skin tissues, gastrointestinal tissues, tissues of the male and female reproductive tract, and hematopoietic cells (*The Human Protein Atlas*, www.proteinatlas.org). Thus, AQP9 channels might represent good targets for drug development since agents modulating these channels would be useful in the treatment of disorders and diseases, where its function or dysfunction contributes to the development or maintenance of disease. Indeed, AQP9 has been implicated in pathophysiological processes in a variety of diseases, such as diabetes, atherosclerosis, disuse osteoporosis, non-alcoholic fatty liver disease, acute kidney injury, kidney ischemia-reperfusion injury, inflammatory diseases including but not limited to inflammatory bowel disease, psoriasis, allergic contact dermatitis, and rheumatoid arthritis.

Approximately 90% of all plasma glycerol is converted to glucose by the liver. In states of dysregulated glucose metabolism, such as type 2 diabetes (characterized by elevated blood glucose levels and insulin resistance), gluconeogenesis from glycerol accounts for 10% of hepatic glucose production in patients (Puhakainen, I. et. al., *J. Clin. Endocrinol. Metab.*, 1992, 75, 789-794). This amounts to a daily production of 500 mmol (about 90 gram) of glucose in average obese type 2 patients, compared to 150 mmol in healthy individuals of normal weight.

Studies of AQP9 knockout mice have clearly demonstrated the pathophysiological relevance of glycerol channels in liver through effects on glycerol metabolism. Specifically, AQP9 is essential for efficient glycerol uptake into hepatocytes and is crucial for hepatic glucose production. (Jelen et al, *J. Biol. Chem.*, 2011, 286, 44319-44325). In AQP9-deficient diabetic mice, blood glucose levels were normal 2 hours after a meal, while blood glucose was ~30% elevated in equally treated aquaporin 9 wildtype diabetic mice (Rojek, A. M., et al., *Proc. Natl. Acad. Sci. USA*, 2007, 104, 3609-3614). These results suggest that inhibition of AQP9 could reduce plasma glucose levels after a meal and that AQP9 is a potential drug target in diabetic treatment.

It would be desirable to provide compounds having high affinity for aquaporin 9 and the ability to modulate aquaporin 9 or to diminish deregulated hepatocyte glucose output in metabolic disease characterized by hyperglycemia.

SUMMARY

Consequently, the present invention seeks to prevent, mitigate, alleviate, eliminate or circumvent one or more of the above-identified deficiencies in the art and disadvantages singly or in any combination by providing, in one aspect, a compound of Formula (I)

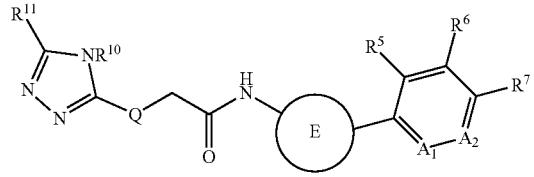

Formula (I)

or pharmaceutically acceptable salts and stereoisomers thereof, wherein

Q is S, —CH$_2$—Or O;

E is a 5-membered heteroaryl or a 6-membered heteroaryl having 1, 2, 3 or 4 heteroatoms independently selected from N, O or S;

A$_1$ and A$_2$ are independently selected from the group consisting of CH, CR$^2$ and N;

R$^2$ is selected from the group consisting of H, F, Cl, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy;

R$^5$ is selected from the group consisting of H, F, Cl, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy;

R$^6$ is selected from the group consisting of H, F, Cl, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy;

R$^7$ is selected from the group consisting of H, halogen, CF$_3$, CN, OH, C$_1$-C$_6$ alkyl, C$_3$-C$_6$ cycloalkyloxy, C$_3$-C$_6$ cycloalkyl, C$_1$-C$_6$ alkyloxy, O(CH$_2$)$_m$O(CH$_2$)$_n$CH$_3$, O(CH$_2$)$_m$ N(R$^{4a}$)(R$^{4b}$), C(O)N(R$^{4a}$)(R$^{4b}$), SR$^{4a}$, S(O)$_2$N(R$^{4a}$)(R$^{4b}$), S(O)$_2$(R$^{4a}$), S(O)$_2$(NR$^{4a}$)(R$^{4b}$), O(CH$_2$)$_n$-heterocycloalkyl, OSO$_2$CH$_3$ and halogenated alkyls or alkoxy m is an integer selected from the group consisting of 1, 2, and 3;

n is an integer selected from the group consisting of 0, 1, and 2;

R$^{4a}$ and R$^{4b}$ are independently selected from H, C$_1$-C$_6$ alkyl, and C$_3$-C$_6$ cycloalkyl;

R$^{10}$ is selected from the group consisting of C$_1$-C$_6$ alkyl, C$_1$-C$_6$ alkylene-aryl, C$_1$-C$_6$ alkylene-OR$^{12a}$, C$_1$-C$_6$ alkylene-N(R$^{12a}$)(R$^{12b}$), C$_1$-C$_6$ alkylene-C(O)(R$^{12a}$)(R$^{12b}$), C$_1$-C$_6$ alkylene-C(O)OR$^{12a}$, C$_1$-C$_3$ alkylene-C$_3$-C$_6$ cycloalkyl, C$_1$-C$_3$ alkylene-C$_3$-C$_6$ heterocycloalkyl, C$_3$-C$_5$ cycloalkyl, aryl or heteroaryl optionally substituted with at least one group selected from the group consisting of halogen, $CF_3$, CN, OH, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^{11}$ is selected from the group consisting of $C_1$-$C_6$ alkyl, $C_1$-$C_6$ alkylene-aryl, $C_3$-$C_6$ cycloalkyl, $C_1$-$C_3$ alkylene-$C_3$-$C_6$ heterocycloalkyl, $C_1$-$C_6$ alkylene-$OR^{12a}$, aryl or heteroaryl optionally substituted with at least one group selected from the group consisting of halogen, $CF_3$, CN, OH, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy, $R^{12a}$ and $R^{12b}$ are independently selected from H, $C_1$-$C_4$ alkyl, and cyclopropyl.

In one aspect Q is S.

In another aspect E is 1,3,4-thiadiazole.

In a further aspect $R^{11}$ is not aryl or heteroaryl.

In one aspect of the invention, with the proviso that when Q is S and E is 1,3,4-thiadiazole, then $R^{11}$ is not aryl or heteroaryl.

The invention also relates to a pharmaceutical composition comprising a compound as described herein and a pharmaceutically acceptable diluent, excipient or carrier. Consequently, the invention relates to a compound of formula (I) for use in medicine. The invention also relates to a compound of Formula (I) for use in the treatment of any disease that is treatable by regulation or modulation of aquaporins, such as e.g. Aquaporin 3, 7 and 9. One particular example is Aquaporin 9.

Furthermore, the invention relates to a compound of Formula (I) for use in the treatment of diabetes, atherosclerosis, disuse osteoporosis, non-alcoholic fatty liver disease, acute kidney injury, kidney ischemia-reperfusion injury, inflammatory diseases including but not limited to inflammatory bowel disease, psoriasis, allergic contact dermatitis, and rheumatoid arthritis.

Consequently, the invention relates to a compound of Formula (I) for use in the treatment of diabetes.

The invention further relates to a compound of Formula (I) for use in the treatment of inflammatory diseases such as e.g. psoriasis and allergic contact dermatitis.

The invention also relates to a compound of Formula (I) for use in the treatment of rheumatoid arthritis.

Present invention also relates to use of a compound according to Formula (I) for the manufacture of a medicament for the treatment and/or prevention of a disease such as e.g. diabetes, atherosclerosis, disuse osteoporosis, non-alcoholic fatty liver disease, acute kidney injury, kidney ischemia-reperfusion injury, inflammatory diseases including but not limited to inflammatory bowel disease, psoriasis, allergic contact dermatitis, and rheumatoid arthritis.

Thus, the invention relates to use of a compound according to Formula (I) for the manufacture of a medicament for the treatment and/or prevention of diabetes.

Moreover, the invention relates to use of a compound according to Formula (I) for the manufacture of a medicament for the treatment and/or prevention of diabetes inflammatory diseases including but not limited psoriasis and allergic contact dermatitis.

Furthermore, the invention relates to a method of treating a subject in need of therapy to regulate or modulate one or more aquaporins, such as e.g. aquaporin 9. The method may relate to administration of a compound or pharmaceutical composition as described herein to a subject in need thereof in order to prevent and/or treat a disease, such as e.g. diabetes, such as e.g. diabetes mellitus type 2 but may also include diabetes mellitus type 1, atherosclerosis, disuse osteoporosis, non-alcoholic fatty liver disease, acute kidney injury, kidney ischemia-reperfusion injury, inflammatory diseases including but not limited to inflammatory bowel disease, psoriasis, allergic contact dermatitis, and rheumatoid arthritis.

Thus, the invention relates to a method of treating diabetes, such as e.g. diabetes mellitus type 2, the method comprising administering a compound according to Formula (I) or a pharmaceutical composition thereof to a subject in need thereof.

Furthermore, the invention relates to a method of treating rheumatoid arthritis, the method comprising administering a compound according to Formula (I) or a pharmaceutical composition thereof to a subject in need thereof.

According to one aspect, the invention relates to a compound or pharmaceutical composition of the herein above described type, or a compound selected from any one of the examples as disclosed herein. Specifically, the invention relates to any one of the compounds as seen in examples 1-49.

Furthermore, the invention relates to any one of compounds as seen in the examples for use in treating diabetes such as e.g. diabetes mellitus type 2.

According to another aspect, the invention also relates to a compound or pharmaceutical composition of the herein above described type, or a compound selected from any one of the examples as disclosed herein, for use in treatment inflammatory diseases, e.g. psoriasis or allergic contact dermatitis.

According to another aspect, present invention relates to a compound or pharmaceutical composition of Formula (I) or a compound as described in structures seen in the examples as disclosed herein, for use in treatment of disorders and diseases, where the function or dysfunction of AQP9 contributes to the development or maintenance of disease, such as diabetes, atherosclerosis, disuse osteoporosis, non-alcoholic fatty liver disease, acute kidney injury, kidney ischemia-reperfusion injury, inflammatory diseases, e.g. inflammatory bowel disease, psoriasis, allergic contact dermatitis or rheumatoid arthritis.

Merely as examples and not with the intention to limit the invention, further advantageous features of the invention are defined in the claims, the detailed description and the examples as seen below.

DETAILED DESCRIPTION OF PREFERRED EMBODIMENTS

Definitions

Unless defined otherwise, all technical and scientific terms used herein have the same meaning as is commonly understood by one of ordinary skill in the art. All patents, applications, published applications and other publications referenced herein are incorporated by reference in their entirety.

As used herein "comprising" is intended to be interpreted by the broader meaning "include", "contain" or "comprehend". Thus the term "comprising" is intended is synonymous with "including," "containing," or "characterized by," and is inclusive or open-ended and does not exclude additional, non-recited elements or method steps. Moreover, in the claims, the term "comprises/comprising" in accordance with the above, does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality.

The terms "a", "an", "first", "second" etc. do not preclude a plurality.

As used herein, "$C_m$ to $C_n$," "$C_m$-$C_n$" or "$C_{m-n}$" in which "m" and "n" are integers refers to the number of carbon atoms in the relevant group. That is, the group can contain from "m" to "n", inclusive, carbon atoms. Thus, for example, a "$C_1$-$C_6$ alkyl" group refers to all alkyl groups having from 1 to 6 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $CH_3CH(CH_3)CH_2$—, $(CH_3)_3C$—, $CH_3(CH_2)_3CH_2$— and $CH_3(CH_2)_4CH_2$—.

As used herein, "alkyl" refers to a straight or branched hydrocarbon chain group that is fully saturated (no double or triple bonds). The alkyl group of the compounds may be designated as "$C_1$-$C_4$ alkyl," "$C_{1-4}$ alkyl" or similar designations. By way of example only, "$C_1$-$C_4$ alkyl" or "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "cycloalkyl" refers to a completely saturated (no double bonds) monocyclic hydrocarbon ring system. Cycloalkyl groups may range from $C_3$ to $C_{10}$, such as from $C_3$ to $C_6$. Typical cycloalkyl groups include, but are in no way limited to, cyclopropyl, cyclobutyl, cyclopentyl, cyclohexyl, and the like.

An "alkylene" is a straight-chained tethering group, forming bonds to connect molecular fragments via their terminal carbon atoms. The alkylene may be a medium size alkylene having 1 to 6 carbon atoms, such as "$C_1$-$C_6$." The alkylene could also be a lower alkylene having 1 to 4 carbon atoms. The alkylene may be designated as "$C_1$-$C_4$ alkylene", "$C_{1-4}$ alkylene" or similar designations. Non-limiting examples include, methylene (—$CH_2$—), ethylene (—$CH_2CH_2$—), propylene (—$CH_2CH_2CH_2$—), and butylene (—$(CH_2)_4$—) groups. In the case of methylene, the two connected fragments are connected to the same carbon atom.

As used herein, "alkyloxy" refers to the group —OR wherein R is an alkyl. Non-limiting examples of alkyloxy groups include methoxy, ethoxy, n-propoxy, 1-methylethoxy (isopropoxy), n-butoxy, iso-butoxy, sec-butoxy, and tert-butoxy. However, the alkyl in the alkyloxy group does not include cycloalkyl groups.

As used herein, "halogen" refers to F (fluoro), Cl (chloro), Br (bromo) or I (iodo).

A "cyano" group refers to a "—CN" group.

A "hydroxy" group or "hydroxyl" group refers to an "—OH" group.

The term "aryl" refers to any aromatic substituent. The aryl may be a single aromatic ring system or may be fused with other aromatic moieties. One example is the phenyl ring. The aryl may further be optionally substituted with any substituent and may furthermore be mono-, di-, tri-, tetra- or penta-substituted. Exemplary substituents may be e.g. any of the above mentioned substituents present on a phenyl ring. Specifically, a phenyl ring which is mono-, di-, tri-, tetra- or penta-substituted, wherein the substituent(s) is/are independently F (fluoro), Cl (chloro), Br (bromo) or I (iodo), OH, OMe, alkoxy, alkyl, cycloalkyl, heterocycloalkyl, CN, $CF_3$, $NH_2$, NHalkyl, carboxyl, carboxyalkyl, carbonyl, carbonylalkyl, sulfoxyl, or sulfonylalkyl As used herein, "heterocycloalkyl" refers to a completely saturated (no double bonds) monocyclic ring system. heterocycloalkyl groups may range from 3 to 10-membered ring system, such as from a 3 to 6 membered ring system. Heterocycloalkyls contain one or more of N, S or O independently. Exemplary heterocycloalkyls as substituents are aziridinyl, epoxidyl, thioepoxidyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl etc.

The term "heteroaryl" refers to a 5- or 6-membered aromatic group having 1 to 4 heteroatoms selected from one or more of nitrogen, sulfur and oxygen. In this specific invention it is apparent that the heteroaryl ring must be able to accommodate at least two binding points. Examples of heteroarylic moieties are e.g. pyrimidine, pyridine, thiazole, oxazole, pyrazole, imidazole, thiadiazole, thiophene, furan, triazole, oxadiazole, tetrazole, pyridazine, triazine and pyrazine in any isomeric form.

The term "stereoisomers" refers to compounds that have the same molecular formula and sequence of bonded atoms but differ in the three-dimensional orientations of their atoms in space. Non-limiting examples of stereoisomers include enantiomers, diastereomers, conformers and atropisomers.

It is understood that, in any compound disclosed herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. Further, compounds provided herein may be in any scalemic mixtures. Likewise, all tautomeric forms are also intended to be included. As used herein, "tautomer" and "tautomeric" refer to alternate forms of a compound disclosed herein that differ in the position of a proton. Non-limiting examples include enol-keto and imine-enamine tautomers, or the tautomeric forms of heteroaryl groups containing a ring atom attached to both a ring —NH— moiety and a ring =N-moiety such as pyrazoles, imidazoles, benzimidazoles, triazoles, and tetrazoles. A further example is the 2-hydroxypyridine/2-pyridone tautomer.

It is also understood that isotopes may be present in the compounds described herein. Each chemical element as represented in a compound structure may include any isotope of said element. For example, in a compound described herein a hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

As used herein, "pharmaceutically acceptable salt" refers to a salt of a compound that does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, piperidine, piperazine, methylpiperazine, N-methyl-D-glucamine, diethylamine, ethylenediamine, tris(hydroxymethyl)methylamine; and salts with the amino group of amino acids such as, without limitation, arginine and lysine. Useful acid-based salts include, without limitation, acetates, adipates, aspartates, ascorbates, benzoates, butyrates, caparate, caproate, caprylate, camsylates, citrates, decanoates, formates, fumarates, gluconates, glutarate, glycolates, hexanoates, laurates, lactates, maleates, nitrates, oleates, oxalates, octanoates, propanoates, palmitates, phosphates, sebacates, succinates, stearates, sulfates, sulfonates, such as methanesulfonates, ethanesulfonates, p-toluenesulfonates, salicylates, tartrates, and tosylates. Further examples of pharmaceutically acceptable salts can be found in "Pharmaceutical Salts: Properties, Selection, and Use", Wermuth, C. G. et al., Wiley publications, 2$^{nd}$ Revised Ed., 2011 which is hereby incorporated in its entirety. Pharmaceutically acceptable solvates and hydrates are complexes of a compound with one or more solvent of water molecules, or 1 to about 100, or 1 to about 10, or one to about 2, 3 or 4, solvent or water molecules.

The term "physiologically acceptable" defines a carrier or diluent that does not abrogate the biological activity and properties of the compound.

As used herein, a "subject" refers to an animal that is the object of treatment, observation or experiment. "Animal" includes cold- and warm-blooded vertebrates and invertebrates such as birds, fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional such as an M.D. or a D.V.M. to attempt to cure, or at least ameliorate the effects of, a particular disease or disorder or to prevent the disease or disorder from occurring in the first place.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "a therapeutically effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

Compounds

As described above, the invention relates to a compound of Formula (I)

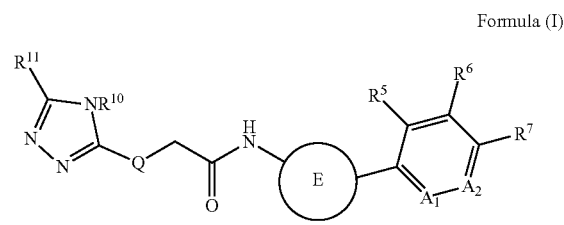

Formula (I)

or pharmaceutically acceptable salts and stereoisomers thereof, wherein

Q is S, —CH$_2$— or O;

E is a 5-membered heteroaryl or a 6-membered heteroaryl having 1, 2, 3 or 4 heteroatoms independently selected from N, O or S;

A$_1$ and A$_2$ are independently selected from the group consisting of CH, CR$^2$ and N;

R$^2$ is selected from the group consisting of H, F, Cl, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy;

R$^5$ is selected from the group consisting of H, F, Cl, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy;

R$^6$ is selected from the group consisting of H, F, Cl, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy;

R$^7$ is selected from the group consisting of H, halogen, CF$_3$, CN, OH, C$_1$-C$_6$ alkyl, C$_3$-C$_6$ cycloalkyloxy, C$_3$-C$_6$ cycloalkyl, C$_1$-C$_6$ alkyloxy, O(CH$_2$)$_m$O(CH$_2$)$_n$CH$_3$, O(CH$_2$)$_m$ N(R$^{4a}$)(R$^{4b}$), C(O)N(R$^{4a}$)(R$^{4b}$), SR$^{4a}$, S(O)$_2$N(R$^{4a}$)(R$^{4b}$), S(O)$_2$(R$^{4a}$), S(O)(NR$^{4a}$)(R$^{4b}$), O(CH$_2$)$_n$-heterocycloalkyl, OSO$_2$CH$_3$ and halogenated alkyls or alkoxy;

m is an integer selected from the group consisting of 1, 2, and 3;

n is an integer selected from the group consisting of 0, 1, and 2;

R$^{4a}$ and R$^{4b}$ are independently selected from H, C$_1$-C$_6$ alkyl, and C$_3$-C$_6$ cycloalkyl;

R$^{10}$ is selected from the group consisting of C$_1$-C$_6$ alkyl, C$_1$-C$_6$ alkylene-aryl, C$_1$-C$_6$ alkylene-OR$^{12a}$, C$_1$-C$_6$ alkylene-N(R$^{12a}$)(R$^{12b}$), C$_1$-C$_6$ alkylene-C(O)N(R$^{12a}$)(R$^{12b}$), C$_1$-C$_6$ alkylene-C(O)OR$^{12a}$, C$_1$-C$_3$ alkylene-C$_3$-C$_6$ cycloalkyl, C$_1$-C$_3$ alkylene-C$_3$-C$_6$ heterocycloalkyl, C$_3$-C$_5$ cycloalkyl, aryl or heteroaryl optionally substituted with at least one group selected from the group consisting of halogen, CF$_3$, CN, OH, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy;

R$^{11}$ is selected from the group consisting of C$_1$-C$_6$ alkyl, C$_1$-C$_6$ alkylene-aryl, C$_3$-C$_6$ cycloalkyl, C$_1$-C$_3$ alkylene-C$_3$-C$_6$ heterocycloalkyl, C$_1$-C$_6$ alkylene-OR$^{2a}$, aryl or heteroaryl optionally substituted with at least one group selected from the group consisting of halogen, CF$_3$, CN, OH, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy, R$^{12a}$ and R$^{12b}$ are independently selected from H, C$_1$-C$_4$ alkyl, and cyclopropyl, or pharmaceutically acceptable salts and stereoisomers thereof.

In one aspect of the invention, with the proviso that when Q is S and E is 1,3,4-thiadiazole, then $R^{11}$ is not aryl or heteroaryl.

In one aspect of the invention Q is S or O.

In one embodiment of the invention E is selected from

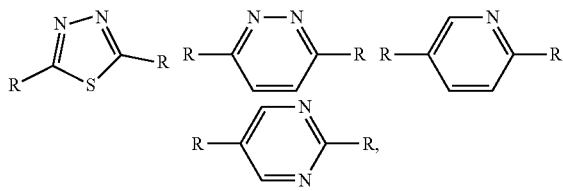

wherein R denotes the attachment points to the rest of the molecule.

In another aspect of the invention, $R^5$ is selected from the group consisting of H, F, Cl and methyl.

In a further aspect of the invention $R^6$ is selected from the group consisting of H, F, Cl and methyl.

In one aspect of the invention $R^7$ is $SO_2Me$, OMe, $(CH_2)_2OMe$, OH, 2-pyridyl, 3-pyridyl, $SO_2$cyclopropyl, Cl, CN, $CF_3$, i-Pr, $(CH_2)$-2-tetrahydrofuranyl, SO(NMe)Me.

In one aspect of the invention $R^6$ and $R^7$ are bridged to form a 5- or 6-membered ring comprising one or two heteroatoms selected from O, S or N.

In one aspect of the invention, $R^5=R^6=R^7=H$.

In one aspect of the invention, $R^5$ and/or $R^6=H$ or F.

In one aspect $R^7$ is $-O-CH_2-CH_2-F$ or $-S-Me$.

In one aspect $R^6$ and $R^7$ are bridged to form a 5-membered ring according to $-CH_2-CH_2-O-$.

In one aspect $R^5=H$, $A^1=A^2=C$, and $R^6$ and $R^7$ are bridged to form a 5-membered ring according to $-CH_2-CH_2-O-$, i.e. to form a 2,3-hihydro-1-benzofuran moiety.

In one aspect $R^6$ and $R^7$ are bridged to form a 6-membered ring according to $-O-CH_2-CH_2-O-$.

In one aspect $R^5=H$, $A^1=A^2=C$, and $R^6$ and $R^7$ are bridged to form a 6-membered ring according to $-O-CH_2-CH_2-O-$, i.e. to form a 1,4-benzodioxane moiety.

In one aspect of the invention, $R^{10}$ is methyl, cyclopropyl, phenyl, 4-fluorophenyl, isopropyl, $(CH_2)_2OH$, $CH_2)_2OMe$, $(CH_2)_3OH$, ethyl, $(CH_2)_2CONH_2$, 3-chlorophenyl.

In another aspect of the invention, $R^{11}$ is Me, Et and cyclopropyl, benzyl, cyclopentyl, N-morpholinyl, $(CH_2)_2$OMe, In one aspect of the invention E is selected from 1,3,4-thiadiazole connected at its 2 and 5 position or pyridazine connected at its 2 and 4 position.

In one aspect of the invention the compounds is any one of compounds (a) to (ap) as disclosed herein.

In some aspects, the invention does not relate to the compounds as seen in table below:

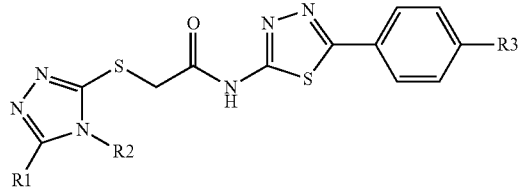

| CAS nr | R1 | R2 | R3 | Chemical name |
|---|---|---|---|---|
| 1071414-35-1 | Et— | [(tetrahydro-2-furanyl)methyl]- | MeO— | Acetamide, 2-[[5-ethyl-4-[(tetrahydro-2-furanyl)methyl]-4H-1,2,4-triazol-3-yl]thio]-N-[5-(4-methoxyphenyl)-1,3,4-thiadiazol-2-yl]- |
| 1071410-62-2 | cPentyl- | Me— | MeO— | Acetamide, 2-[(5-cyclopentyl-4-methyl-4H-1,2,4-triazol-3-yl)thio]-N-[5-(4-methoxyphenyl)-1,3,4-thiadiazol-2-yl]- |
| 1071395-90-8 | Me— | 4-Me—Ph— | MeO— | Acetamide, N-[5-(4-methoxyphenyl)-1,3,4-thiadiazol-2-yl]-2-[[5-methyl-4-(4-methylphenyl)-4H-1,2,4-triazol-3-yl]thio]- |
| 1071363-27-3 | 4-Cl-benzyl- | Et— | MeO— | Acetamide, 2-[[5-[(4-chlorophenyl)methyl]-4-ethyl-4H-1,2,4-triazol-3-yl]thio]-N-[5-(4-methoxyphenyl)-1,3,4-thiadiazol-2-yl]- |
| 1071305-75-3 | cPr— | nPr— | MeO— | Acetamide, 2-[(5-cyclopropyl-4-propyl-4H-1,2,4-triazol-3-yl)thio]-N-[5-(4-methoxyphenyl)-1,3,4-thiadiazol-2-yl]- |
| 1320537-95-8 | Me— | 2,5-(CH3)2-Ph— | H— | Acetamide, 2-[[4-(2,5-dimethylphenyl)-5-methyl-4H-1,2,4-triazol-3-yl]thio]-N-(5-phenyl-1,3,4-thiadiazol-2-yl)- |
| 1316988-49-4 | Me— | Benzyl- | H— | Acetamide, 2-[[5-methyl-4-(phenylmethyl)-4H-1,2,4-triazol-3-yl]thio]-N-(5-phenyl-1,3,4-thiadiazol-2-yl)- |
| 1316925-34-4 | Me— | 4-MeO-phenyl- | H— | Acetamide, 2-[[4-(4-methoxyphenyl)-5-methyl-4H-1,2,4-triazol-3-yl]thio]-N-(5-phenyl-1,3,4-thiadiazol-2-yl)- |
| 1071410-72-4 | cPentyl- | Me— | H— | Acetamide, 2-[(5-cyclopentyl-4-methyl-4H-1,2,4-triazol-3-yl)thio]-N-(5-phenyl-1,3,4-thiadiazol-2-yl)- |
| 1071409-96-5 | 4-Cl-benzyl- | Et— | H— | Acetamide, 2-[[5-[(4-chlorophenyl)methyl]-4-ethyl-4H-1,2,4-triazol-3-yl]thio]-N-(5-phenyl-1,3,4-thiadiazol-2-yl)- |
| 1071366-12-5 | cPr— | Et— | H— | Acetamide, 2-[(5-cyclopropyl-4-ethyl-4H-1,2,4-triazol-3-yl)thio]-N-(5-phenyl-1,3,4-thiadiazol-2-yl)- |
| 1071347-23-3 | cPr— | nPr— | H— | Acetamide, 2-[(5-cyclopropyl-4-propyl-4H-1,2,4-triazol-3-yl)thio]-N-(5-phenyl-1,3,4-thiadiazol-2-yl)- |
| 1071342-66-9 | 2-cyclohexylethyl- | Me— | H— | Acetamide, 2-[[5-(2-cyclohexylethyl)-4-methyl-4H-1,2,4-triazol-3-yl]thio]-N-(5-phenyl-1,3,4-thiadiazol-2-yl)- |

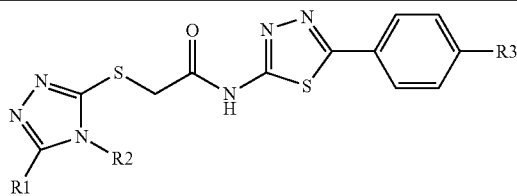

| CAS nr | R1 | R2 | R3 | Chemical name |
| --- | --- | --- | --- | --- |
| 1071332-60-9 | Et— | [(tetrahydro-2-furanyl)methyl]- | H— | Acetamide, 2-[[5-ethyl-4-[(tetrahydro-2-furanyl)methyl]-4H-1,2,4-triazol-3-yl]thio]-N-(5-phenyl-1,3,4-thiadiazol-2-yl)- |
| 948106-83-0 | 4-morpholinylmethyl- | Et— | H— | Acetamide, 2-[[4-ethyl-5-(4-morpholinylmethyl)-4H-1,2,4-triazol-3-yl]thio]-N-(5-phenyl-1,3,4-thiadiazol-2-yl)- |
| 936820-49-4 | Benzyl- | Me— | H— | Acetamide, 2-[[4-methyl-5-(phenylmethyl)-4H-1,2,4-triazol-3-yl]thio]-N-(5-phenyl-1,3,4-thiadiazol-2-yl)- |
| 876718-60-4 | 4-morpholinylmethyl- | Me— | H— | Acetamide, 2-[[4-methyl-5-(4-morpholinylmethyl)-4H-1,2,4-triazol-3-yl]thio]-N-(5-phenyl-1,3,4-thiadiazol-2-yl)- |
| 838593-99-0 | 4-morpholinylmethyl- | Ph— | H— | Acetamide, 2-[[5-(4-morpholinylmethyl)-4-phenyl-4H-1,2,4-triazol-3-yl]thio]-N-(5-phenyl-1,3,4-thiadiazol-2-yl)- |
| 717829-21-5 | Benzyl- | Et— | H— | Acetamide, 2-[[4-ethyl-5-(phenylmethyl)-4H-1,2,4-triazol-3-yl]thio]-N-(5-phenyl-1,3,4-thiadiazol-2-yl)- |

Moreover, the invention does not relate to one or more of the following:
2-[4-Ethyl-5-(2-methoxy-phenyl)-4H-[1,2,4]triazol-3-ylsulfanyl]-N-(4-phenyl-thiazol-2-yl)-acetamide;
2-[5-(2-bromo-phenyl)-4-methyl-4H-[1,2,4]triazol-3-ylsulfanyl]-N-(4-phenyl-thiazol-2-yl)-acetamide;
[4-Ethyl-5-(4-hydroxy-phenyl)-4H-[1,2,4]triazol-3-ylsulfanyl]-acetic acid cyclohexyl ester;
2-[5-(2-Methoxy-phenyl)-4-methyl-4H-[1,2,4]triazol-3-ylsulfanyl]-N-(4-phenyl-thiazol-2-yl)-acetamide.

In a further aspect of the invention, with the proviso that when Q is S and E is 1,3,4-thiadiazole, then $A_1=A_2$ is not CH and simultaneously $R^5=R^6$ is not H and $R^7$ is not H or OMe.

In one aspect, the invention relates to one or more of the compounds according to the examples disclosed herein. Specifically, the invention relates to:
2-[(5-ethyl-4-phenyl-4H-1,2,4-triazol-3-yl)sulfanyl]-N-[5-(4-methoxyphenyl)-1,3,4-thiadiazol-2-yl]acetamide;
2-[(diethyl-4H-1,2,4-triazol-3-yl)sulfanyl]-N-[5-(4-methoxyphenyl)-1,3,4-thiadiazol-2-yl]acetamide;
2-[(5-benzyl-4-ethyl-4H-1,2,4-triazol-3-yl)sulfanyl]-N-[5-(4-methoxyphenyl)-1,3,4-thiadiazol-2-yl]acetamide;
2-{[4-ethyl-5-(4-fluorophenyl)-4H-1,2,4-triazol-3-yl]oxy}-N-[5-(4-methoxyphenyl)-1,3,4-thiadiazol-2-yl]acetamide;
2-[(4-ethyl-5-methyl-4H-1,2,4-triazol-3-yl)sulfanyl]-N-[5-(4-methanesulfonylphenyl)-1,3,4-thiadiazol-2-yl]acetamide;
2-{[4-ethyl-5-(propan-2-yl)-4H-1,2,4-triazol-3-yl]sulfanyl}-N-[5-(4-methanesulfonylphenyl)-1,3,4-thiadiazol-2-yl]acetamide;
2-[(5-cyclopropyl-4-ethyl-4H-1,2,4-triazol-3-yl)sulfanyl]-N-[5-(4-methanesulfonylphenyl)-1,3,4-thiadiazol-2-yl]acetamide;
2-[(diethyl-4H-1,2,4-triazol-3-yl)sulfanyl]-N-[5-(4-methanesulfonylphenyl)-1,3,4-thiadiazol-2-yl]acetamide;
2-{[4-ethyl-5-(4-fluorophenyl)-4H-1,2,4-triazol-3-yl]sulfanyl}-N-[6-(4-methoxyphenyl)pyridazin-3-yl]acetamide;
2-[(5-ethyl-4-methyl-4H-1,2,4-triazol-3-yl)sulfanyl]-N-[5-(4-methoxyphenyl)-1,3,4-thiadiazol-2-yl]acetamide;
N-[5-(4-methoxyphenyl)-1,3,4-thiadiazol-2-yl]-2-[(5-methyl-4-phenyl-4H-1,2,4-triazol-3-yl)sulfanyl]acetamide;
2-[(diethyl-4H-1,2,4-triazol-3-yl)sulfanyl]-N-{5-[4-(methylsulfanyl)phenyl])-1,3,4-thiadiazol-2-yl}acetamide;
2-[(diethyl-4H-1,2,4-triazol-3-yl)sulfanyl]-N-{5-[4-(2-methylpropoxy)phenyl]-1,3,4-thiadiazol-2-yl}acetamide;
2-[(diethyl-4H-1,2,4-triazol-3-yl)sulfanyl]-N-[5-(4-ethylphenyl)-1,3,4-thiadiazol-2-yl]acetamide;
2-[(diethyl-4H-1,2,4-triazol-3-yl)sulfanyl]-N-[5-(4-propylphenyl)-1,3,4-thiadiazol-2-yl]acetamide;
2-[(diethyl-4H-1,2,4-triazol-3-yl)sulfanyl]-N-[5-(4-butylphenyl)-1,3,4-thiadiazol-2-yl]acetamide;
2-[(diethyl-4H-1,2,4-triazol-3-yl)sulfanyl]-N-(5-phenyl-1,3,4-thiadiazol-2-yl)acetamide;
2-[(diethyl-4H-1,2,4-triazol-3-yl)sulfanyl]-N-[5-(2,3-dihydro-1-benzofuran-5-yl)-1,3,4-thiadiazol-2-yl]acetamide;
2-[(diethyl-4H-1,2,4-triazol-3-yl)sulfanyl]-N-{5-[4-(2-methylpropyl)phenyl]-1,3,4-thiadiazol-2-yl}acetamide;
2-[(diethyl-4H-1,2,4-triazol-3-yl)sulfanyl]-N-{5-[4-(propan-2-yl)phenyl]-1,3,4-thiadiazol-2-yl}acetamide;
2-[(diethyl-4H-1,2,4-triazol-3-yl)sulfanyl]-N-[5-(4-hydroxyphenyl)-1,3,4-thiadiazol-2-yl]acetamide;
2-{[4-ethyl-5-(2-methoxyethyl)-4H-1,2,4-triazol-3-yl]sulfanyl}-N-(5-phenyl-1,3,4-thiadiazol-2-yl)acetamide;
2-{[4-ethyl-5-(2-methoxyethyl)-4H-1,2,4-triazol-3-yl]sulfanyl}-N-{5-[4-(propan-2-yloxy)phenyl]-1,3,4-thiadiazol-2-yl}acetamide;
2-{[4-ethyl-5-(2-methoxyethyl)-4H-1,2,4-triazol-3-yl]sulfanyl}-N-[5-(4-propylphenyl)-1,3,4-thiadiazol-2-yl]acetamide;
2-[(diethyl-4H-1,2,4-triazol-3-yl)sulfanyl]-N-[5-(4-ethoxyphenyl)-1,3,4-thiadiazol-2-yl]acetamide;
2-[(diethyl-4H-1,2,4-triazol-3-yl)sulfanyl]-N-{5-[4-(2-fluoroethoxy)phenyl]-1,3,4-thiadiazol-2-yl}acetamide;
N-[5-(4-ethoxyphenyl)-1,3,4-thiadiazol-2-yl]-2-{[4-ethyl-5-(propan-2-yl)-4H-1,2,4-triazol-3-yl]sulfanyl}acetamide;
2-{[4-ethyl-5-(propan-2-yl)-4H-1,2,4-triazol-3-yl]sulfanyl}-N-{5-[4-(2-fluoroethoxy)phenyl]-1,3,4-thiadiazol-2-yl}acetamide;

2-{[4-ethyl-5-(propan-2-yl)-4H-1,2,4-triazol-3-yl]sulfanyl}-N-{5-[4-(propan-2-yloxy)phenyl]-1,3,4-thiadiazol-2-yl}acetamide;
2-[(diethyl-4H-1,2,4-triazol-3-yl)sulfanyl]-N-{5-[4-(2-methoxyethoxy)phenyl]-1,3,4-thiadiazol-2-yl}acetamide;
2-{[4-ethyl-5-(propan-2-yl)-4H-1,2,4-triazol-3-yl]sulfanyl}-N-{5-[4-(2-methoxyethoxy) phenyl]-1,3,4-thiadiazol-2-yl}acetamide;
N-[5-(4-cyanophenyl)-1,3,4-thiadiazol-2-yl]-2-[(4,5-diethyl-4H-1,2,4-triazol-3-yl)sulfanyl]acetamide;
2-[(4,5-diethyl-4H-1,2,4-triazol-3-yl)sulfanyl]-N-[5-(4-(trifluoromethyl)phenyl)-1,3,4-thiadiazol-2-yl]acetamide;
2-[(4,5-diethyl-4H-1,2,4-triazol-3-yl)sulfanyl]-N-[5-(4-isopropoxyphenyl)-1,3,4-thiadiazol-2-yl]acetamide;
N-[5-(4-chlorophenyl)-1,3,4-thiadiazol-2-yl]-2-[(4,5-diethyl-4H-1,2,4-triazol-3-yl)sulfanyl]acetamide;
2-[(4-cyclopropyl-5-ethyl-4H-1,2,4-triazol-3-yl)sulfanyl]-N-[5-(4-methoxyphenyl)-1,3,4-thiadiazol-2-yl]acetamide;
2-[(4-ethyl-5-(3-fluorobenzyl)-4H-1,2,4-triazol-3-yl)sulfanyl]-N-[5-(4-methoxyphenyl)-1,3,4-thiadiazol-2-yl]acetamide;
2-[(5-cyclopropyl-4-ethyl-4H-1,2,4-triazol-3-yl)sulfanyl]-N-[5-(4-hydroxyphenyl)-1,3,4-thiadiazol-2-yl]acetamide;
2-[(4-cyclopropyl-5-ethyl-4H-1,2,4-triazol-3-yl)sulfanyl]-N-[5-(4-(methylsulfonyl)phenyl)-1,3,4-thiadiazol-2-yl]acetamide;
2-[(5-ethyl-4-(3-hydroxypropyl)-4H-1,2,4-triazol-3-yl)sulfanyl]-N-[5-(4-methoxyphenyl)-1,3,4-thiadiazol-2-yl]acetamide;
2-[(5-ethyl-4-methyl-4H-1,2,4-triazol-3-yl)sulfanyl]-N-[5-(4-(methylsulfonyl)phenyl)-1,3,4-thiadiazol-2-yl]acetamide;
2-[(5-ethyl-4-isopropyl-4H-1,2,4-triazol-3-yl)sulfanyl]-N-[5-(4-(methylsulfonyl)phenyl)-1,3,4-thiadiazol-2-yl]acetamide;
2-[(5-cyclopropyl-4-ethyl-4H-1,2,4-triazol-3-yl)sulfanyl]-N-[5-(4-(2-methoxyethoxy)phenyl)-1,3,4-thiadiazol-2-yl]acetamide;
2-[(4-ethyl-5-(2-methoxyethyl)-4H-1,2,4-triazol-3-yl)sulfanyl]-N-[5-(4-methoxyphenyl)-1,3,4-thiadiazol-2-yl]acetamide;
(2-[(5-cyclopentyl-4-ethyl-4H-1,2,4-triazol-3-yl)sulfanyl]-N-[5-(4-methanesulfonylphenyl)-1,3,4-thiadiazol-2-yl] acetamide);
2-[(5-ethyl-4-(2-methoxyethyl)-4H-1,2,4-triazol-3-yl)sulfanyl]-N-[5-(4-methoxyphenyl)-1,3,4-thiadiazol-2-yl]acetamide;
2-{[5-ethyl-4-(3-methoxypropyl)-4H-1,2,4-triazol-3-yl]sulfanyl}-N-[5-(4-methoxyphenyl)-1,3,4-thiadiazol-2-yl]acetamide;
2-{[4-ethyl-5-(morpholin-4-ylmethyl)-4H-1,2,4-triazol-3-yl]sulfanyl}-N-[5-(4-methoxyphenyl)-1,3,4-thiadiazol-2-yl]acetamide;
2-[(4,5-diethyl-4H-1,2,4-triazol-3-yl)sulfanyl]-N-[5-(pyridin-2-yl)-1,3,4-thiadiazol-2-yl]acetamide.

Synthesis

In the below schemes, illustrations of the synthesis of the compounds of the invention are outlined.

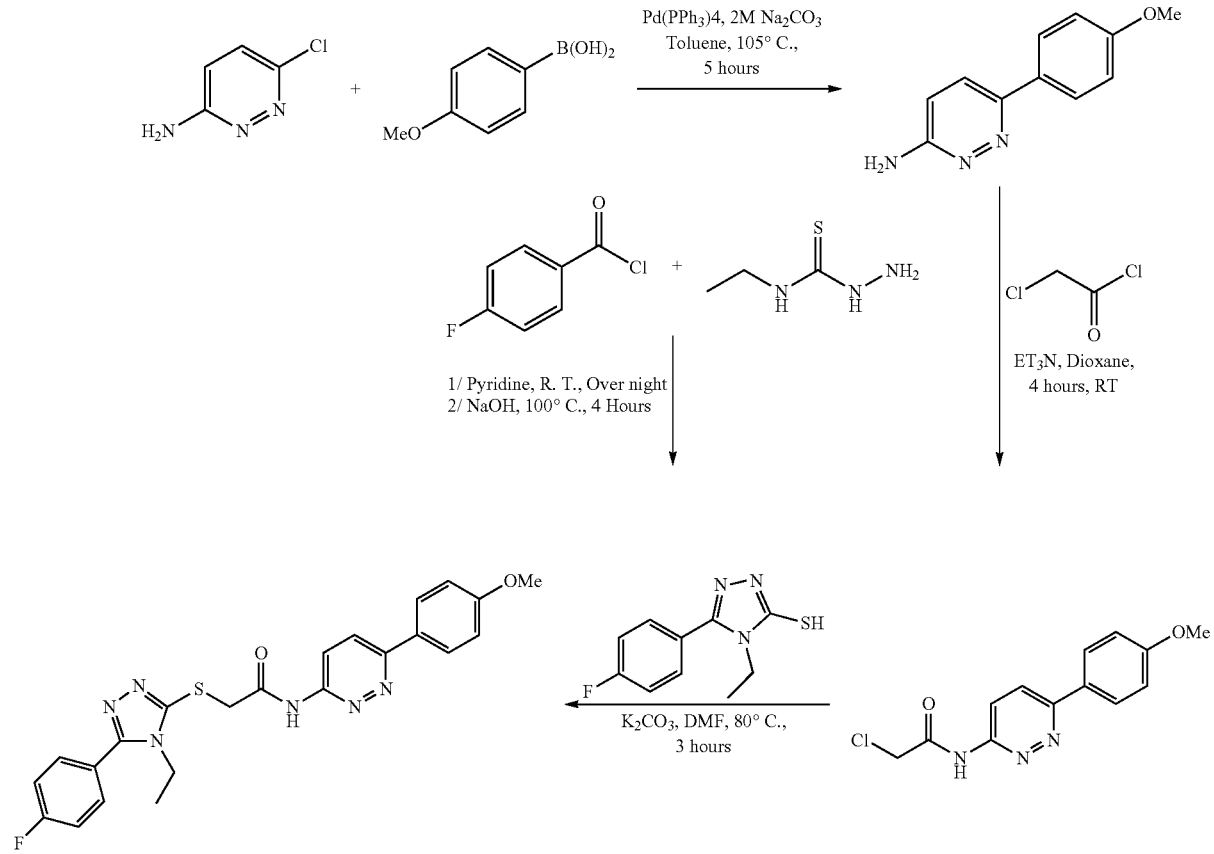

Scheme 1

Scheme 2
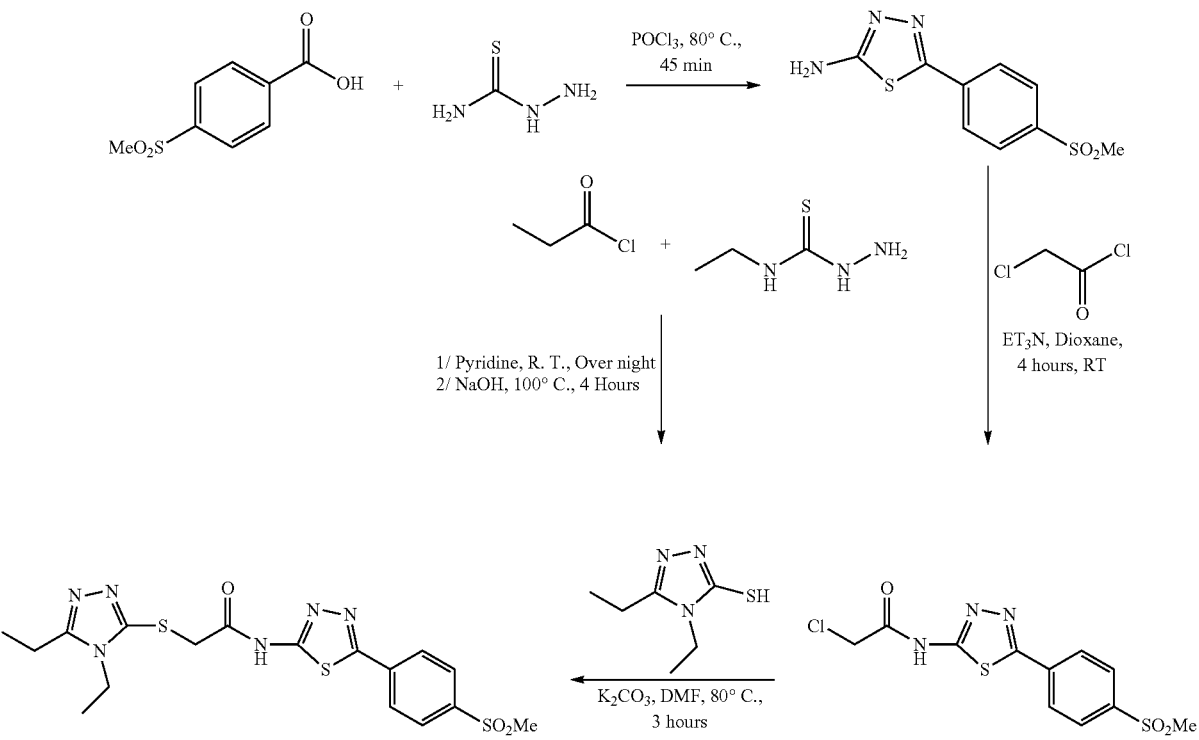
Scheme 3
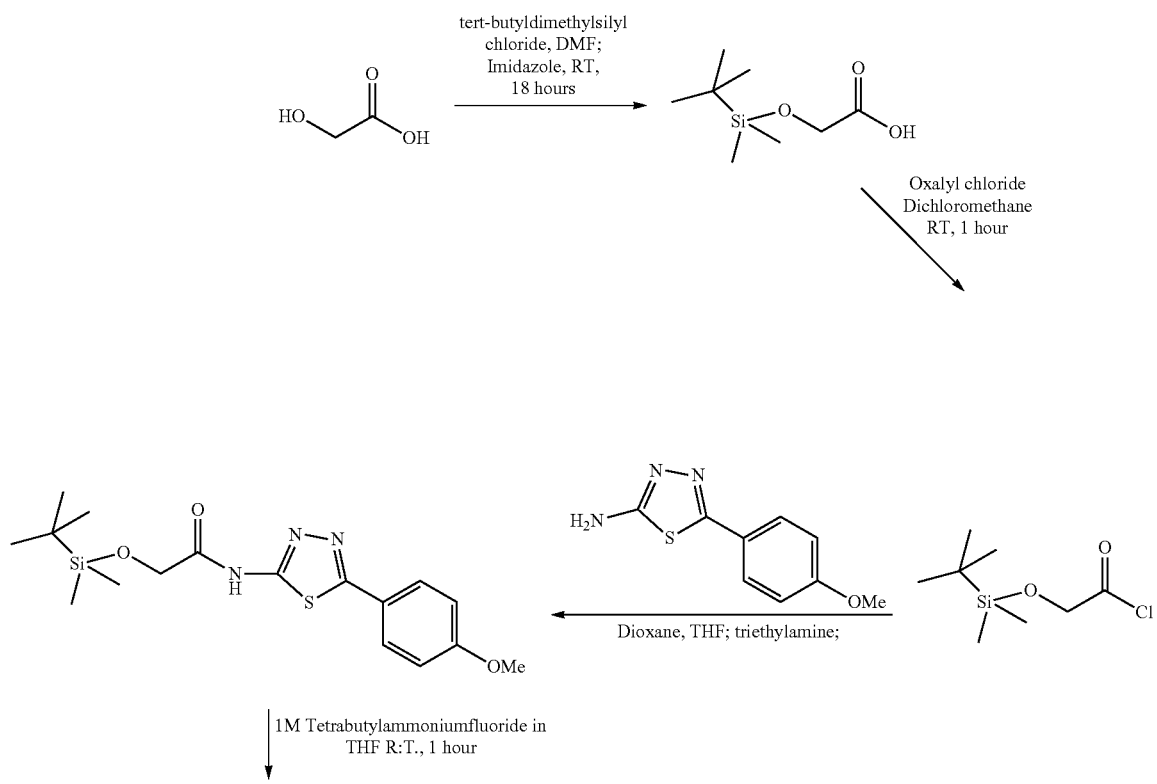

-continued

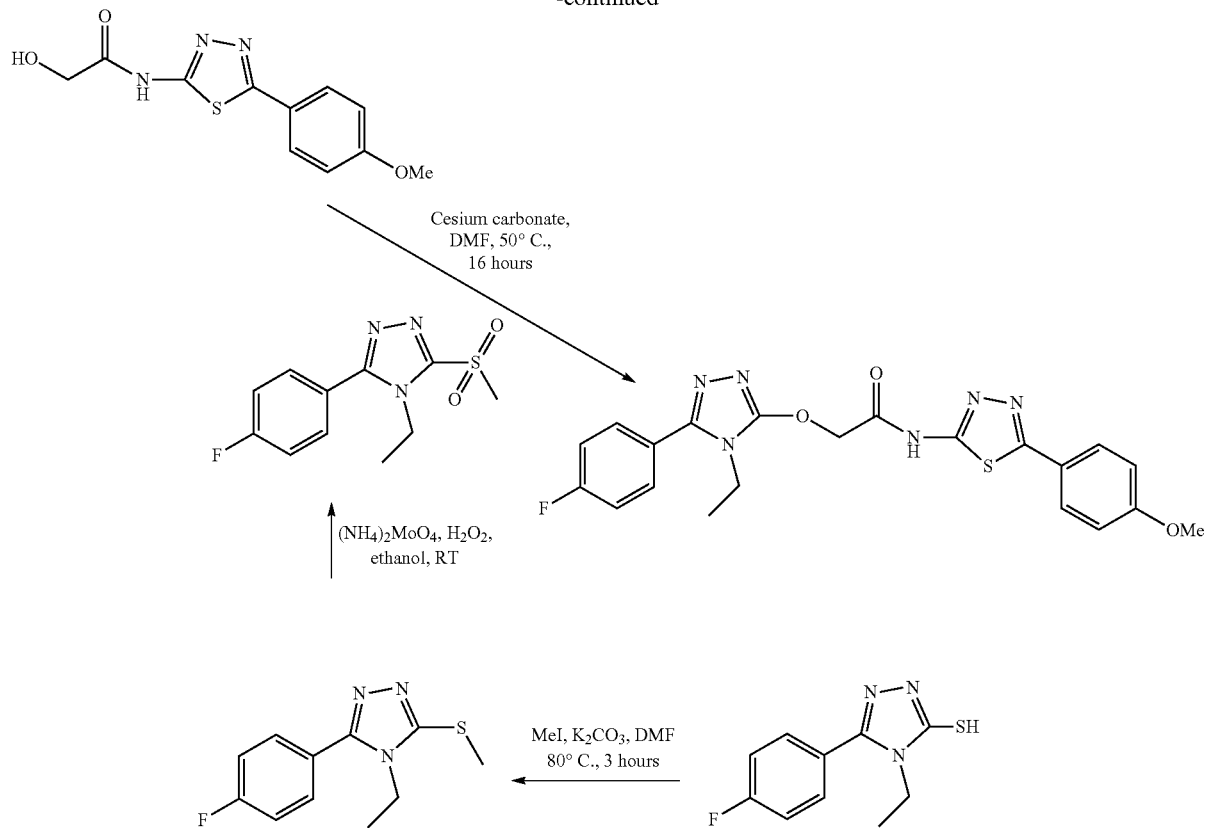

Compounds of Formula (I) wherein $R^7$ is $S(O)(NR^{4a})(R^{4b})$ and wherein $R^{4a}$ is selected from H, $C_1$-$C_6$ alkyl, and $C_3$-$C_6$ cycloalkyl; and $R^{4b}$ is $C_1$-$C_6$ alkyl or $C_3$-$C_6$ cycloalkyl may be prepared as set out in Scheme 4 below.

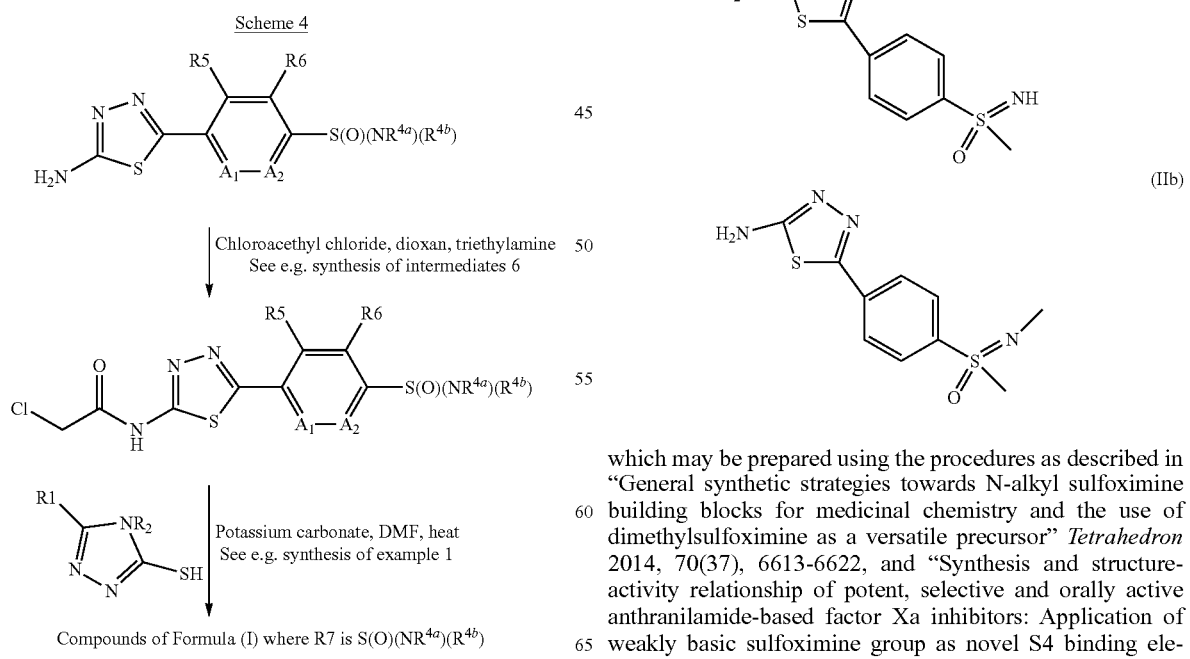

Examples of intermediates of Formula (II) include (IIa-b):

which may be prepared using the procedures as described in "General synthetic strategies towards N-alkyl sulfoximine building blocks for medicinal chemistry and the use of dimethylsulfoximine as a versatile precursor" *Tetrahedron* 2014, 70(37), 6613-6622, and "Synthesis and structure-activity relationship of potent, selective and orally active anthranilamide-based factor Xa inhibitors: Application of weakly basic sulfoximine group as novel S4 binding element" *European Journal of Medicinal Chemistry* 2012, 58, 136-152. A summary is depicted in the scheme below:

Scheme 5

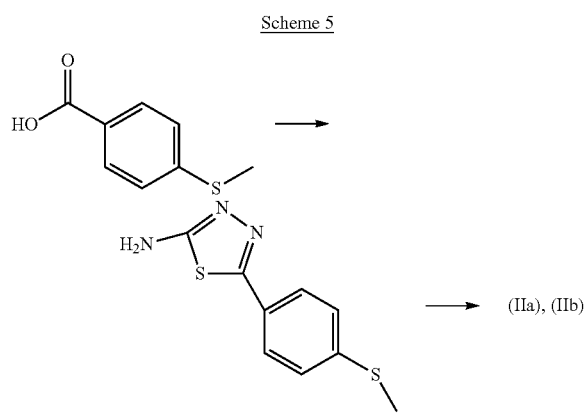

Example of a compound of Formula (I) wherein $R^7$ is $S(O)(NR^{4a})(R^{4b})$ that can be made using the procedure in Scheme 4 is:

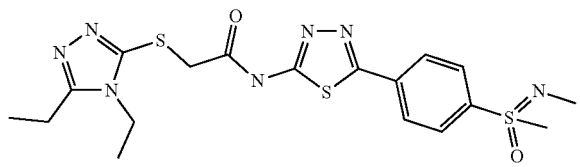 [SMILES: CCc1nnc(SCC(=O)Nc2nnc(-c3ccc(S(C)(=O)=NC)cc3)s2)n1CC]

Purification of the compounds may be made by any procedure within the standards knowledge of the person skilled in the art such as e.g. preparative HPLC. Further particulars as to purification and separation can be found in the General Chemical Procedures' section.

Pharmaceutical Compositions

The present disclosure also relates to a pharmaceutical composition comprising physiologically acceptable surface active agents, carriers, diluents, excipients, smoothing agents, suspension agents, film forming substances, and coating assistants, or a combination thereof; and a compound of Formula (I) as disclosed herein. The compound of Formula (I) included in the pharmaceutical composition may also be any compound of the preferred embodiments described above. Acceptable carriers or diluents, as well as other additives to be combined with a compound of Formula (I) as disclosed herein to provide a pharmaceutical composition, for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, taste masking agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical compositions described herein can be administered to a human patient per se, or in pharmaceutical compositions where they are mixed with other active ingredients, as in combination therapy, or suitable carriers or excipient(s). Examples of active ingredients include Incretin mimetics, Metformins, PPAR agonists, sulfonylureas, insulin and insulin formulations, SGLT inhibitors such as e.g. SGLT2-inhibitors and more specifically e.g. dapagliflozin, glucokinase activators, and bile acid receptor agonists. Further examples of combination therapies are that the compounds disclosed herein may be combined with e.g. methotrexate, glucosamine, DMARDs (disease-modifying antirheumatic drugs), sulfasalazine, and NSAIDs (non-steroidal anti-inflammatory drugs).

Techniques for formulation and administration of the compounds of the instant application may be found in "Remington's Pharmaceutical Sciences," Mack Publishing Co., Easton, Pa., 18th edition, 1990.

The pharmaceutical compositions may be manufactured in a manner that is itself known, e.g., by means of conventional mixing, dissolving, granulating, dragee-making, levigating, emulsifying, encapsulating, entrapping or tableting processes.

Pharmaceutical compositions for use as described herein may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For oral administration, the compounds can be formulated readily by combining the active compounds with pharmaceutically acceptable carriers well known in the art. Such carriers enable the compounds disclosed herein to be formulated as tablets, coated tablets, pills, dragees, capsules, liquids, gels, syrups, slurries, suspensions, sachets, films and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally may include any tablets or capsules of any kind such as e.g. gelatin capsules, as well as soft, sealed capsules made of gelatin and a plasticizer, such as glycerol or sorbitol. The tablets, coated tablets or capsules can contain the active ingredients in admixture with filler such as e.g. lactose, binders such as e.g. starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Merely as a non-limiting example a suitable formulation may be a coated tablet. Such tablet may contain a core and a film-coating. The core may comprise several excipients such as e.g. microcrystalline cellulose, anhydrous lactose, crospovidone, silicon dioxide and magnesium stearate. The film-coating may comprise polyvinyl alcohol, titanium dioxide, macrogol and a colourant. All formulations for oral administration should be in dosages suitable for such administration. Further non-limiting examples may be that the pharmaceutical compositions according to the invention may be formulated as a powder which may optionally be in a sachet form. Such formulations may be dissolved in a glass of water to be drunk by the subject. Moreover, the pharmaceutical formulations according to the invention may be formulated to allow injectable forms of administration.

Pharmaceutical compositions of the invention may also be formulated as immediate release, controlled release or extended release compositions.

Additional therapeutic or diagnostic agents may be incorporated into the pharmaceutical compositions. Alternatively or additionally, pharmaceutical compositions may be combined with other compositions that contain other therapeutic or diagnostic agents.

Uses

The compounds of Formula (I) or pharmaceutical compositions disclosed herein may be used in therapy, such as e.g. for use in treating diabetes, preferably type-2 diabetes.

The compounds of Formula (I) or pharmaceutical compositions disclosed herein may also be used in treatment of disorders and diseases, where the function or dysfunction of AQP9 contributes to the development or maintenance of disease, such as diabetes, atherosclerosis, disuse osteoporosis, non-alcoholic fatty liver disease, acute kidney injury, kidney ischemia-reperfusion injury, inflammatory diseases e.g. inflammatory bowel disease, psoriasis, allergic contact dermatitis or rheumatoid arthritis. Thus, the compounds of Formula (I) or pharmaceutical compositions disclosed herein may be used in therapy, such as for use in treating inflammatory diseases, preferably rheumatoid arthritis.

The compounds of Formula (I) or pharmaceutical compositions disclosed herein may also be used in a medicament. The compounds of Formula (I) or pharmaceutical compositions disclosed herein may also be used to modulate the activity of an aquaporin 9 protein. Preferably, modulating the activity of an aquaporin 9 protein comprises inhibiting the activity of the aquaporin 9 protein. In a preferred embodiment, the use of the compounds of Formula (I) or pharmaceutical compositions disclosed herein to modulate the activity of an aquaporin 9 protein is a non-therapeutic use. The compound of Formula (I) or pharmaceutical composition that is used in any of the described therapies (such as for use in treating diabetes), or used in treatment of disorders and diseases where the function or dysfunction of AQP9 contributes to the development or maintenance of disease, or used in a medicament, or used for modulating the activity of an aquaporin 9 protein (e.g. in a non-therapeutic use) may also be any compound or pharmaceutical composition of the preferred embodiments described above. Alternatively, the compound of Formula (I) that is used in any of the described therapies (such as e.g. for use in treating diabetes), or used in treatment of disorders and diseases where the function or dysfunction of AQP9 contributes to the development or maintenance of disease, or used in a medicament, or used for modulating the activity of an aquaporin 9 protein (e.g. in a non-therapeutic use) may be a compound selected from structures (a)-(ap) as disclosed herein.

Methods of Administration

The compounds or pharmaceutical compositions may be administered to the patient by any suitable means including though oral pathways such as administration in a capsule, tablet, granule, spray, syrup, or other such forms. In another aspect of the invention, the compound or a pharmaceutical composition thereof may be administered parenterally, such as e.g. by injection. The therapeutically effective amount of the compounds disclosed herein required as a dose will depend on the route of administration, the type of animal, including mammal, e.g. human, being treated, and the physical characteristics of the specific animal under consideration. The dose can be tailored to achieve a desired effect, but will depend on such factors as weight, diet, concurrent medication and other factors which those skilled in the medical arts will recognize. Determination of a therapeutically effective amount is well within the capability of those skilled in the art, especially in light of the detailed disclosure provided herein.

Typically, dosages may be between about 10 microgram/kg and about 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from e.g. about 0.5 to about 1000 mg/kg of the patient's body weight. The dosage may be a single one or a series of two or more given in the course of one or more days, as is needed by the patient. In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of e.g. between about 0.1 mg and about 2000 mg of each active ingredient, such as e.g. preferably between about 1 mg and about 500 mg, such as e.g. about 5 to about 200 mg. In cases of administration of a pharmaceutically acceptable salt, dosages may be calculated as the free base. In some embodiments, the composition is administered 1 to 4 times per day. In some embodiments, the compounds will be administered for a period of continuous therapy, for example for a week or more, or for months or years.

Dosage amount and interval may be adjusted individually to provide plasma or tissue levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using a MEC value. Compositions should be administered using a regimen which maintains plasma levels above the MEC for 10-90% of the time, preferably between 30-90% and most preferably between 50-90%.

The compounds or pharmaceutical compositions disclosed herein may be administered to the patient alone or in combination with other therapeutic agents against type 2 diabetes. Examples of such therapeutic agents are current anti-type 2 diabetic therapies such as Incretin mimetics, Metformins, PPAR agonists, sulfonylureas as well as insulin. Additional examples include newer anti-type 2 diabetic drugs such as SGLT inhibitors, glucokinase activators, novel insulin formulations, and bile acid receptor agonists. The therapeutic agents may be administered simultaneously with the compounds or pharmaceutical compositions disclosed herein. Alternatively, the therapeutic agents may be administered sequentially with the compounds or pharmaceutical compositions disclosed herein. The dosage amount and interval between administration of the compounds and therapeutic agents may be adjusted as described immediately above.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to metabolic diseases, inflammatory diseases, cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

General Remarks

Although the present invention has been described above with reference to specific illustrative embodiments, it is not intended to be limited to the specific form set forth herein. Any combination of the above mentioned embodiments should be appreciated as being within the scope of the invention. Rather, the invention is limited only by the accompanying claims and other embodiments than the specific above are equally possible within the scope of these appended claims.

EXPERIMENTAL

The following examples are mere examples and should by no mean be interpreted to limit the scope of the invention. Rather, the invention is limited only by the accompanying claims.

General Chemical Procedures

Nuclear Magnetic Resonance (NMR) spectra were recorded on a Varian instrument at 400 MHz and 25° C. Chemical shifts are reported in ppm (δ) using the residual solvent as internal standard. Peak multiplicities are expressed as follow: s, singlet; d, doublet; dd, doublet of doublets; t, triplet; dt, doublet of triplet; q, quartet; m, multiplet; br s, broad singlet.

LC-MS were acquired on an Agilent 1100 HPLC coupled with an Agilent MSD mass spectrometer operating in ES (+) ionization mode. Column: Waters symmetry 2.1×30 mm C18 or Chromolith RP-18 2×50 mm. Solvent A water+0.1% TFA and solvent B Acetonitrile+0.1% TFA. Wavelength: 254 nm.

Preparative HPLC were performed on a Gilson system. Flow: 10 ml/min Column: kromasil 100-5-C18 column. Wavelength: 254 nm. Solvent A water+0.1% TFA and solvent B Acetonitrile+0.1% TFA. Gradient: 40% to 95% B in 15 min.

All commercial reagents were used as received.

The following abbreviations are used herein.

CDCl$_3$ Chloroform-d
DMF N,N-dimethylformamide
DMSO-d$_6$ Dimethylsulfoxide-d$_6$
HPLC High Performance Liquid Chromatography
LC-MS Liquid Chromatography with Mass Spectrographic detection
NMR Nuclear Magnetic Resonance spectrometry
TFA Trifluoroacetic Acid
Prep HPLC Preparative HPLC Intermediate 1

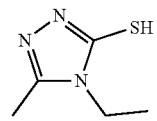

4-Ethyl-5-methyl-4H-1,2,4-triazole-3-thiol

Dissolve 1-amino-3-ethylthiourea (238 mg, 2.00 mmol) in pyridine (10 mL). Add acetyl chloride (149 µL, 2.10 mmol). The solution was stirred at room temperature overnight. Most of the solvent was evaporated. The residue was dissolved in 0.5 M sodium hydroxide (10 mL, 5 mmol). Heat at 100° C. for 4 hours. The mixture was cooled to room temperature and pH was adjusted to 5 using 5M hydrogen chloride. Add ethyl acetate. Shake and collect the organic layer. Extract the water phase four more times with ethyl acetate. The collected organic phases were dried over MgSO₄. The solution was evaporated and the residue was used without any further purification. LC-MS (ES): 144.1 (M+H).

Intermediates 2 to 19 were prepared in a manner analogous to intermediate 1.

Intermediate 2

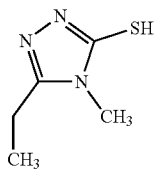

5-ethyl-4-methyl-4H-1,2,4-triazole-3-thiol $^1$H NMR (400 MHz, DMSO-d$_6$) δ 13.43 (s, 1H), 3.39 (s, 3H), 2.71-2.62 (q, 2H), 1.19 (t, 3H).

Intermediate 3

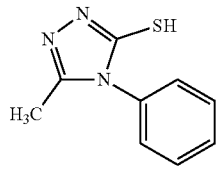

5-methyl-4-phenyl-4H-1,2,4-triazole-3-thiol $^1$H NMR (400 MHz, DMSO-d$_6$) δ 7.61-7.48 (m, 3H), 7.42 (d, 2H), 2.09 (s, 3H)

Intermediate 4

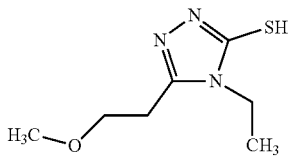

4-ethyl-5-(2-methoxyethyl)-4H-1,2,4-triazole-3-thiol $^1$H NMR (400 MHz, Chloroform-d) δ 11.98 (s, 1H), 4.12 (q, 2H), 3.76 (t, 2H), 3.37 (s, 3H), 2.96 (t, 2H), 1.36 (t, 3H)

Intermediate 5

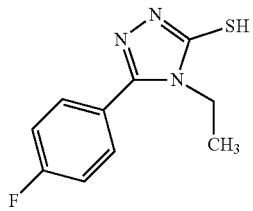

4-ethyl-5-(4-fluorophenyl)-4H-1,2,4-triazole-3-thiol

LC-MS (ES): 224 (M+H), $^1$H NMR (DMSO-d$_6$) δ 7.78-7.71 (m, 2H), 7.42 (t, 2H), 4.02 (q, 2H), 1.13 (t, 3H).

Intermediate 6

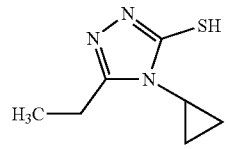

4-cyclopropyl-5-ethyl-4H-1,2,4-triazole-3-thiol $^1$H NMR (400 MHz, Chloroform-d) δ 11.83 (s, 1H), 2.96-2.86 (m, 1H), 2.76 (q, 2H), 1.33 (t, 3H), 1.29-1.10 (m, 4H).

Intermediate 7

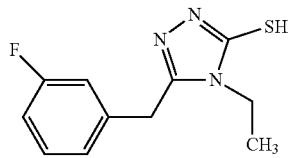 [SMILES: CCn1c(S)nnc1Cc1cccc(F)c1]

4-ethyl-5-(3-fluorobenzyl)-4H-1,2,4-triazole-3-thiol

¹H NMR (400 MHz, Chloroform-d) δ 11.96 (s, 1H), 7.32 (td, 1H), 7.11-6.96 (m, 2H), 6.93 (d, 1H), 4.05 (s, 2H), 3.92 (q, 2H), 1.14 (t, 3H).

Intermediate 8

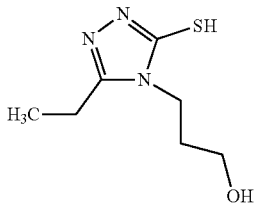

3-(3-ethyl-5-sulfanyl-4H-1,2,4-triazol-4-yl)propan-1-ol

¹H NMR (400 MHz, DMSO-d₆) δ 13.46 (s, 1H), 4.63 (s, 1H), 3.99-3.90 (m, 2H), 3.41-3.34 (m, 2H), 2.70 (q, 2H), 1.80 (m, 2H), 1.21 (t, 3H).

Intermediate 9

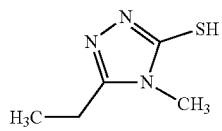

5-ethyl-4-methyl-4H-1,2,4-triazole-3-thiol

¹H NMR (400 MHz, Chloroform-d) δ 11.87 (s, 1H), 3.54 (s, 3H), 2.69 (q, 2H), 1.36 (t, 3H).

Intermediate 10

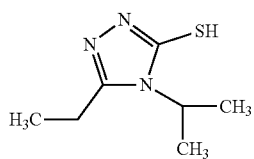

5-ethyl-4-isopropyl-4H-1,2,4-triazole-3-thiol

¹H NMR (400 MHz, Chloroform-d) δ 12.00 (s, 1H), 5.09 (m, 1H), 2.78 (q, 2H), 1.56 (d, 6H), 1.37 (t, 3H).

Intermediate 11

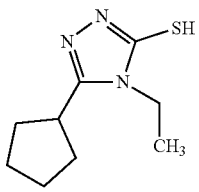

5-cyclopentyl-4-ethyl-4H-1,2,4-triazole-3-thiol

¹H NMR (400 MHz, Chloroform-d) δ 11.87 (s, 1H), 4.09 (q, 2H), 3.02 (m, 1H), 2.14-2.00 (m, 2H), 1.97-1.77 (m, 4H), 1.77-1.62 (m, 2H), 1.39 (t, 3H).

Intermediate 12

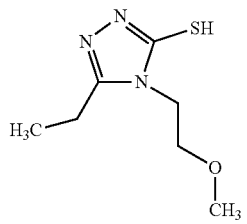

5-ethyl-4-(2-methoxyethyl)-4H-1,2,4-triazole-3-thiol

¹H NMR (400 MHz, Chloroform-d) δ 11.89 (s, 1H), 4.17 (t, 2H), 3.75-3.70 (t, 2H), 3.31 (s, 3H), 2.76 (q, 2H), 1.33 (t, 3H).

Intermediate 13

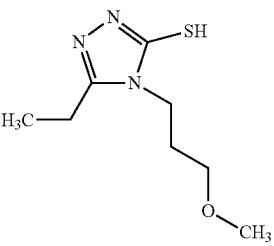

5-ethyl-4-(2-methoxypropyl)-4H-1,2,4-triazole-3-thiol

¹H NMR (400 MHz, Chloroform-d) δ 11.89 (s, 1H), 4.08 (t, 2H), 3.42 (t, 2H), 3.33 (s, 3H), 2.71 (q, 2H), 2.10 (m, 2H), 1.36 (t, 3H).

Intermediate 14

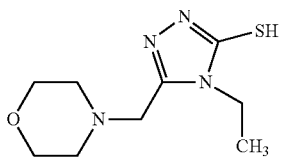

4-ethyl-5-(morpholin-4-ylmethyl)-4H-1,2,4-triazole-3-thiol

¹H NMR (400 MHz, Chloroform-d) δ 11.84 (s, 1H), 4.20 (q, 2H), 3.73 (t, 4H), 3.59 (s, 2H), 2.54 (t, 4H), 1.43 (t, 3H)

Intermediate 15

4-ethyl-5-(propan-2-yl)-4H-1,2,4-triazole-3-thiol

¹H NMR (400 MHz, DMSO-d₆) δ 13.48 (s, 1H), 3.96 (q, 2H), 3.04 (hept, 1H), 1.23 (m, 9H).

Intermediate 16

5-cyclopropyl-4-ethyl-4H-1,2,4-triazole-3-thiol

¹H NMR (400 MHz, Chloroform-d) δ 12.03 (s, 1H), 4.19 (q, 2H), 1.75 (m, 1H), 1.41 (t, 3H), 1.12-0.98 (m, 4H).

Intermediate 17

5-Ethyl-4-phenyl-4H-1,2,4-triazole-3-thiol

LC-MS (ES): 206.0 (M+H), 1H NMR (400 MHz, DMSO-d6) δ 7.60-7.50 (m, 3H), 7.41 (d, 2H), 2.41 (q, 2H), 1.04 (t, 3H).

Intermediate 18

4,5-diethyl-4H-1,2,4-triazole-3-thiol

LC-MS (ES): 158.1 (M+H), ¹H NMR (400 MHz, DMSO-d₆) δ 13.44 (s, 1H), 3.94 (q, 2H), 2.69 (q, 2H), 1.20 (td, 6H).

Intermediate 19

5-Benzyl-4-ethyl-4H-1,2,4-triazole-3-thiol

LC-MS (ES): 220.1 (M+H), ¹H NMR (400 MHz, DMSO-d₆) δ 7.42-7.23 (m, 5H), 4.11 (s, 2H), 3.86 (q, 2H), 0.92 (t, 3H)

Intermediate 20

2-Chloro-N-[5-(4-methoxyphenyl)-1,3,4-thiadiazol-2-yl]acetamide

To a mixture of 2-amino-5-(4-methoxyphenyl)-1,3,4-thiadiazole (417 mg, 2.03 mmol) and triethylamine (425 μl, 3.05 mmol) in 15 ml dioxane was added drop-wise chloroacetyl chloride (206 μl, 2.54 mmol) in 10 ml dioxane over a period of 10 min. The reaction was stirred at room temperature for 4 hours and then poured into 75 ml of water. The resulting precipitate was filtered off and washed with water and dried to give the title product (525 mg, 95%).

LC-MS (ES): 284.1 (M+H), $^1$H NMR (DMSO-d$_6$) δ 12.96 (s, 1H), 7.89 (d, 2H), 7.09 (d, 2H), 4.46 (s, 2H), 3.83 (s, 3H).

Intermediate 21

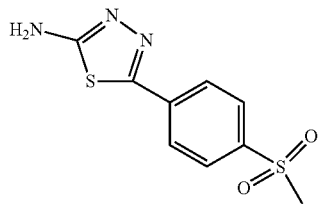 [SMILES: CS(=O)(=O)c1ccc(-c2nnc(N)s2)cc1]

5-(4-methanesulfonylphenyl)-1,3,4-thiadiazol-2-amine

A mixture of 4-(methylsulfonyl)benzoic acid (200 mg, 1 mmol) and thiosemicarbazide (92 mg, 1 mmol) in phosphorous(V) oxychloride was heated to 80° C. for 45 minutes. The reaction mixture was cooled and water (5 ml) was added slowly (exothermic reaction). The reaction mixture was cooled and pH was adjusted to pH 7. The product was filtered and the solid was washed with water and dried to give 200 mg of the title compound as a solid.

LC-MS (ES): 255.9 (M+H), $^1$H NMR (400 MHz, DMSO-d$_6$) 8.00 (dd, 4H), 7.63 (s, 2H), 3.25 (s, 3H).

Intermediate 22

Intermediates 22 was prepared from intermediate 21 in a manner analogous to intermediate 20

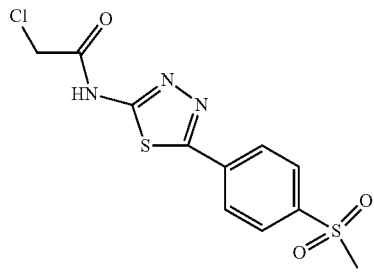 [SMILES: CS(=O)(=O)c1ccc(-c2nnc(NC(=O)CCl)s2)cc1]

2-chloro-N-[5-(4-methanesulfonylphenyl)-1,3,4-thiadiazol-2-yl]acetamide

LC-MS (ES): 332.2 (M+H), $^1$H NMR (400 MHz, DMSO-d$_6$) δ 8.24 (d, 2H), 8.07 (d, 2H), 4.50 (s, 2H), 3.29 (s, 3H).

Intermediate 23

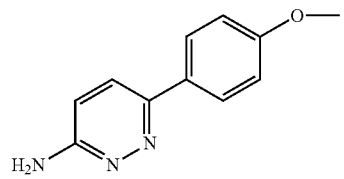

6-(4-methoxyphenyl)pyridazin-3-amine

Amino-6-chloropyridazine (100 mg, 0.77 mmol) and 4-methoxyphenylboronic acid (89 mg, 0.59 mmol) were placed in a vial, under nitrogen. Tetrakis(triphenylphosphine)palladium(0) (15 mg, 13 μmol) was added, followed by toluene (1 ml). A solution of 2 M sodium carbonate (0.4 ml) was added. The mixture was heated at 105° C. for 5 hours. The solvent was evaporated under reduced pressure and the residue was taken up in ethyl acetate, washed with water, dried, filtered and concentrated under reduced pressure. The product was purified on silica by flash column chromatography to afford 100 mg of 6-(4-methoxyphenyl)pyridazin-3-amine as a white solid. (Yield: 84%).

LC-MS (ES): 202.1 (M+H

Intermediate 24

Intermediates 24 was prepared from intermediate 23 in a manner analogous to intermediate 20

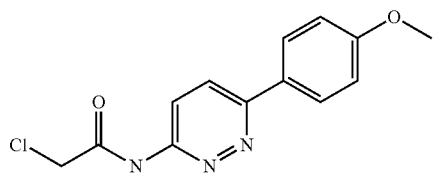 [SMILES: COc1ccc(-c2ccc(NC(=O)CCl)nn2)cc1]

2-chloro-N-[6-(4-methoxyphenyl)pyridazin-3-yl]acetamide $^1$H NMR (400 MHz, DMSO-d$_6$) δ 11.65 (s, 1H), 8.40 (dd, 4H), 8.09 (d, 2H), 4.46 (s, 2H), 3.29 (s, 3H).

Intermediates 25 to 43 were prepared in a manner analogous to intermediate 20.

Intermediate 25

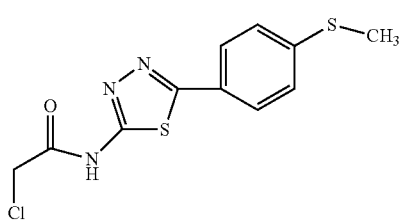 [SMILES: CSc1ccc(-c2nnc(NC(=O)CCl)s2)cc1]

2-chloro-N-{5-[4-(methylsulfanyl)phenyl])-1,3,4-thiadiazol-2-yl]-acetamide $^{1}$H NMR (400 MHz, DMSO-d$_{6}$) δ 13.03 (s, 1H), 7.88 (d, 2H), 7.39 (d, 2H), 4.47 (s, 2H), 2.54 (s, 3H).

Intermediate 26

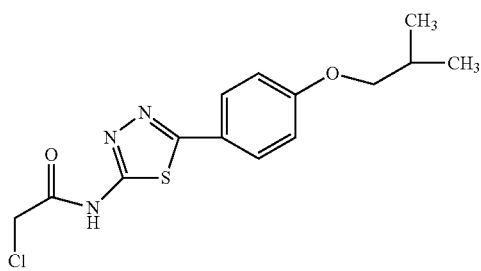 [SMILES: CC(C)COc1ccc(-c2nnc(NC(=O)CCl)s2)cc1]

2-chloro-N-{5-[4-(2-methylpropoxy)phenyl]-1,3,4-thiadiazol-2-yl}acetamide $^{1}$H NMR (400 MHz, DMSO-d$_{6}$) δ 12.96 (s, 1H), 7.87 (d, 2H), 7.07 (d, 2H), 4.46 (s, 2H), 3.90-3.79 (d, 2H), 2.04 (m, 1H), 0.99 (d, 6H).

Intermediate 27

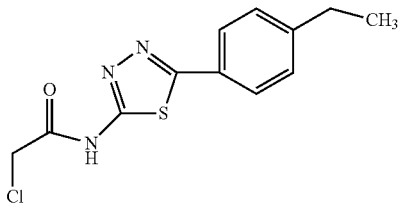 [SMILES: CCc1ccc(-c2nnc(NC(=O)CCl)s2)cc1]

2-chloro-N-[5-(4-ethylphenyl)-1,3,4-thiadiazol-2-yl]acetamide $^{1}$H NMR (400 MHz, DMSO-d$_{6}$) δ 13.01 (s, 1H), 7.86 (d, 2H), 7.37 (d, 2H), 4.47 (s, 2H), 2.67 (q, 2H), 1.21 (t, 3H).

Intermediate 28

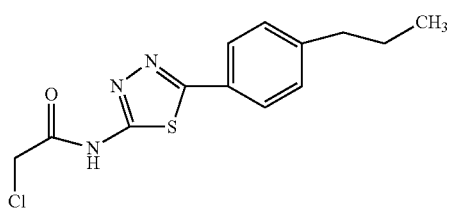 [SMILES: CCCc1ccc(-c2nnc(NC(=O)CCl)s2)cc1]

2-chloro-N-[5-(4-propylphenyl)-1,3,4-thiadiazol-2-yl]acetamide $^{1}$H NMR (400 MHz, DMSO-d$_{6}$) δ 13.01 (s, 2H), 7.35 (d, 2H), 4.47 (s, 2H), 2.62 (t, 2H), 1.62 (m, 2H), 0.91 (t, 3H).

Intermediate 29

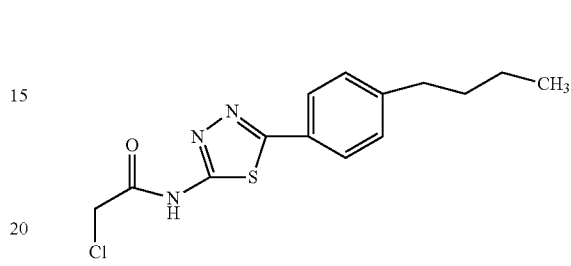

2-chloro-N-[5-(4-butylphenyl)-1,3,4-thiadiazol-2-yl]acetamide $^{1}$H NMR (400 MHz, DMSO-d$_{6}$) δ 13.00 (s, 1H), 7.85 (d, 2H), 7.35 (d, 2H), 4.47 (s, 2H), 2.64 (t, 2H), 1.58 (p, 2H), 1.30 (m, 2H), 0.90 (t, 3H).

Intermediate 30

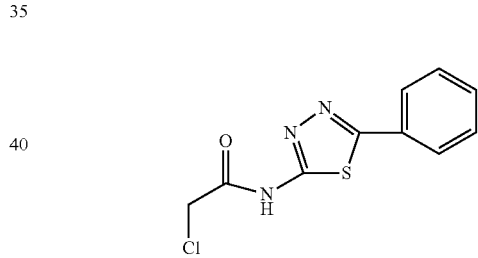

2-chloro-N-(5-phenyl-1,3,4-thiadiazol-2-yl)acetamide $^{1}$H NMR (400 MHz, DMSO-d$_{6}$) 13.04 (s, 1H), 7.96 (m, 2H), 7.57-7.51 (m, 3H), 4.48 (s, 2H).

Intermediate 31

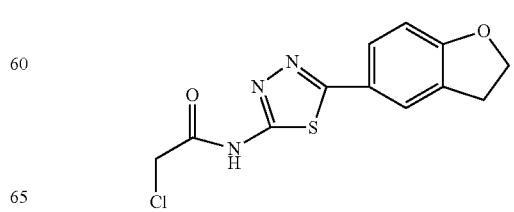

2-chloro-N-[5-(2,3-dihydro-1-benzofuran-5-yl)-1,3,4-thiadiazol-2-yl]acetamide

¹H NMR (400 MHz, DMSO-d$_6$) δ 7.82 (s, 1H), 7.69 (d, 1H), 6.89 (d, 1H), 4.61 (t, 2H), 4.45 (s, 2H), 3.25 (t, 2H).

Intermediate 32

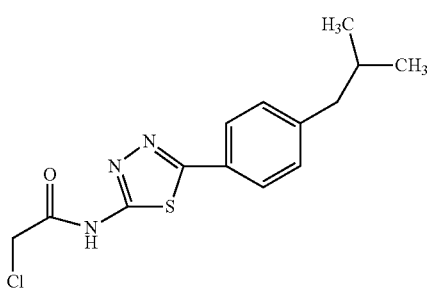 [SMILES: CC(C)Cc1ccc(-c2nnc(NC(=O)CCl)s2)cc1]

2-chloro-N-{5-[4-(2-methylpropyl)phenyl]-1,3,4-thiadiazol-2-yl}acetamide

¹H NMR (400 MHz, DMSO-d$_6$) δ 13.00 (s, 2H), 7.86 (d, 2H), 7.32 (d, 2H), 4.47 (s, 2H), 2.52 (d, 2H), 1.87 (m, 1H), 0.88 (d, 6H).

Intermediate 33

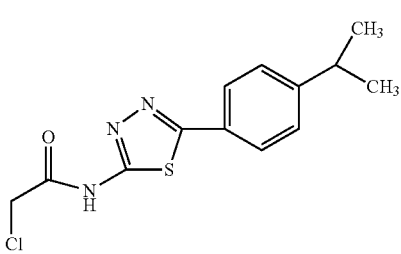 [SMILES: CC(C)c1ccc(-c2nnc(NC(=O)CCl)s2)cc1]

2-chloro-N-{5-[4-(propan-2-yl)phenyl]-1,3,4-thiadiazol-2-yl}acetamide

¹H NMR (400 MHz, DMSO-d$_6$) δ 13.01 (s, 1H), 7.87 (d, 2H), 7.41 (d, 2H), 4.47 (s, 2H), 2.96 (hept, 1H), 1.23 (d, 6H).

Intermediate 34

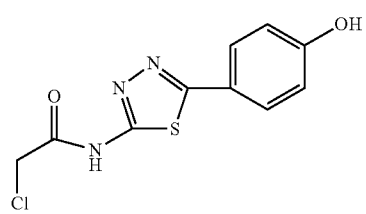 [SMILES: O=C(CCl)Nc1nnc(-c2ccc(O)cc2)s1]

2-chloro-N-[5-(4-hydroxyphenyl)-1,3,4-thiadiazol-2-yl]acetamide

¹H NMR (400 MHz, DMSO-d$_6$) δ 10.09 (s, 1H), 7.77 (d, 2H), 6.89 (d, 2H), 4.45 (s, 2H).

Intermediate 35

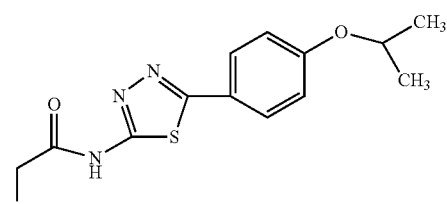

2-chloro-N-{5-[4-(propan-2-yloxy)phenyl]-1,3,4-thiadiazol-2-yl}acetamide

¹H NMR (400 MHz, DMSO-d$_6$) δ 12.96 (s, 1H), 7.86 (d, 2H), 7.05 (d, 2H), 4.71 (hept, 1H), 4.46 (s, 2H), 1.30 (d, 6H).

Intermediate 36

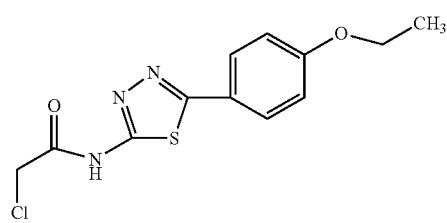 [SMILES: CCOc1ccc(-c2nnc(NC(=O)CCl)s2)cc1]

2-chloro-N-[5-(4-ethoxyphenyl)-1,3,4-thiadiazol-2-yl]acetamide

¹H NMR (400 MHz, DMSO-d$_6$) δ 12.96 (s, 1H), 7.87 (d, 2H), 7.06 (d, 2H), 4.46 (s, 2H), 4.16-4.07 (q, 2H), 1.35 (t, 3H).

Intermediate 37

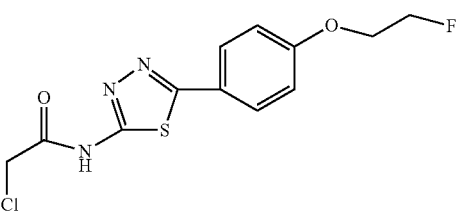 [SMILES: O=C(CCl)Nc1nnc(-c2ccc(OCCF)cc2)s1]

2-chloro-N-{5-[4-(2-fluoroethoxy)phenyl]-1,3,4-thiadiazol-2-yl}acetamide $^1$H NMR (400 MHz, DMSO-d$_6$) δ 12.97 (s, 1H), 7.90 (d, 2H), 7.12 (d, 2H), 4.86-4.80 (m, 1H), 4.75-4.68 (m, 1H), 4.47 (s, 2H), 4.40-4.33 (m, 1H), 4.28 (dd, 1H).

Intermediate 38

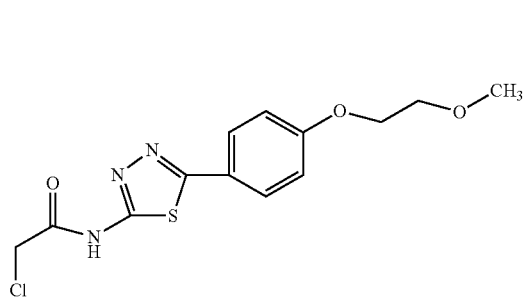 [SMILES: COCCOc1ccc(-c2nnc(NC(=O)CCl)s2)cc1]

2-chloro-N-{5-[4-(2-methoxyethoxy)phenyl]-1,3,4-thiadiazol-2-yl}acetamide $^1$H NMR (DMSO-d$_6$) δ 12.97 (s, 1H), 7.88 (d, 2H), 7.09 (d, 2H), 4.46 (s, 2H), 4.17 (t, 2H), 3.68 (t, 2H), 3.33 (s, 3H).

Intermediate 39

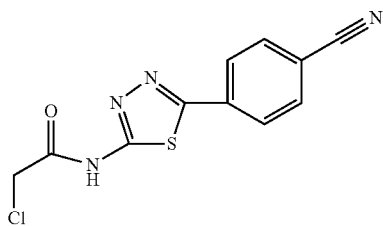 [SMILES: N#Cc1ccc(-c2nnc(NC(=O)CCl)s2)cc1]

2-chloro-N-(5-(4-cyanophenyl)-1,3,4-thiadiazol-2-yl)acetamide $^1$H NMR (400 MHz, DMSO-d$_6$) δ 8.16 (d, 2H), 8.00 (d, 2H), 4.51 (s, 2H).

Intermediate 40

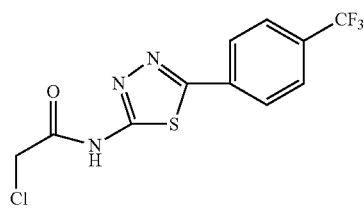 [SMILES: O=C(CCl)Nc1nnc(-c2ccc(C(F)(F)F)cc2)s1]

2-chloro-N-(5-(4-trifluoromethylphenyl)-1,3,4-thiadiazol-2-yl)acetamide $^1$H NMR (400 MHz, DMSO-d$_6$) δ 13.19 (s, 1H), 8.20 (d, 2H), 7.90 (d, 2H), 4.51 (s, 2H).

Intermediate 41

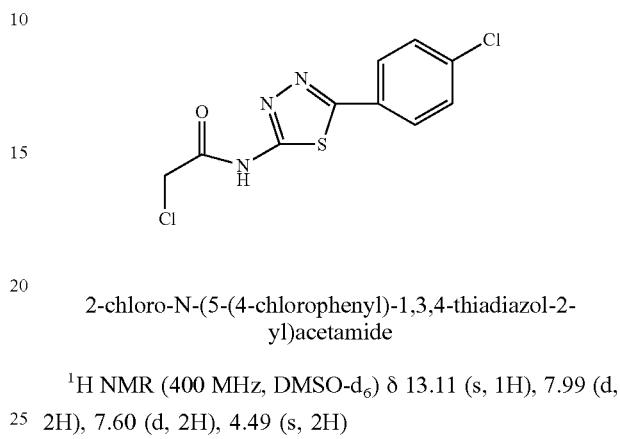

2-chloro-N-(5-(4-chlorophenyl)-1,3,4-thiadiazol-2-yl)acetamide $^1$H NMR (400 MHz, DMSO-d$_6$) δ 13.11 (s, 1H), 7.99 (d, 2H), 7.60 (d, 2H), 4.49 (s, 2H)

Intermediate 42

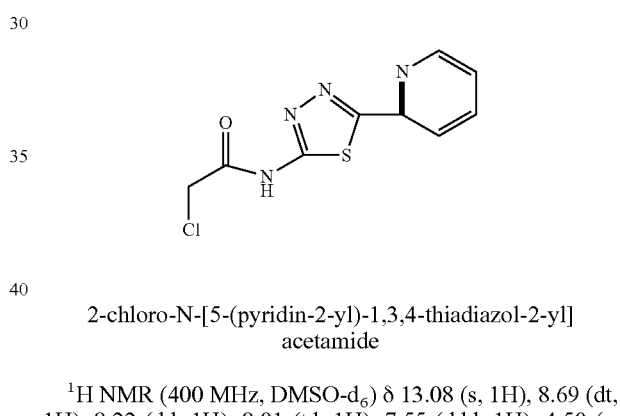

2-chloro-N-[5-(pyridin-2-yl)-1,3,4-thiadiazol-2-yl]acetamide $^1$H NMR (400 MHz, DMSO-d$_6$) δ 13.08 (s, 1H), 8.69 (dt, 1H), 8.22 (dd, 1H), 8.01 (td, 1H), 7.55 (ddd, 1H), 4.50 (s, 2H).

Intermediate 43

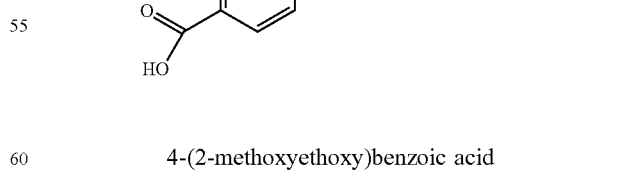

4-(2-methoxyethoxy)benzoic acid 4-hydroxybenzoic acid (2.50 g, 18.1 mmol) and Potassium hydroxide (2.33 g, 41.5 mmol) are dissolved in ethanol (72 ml). 1-bromo-2-methoxyethane (2.2 ml, 23.5 mmol) is added dropwise.

The reaction mixture is refluxed under nitrogen for 24 hours. More potassium hydroxide (2.00 g, 35.6 mmol), dissolved in ethanol (25 ml) is added to the suspension which is refluxed for another 20 h. The solvent is evaporated and, after addition of water (100 ml), the reaction mixture is acidified with hydrochloric acid (5M) to pH 2.5 and extracted with diethyl ether (2×200 ml). The organic phase is dried (sodium sulfate) and evaporated to give 1.98 g, (55%) product.

1H NMR: (DMSO-d6): δ 7.88 (m, 2H), 7.02 (m, 2H), 4.16 (m, 2H), 3.67 (m, 2H), 3.31 (s, 3H).

Intermediates 44 to 46 were prepared in a manner analogous to intermediate 43 Intermediate 44

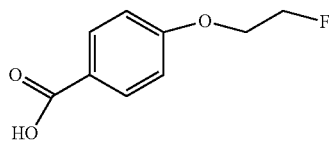 [SMILES: O=C(O)c1ccc(OCCF)cc1]

4-(2-fluoroethoxy)benzoic acid $^1$H NMR (400 MHz, DMSO-d$_6$) δ 12.65 (s, 1H), 7.89 (d, 2H), 7.05 (d, 2H), 4.85-4.79 (m, 1H), 4.73-4.67 (m, 1H), 4.39-4.32 (m, 1H), 4.31-4.24 (m, 1H).

Intermediate 45

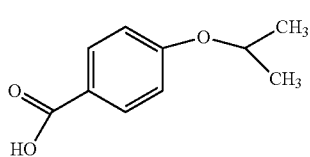

4-(propan-2-yloxy)benzoic acid $^1$H NMR (400 MHz, Chloroform-d) δ 8.05 (d, 2H), 6.91 (d, 2H), 4.66 (hept, 1H), 1.37 (d, 6H).

Intermediate 46

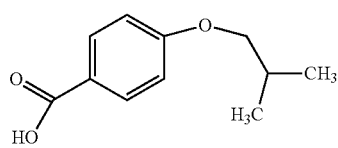

4-(2-methylpropoxy)benzoic acid $^1$H NMR (400 MHz, Chloroform-d) δ 8.06 (d, 2H), 6.94 (d, 2H), 3.79 (d, 2H), 2.12 (m, 1H), 1.04 (d, 6H).

Intermediate 47

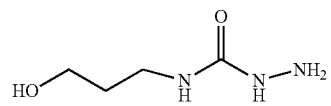

1-amino-3-(3-hydroxypropyl)thiourea

To a mixture of triethylamine (10.86 ml, 78 mmol), carbon disulfide (4.3 ml, 72 mmol) and water (2.5 ml) was 3-aminopropan-1-ol (1.5 g, 60 mmol) added dropwise at a temperature below 20° C. The mixture was stirred for 3 hours. Water (18 ml) and hydrazine hydrate (4.7 ml, 60 mmol) were added. The mixture was heated over night and then cooled to room temperature. The pH was adjusted with Sodium hydroxide and then concentrated under reduced pressure to ca 20 ml. 2-propanol (50 ml) was added and the solution was left in a freezer for 48 hours. Product was filtered off and the crystals was washed with ice-cooled 2-propanol to give 5.6 g (62%) of product $^1$H NMR (400 MHz, DMSO-d$_6$) δ 8.58 (s, 1H), 7.90 (s, 1H), 4.52 (t, 1H), 4.44 (s, 2H), 3.50 (q, 2H), 3.43 (q, 2H), 1.64 (p, 2H).

Example 1

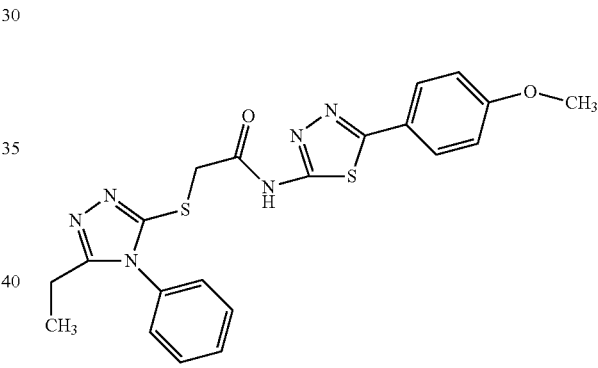

2-[(5-ethyl-4-phenyl-4H-1,2,4-triazol-3-yl)sulfanyl]-N-[5-(4-methoxyphenyl)-1,3,4-thiadiazol-2-yl]acetamide To a mixture of 2-chloro-N-[5-(4-methoxyphenyl)-1,3,4-thiadiazol-2-yl]-acetamide (28.5 mg, 0.10 mmol) intermediate 20, Potassium carbonate (55 mg, 0.40 mmol and 4-phenyl-5-ethyl-4H-1,2,4-triazole-3-thiol (20.5 mg, 0.10 mmol) intermediate 17 in DMF (1 ml) was heated at 80° C. for 3 hrs. The mixture was diluted with 5 ml of water and 1 ml CH$_3$CN and purified on HPLC.

LC-MS (ES): 453.1 (M+H), $^1$H NMR (400 MHz, DMSO-d$_6$) δ 7.88 (d, 2H), 7.60 (m, 3H), 7.48 (m, 2H), 7.08 (d, 2H), 4.21 (s, 2H), 3.83 (s, 3H), 2.54 (q, 2H), 1.09 (t, 3H).

Example 2

Example 2 was prepared from intermediate 20 and 18 in a manner analogous to example 1.

Intermediate 20 2-chloro-N-[5-(4-methoxyphenyl)-1,3,4-thiadiazol-2-yl]-acetamide Intermediate 18 4,5-diethyl-4H-1,2,4-triazole-3-thiol

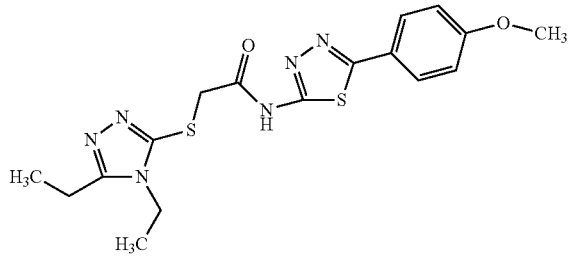 [SMILES: CCc1nnc(SCC(=O)Nc2nnc(-c3ccc(OC)cc3)s2)n1CC]

2-[(diethyl-4H-1,2,4-triazol-3-yl)sulfanyl]-N-[5-(4-methoxyphenyl)-1,3,4-thiadiazol-2-yl]acetamide LC-MS (ES): 405.1 (M+H), $^1$H NMR (400 MHz, DMSO-$d_6$) δ 7.87 (d, 2H), 7.08 (d, 2H), 4.26 (s, 2H), 3.97 (q, 2H), 3.83 (s, 3H), 2.76 (q, 2H), 1.25 (td, 6H).

Example 3

Example 3 was prepared in a manner analogous to example 1.

Intermediate 20 2-chloro-N-[5-(4-methoxyphenyl)-1,3,4-thiadiazol-2-yl]-acetamide Intermediate 19 5-benzyl-4-ethyl-4H-1,2,4-triazole-3-thiol

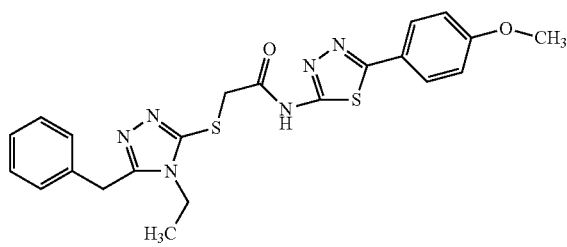 [SMILES: CCn1c(Cc2ccccc2)nnc1SCC(=O)Nc1nnc(-c2ccc(OC)cc2)s1]

2-[(5-benzyl-4-ethyl-4H-1,2,4-triazol-3-yl)sulfanyl]-N-[5-(4-methoxyphenyl)-1,3,4-thiadiazol-2-yl]acetamide LC-MS (ES): 467.0 (M+H), $^1$H NMR (400 MHz, DMSO-$d_6$) δ 7.87 (d, 2H), 7.35-7.26 (m, 2H), 7.25-7.19 (m, 3H), 7.08 (d, 2H), 4.24 (s, 2H), 4.17 (s, 2H), 3.89 (q, 2H), 3.83 (s, 3H), 0.97 (t, 3H).

Example 4

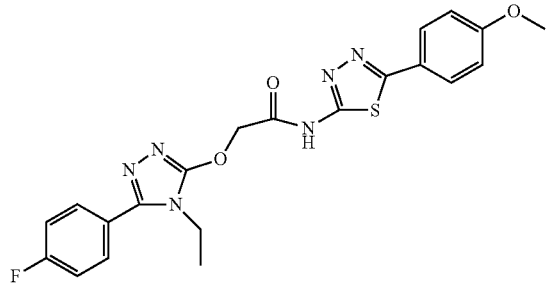 [SMILES: CCn1c(OCC(=O)Nc2nnc(-c3ccc(OC)cc3)s2)nnc1-c1ccc(F)cc1]

A. 4-ethyl-3-(4-fluorophenyl)-5-(methylsulfanyl)-4H-1,2,4-triazole

A mixture of 4-ethyl-5-(4-fluorophenyl)-4H-1,2,4-triazole-3-thiol (307 mg, 1.37 mmol) intermediate 5, methyl iodide (86 μl, 1.37 mmol) and potassium carbonate (380 mg, 2.75 mmol) in DMF (2.5 ml) was heated at 80° C. for 3 hrs. The product was extracted between Ethyl acetate and water. The organic phase was dried, filtered and concentrated under reduced pressure to give the title compound.

LC-MS (ES): 455.2 (M+H), 1H NMR (400 MHz, DMSO-d6) δ 12.95 (s, 1H), 7.87 (d, 2H), 7.73 (dd, 2H), 7.41 (t, 2H), 7.08 (d, 2H), 4.85 (s, 2H), 3.83 (s, 3H), 3.77 (q, 2H), 1.14 (t, 3H)

B. 4-ethyl-3-(4-fluorophenyl)-5-methanesulfonyl-4H-1,2,4-triazole

4-Ethyl-3-(4-fluorophenyl)-5-methylsulfanyl)-4,5-dihydro-1H-1,2,4-triazole (912 mg, 3.84 mmol) was dissolved in ethanol (20 ml). Ammonium molybdate tetrahydrate (1.4 g, 1.15 mmol) and hydrogen peroxide (4.3 ml, 38 mmol 30% $H_2O_2$) are added and the reaction mixture was stirred until no starting material was left. The reaction mixture was extracted between ethyl acetate and water. The combined organic extracts were dried, filtered and concentrated under reduced pressure. The product was purified by flash chromatography to give the title product.

$^1$H NMR (400 MHz, DMSO-$d_6$) 7.79 (dd, 2H), 7.46 (t, 2H), 4.28 (q, 2H), 3.65 (s, 3H), 1.26 (t, 3H)

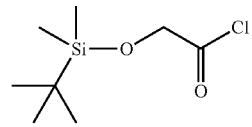

C. 2-[(tert-butyldimethylsilyl)oxy]acetyl chloride

To a stirred solution of 2-hydroxyacetic acid (200 mg, 2.63 mmol) and tertbutyldimethylsilyl chloride (860 mg, 5.71 mmol) in dimethylformamide (2 ml), imidazole (750 mg, 11 mmol) was added and resulting reaction mixture was stirred under N₂ for 18 hours. Then mixture was poured into water and compound was extracted with petroleum ether (3×25 mL). The combined petroleum ether layer was washed with saturated NaHCO₃ solution, dried (MgSO₄), filtered and concentrated under reduced pressure to give the product, which was used, as such, for the next step.

To a solution of crude 2-[(tert-butyldimethylsil)oxy] acetic acid in dichloromethane (10 ml) containing 1-drop of DMF was oxalyl chloride (284 µl, 3.31 mmol) added slowly under N₂ for 5 minutes. The resulting reaction mixture was stirred at room temperature for 1 hour. The resulting reaction mixture was concentrated under reduced pressure to 490 mg of the acid chloride which was used, as such, for the next step.

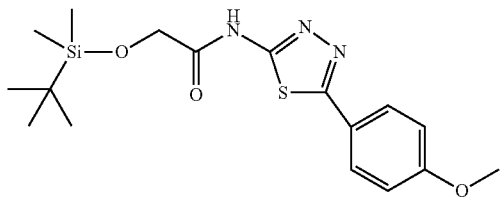 [SMILES: COc1ccc(-c2nnc(NC(=O)CO[Si](C)(C)C(C)(C)C)s2)cc1]

D. 2-[(tert-butyldimethylsilyl)oxy]-N-[5-(4-methoxyphenyl)-1,3,4-thiadiazol-2-yl]acetamide To a solution of 5-(4-methoxyphenyl)-1,3,4-thiadiazol-2-amine (100 mg, 0.48 mmol in Dioxane (1.5 ml) and triethylamine (134 µl, 0.97 mmol) was added 2-[(tert-butyldimethylsilyl)oxy]acetyl chloride in THF (1.5 ml) dropwise. The solution was stirred for 2 hours at room temperature. Ethyl acetate was added and the organic solution was washed with water, dried, filtered and concentrated under reduce pressure to the title compound.

LC-MS (ES): 380.0 (M+H), ¹H NMR (400 MHz, Chloroform-d) δ 7.92 (d, 2H), 7.02 (d, 2H), 4.43 (s, 2H), 3.89 (s, 3H), 0.98 (ds, 9H), 0.20 (ds, 6H).

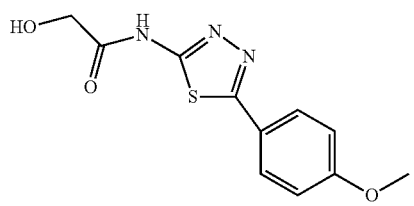 [SMILES: COc1ccc(-c2nnc(NC(=O)CO)s2)cc1]

E. 2-hydroxy-N-[5-(4-methoxyphenyl)-1,3,4-thiadiazol-2-yl]acetamide

To an cold stirred solution of 2-[(tert-butyldimethylsilyl)oxy]-N-[5-(4-methoxyphenyl)-1,3,4-thiadiazol-2-yl]acetamide (60 mg, 0.16 mmol) in tetrahydrofuran (1 mL), a solution of tetrabutylammonium fluoride 1M (470µ, 0.47 mmol) in tetrahydrofuran was added. The resulting reaction mixture was allowed to warm to room temperature, and stirring was continued for 1 hour. The solvent was then evaporated and the residue was dissolved in ethyl acetate and washed with saturated NaHCO₃ and then with brine. The organic solution was dried (MgSO4), filtered and concentrated under reduced pressure to give crude product, which was used, as such, for the next step.

LC-MS (ES): 266.0 (M+H),

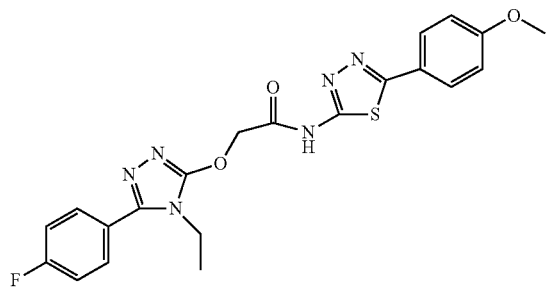 [SMILES: CCn1c(OCC(=O)Nc2nnc(-c3ccc(OC)cc3)s2)nnc1-c1ccc(F)cc1]

F. 2-{[4-ethyl-5-(4-fluorophenyl)-4H-1,2,4-triazol-3-yl]oxy}-N-[5-(4-methoxyphenyl)-1,3,4-thiadiazol-2-yl]acetamide A mixture of 4-ethyl-3-(4-fluorophenyl)-5-methanesulfonyl-4H-1,2,4-triazole (42 mg; 0.15 mmol), 2-hydroxy-N-[5-(4-methoxyphenyl)-1,3,4-thiadiazol-2-yl]acetamide (46 mg, 0.17 mmol) and Cesium carbonate (166 mg, 0.51 mmol) are dissolved in DMF (1 ml). The mixture was heated to 50° C. and stirred overnight. The temperature was raised to 120° C. and the mixture was stirred for 24 hours. To the solution was H₂O:CH₃CN (70:30, 10 ml) added. The product was purified by HPLC and the pure fractions were lyophilized to give 9 mg of pure product.

LC-MS (ES): 455.2 (M+H), ¹H NMR (400 MHz, DMSO-d₆) 12.95 (s, 1H), 7.87 (d, 2H), 7.73 (dd, 2H), 7.41 (t, 2H), 7.08 (d, 2H), 4.85 (s, 2H), 3.83 (s, 3H), 3.77 (q, 2H), 1.14 (t, 3H).

Example 5

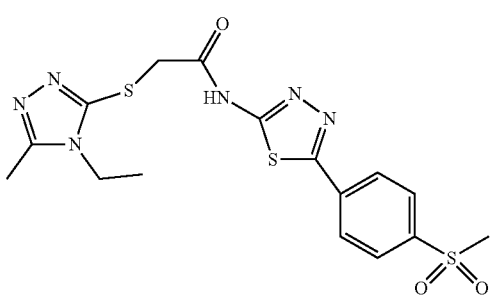

2-[(4-ethyl-5-methyl-4H-1,2,4-triazol-3-yl)sulfanyl]-N-[5-(4-methanesulfonylphenyl)-1,3,4-thiadiazol-2-yl]acetamide Mix 5-(methanesulfonylphenyl)-1,3,4-thiadiazol-2-amine Intermediate 21 (26 mg, 0,102 mmol) with dioxane (2 mL). Add triethylamine (22.7 μL, 0.163 mmol). Add Chloroacetyl chloride (10.1 μL, 0.127 mmol) neat, drop-wise. The reaction was stirred at room temperature overnight. Potassium Carbonate (56.3 mg, 0.407 mmol), 4-ethyl-5-methyl-4H-1,2,4-triazole-3-thiol Intermediate 1 (21.9 mg, 0.153 mmol) and DMF (1.0 mL) were added. The mixture was heated at 80° C. for 3 hours. The heating was turned off and the reaction was stirred at room temperature overnight. The suspension was filtered. Most of the dioxane was evaporated. The product was purified by prep HPLC to obtain of the title compound. 22 mg, (49%)

LC-MS (ES): 439.1 (M+H), $^1$H NMR (400 MHz, DMSO-$d_6$) δ 8.22 (d, 2H), 8.06 (d, 2H), 4.27 (s, 2H), 3.96 (q, 2H), 3.28 (s, 3H), 2.40 (s, 3H), 1.25 (t, 3H).

Example 6

Example 6 was prepared from intermediate 22 and 15 in a manner analogous to example 5.

Intermediate 22 2-chloro-N-[5-(4-methanesulfonyl-phenyl)-1,3,4-thiadiazol-2-yl]acetamide Intermediate 15
4-ethyl-5-(propan.2.yl)-4H-1,2,4-triazole-3-thiol

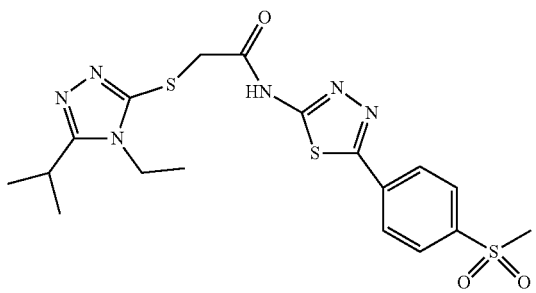 [SMILES: CCn1c(SCC(=O)Nc2nnc(-c3ccc(S(C)(=O)=O)cc3)s2)nnc1C(C)C]

2-{[4-ethyl-5-(propan-2-yl)-4H-1,2,4-triazol-3-yl]sulfanyl}-N-[5-(4-methanesulfonylphenyl)-1,3,4-thiadiazol-2-yl]acetamide LC-MS (ES): 467.1 (M+H), $^1$H NMR (400 MHz, DMSO-$d_6$) δ 8.22 (d, 2H), 8.06 (d, 2H), 4.29 (s, 2H), 3.98 (q, 2H), 3.28 (s, 3H), 3.16-3.07 (m, 1H), 1.27 (m, 9H).

Example 7

Example 7 was prepared from intermediate 22 and 16 in a manner analogous to example 5.

Intermediate 22 2-chloro-N-[5-(4-methanesulfonyl-phenyl)-1,3,4-thiadiazol-2-yl]acetamide Intermediate 16
5-cyclopropyl-4-ethyl-4H-1,2,4-triazole-3-thiol

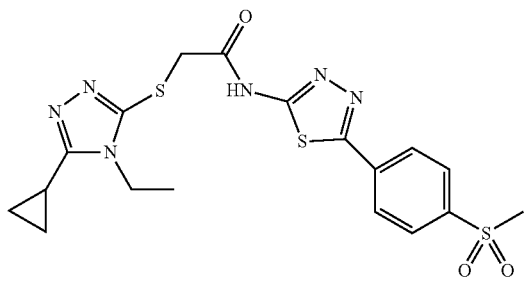 [SMILES: CCn1c(SCC(=O)Nc2nnc(-c3ccc(S(C)(=O)=O)cc3)s2)nnc1C1CC1]

2-[(5-cyclopropyl-4-ethyl-4H-1,2,4-triazol-3-yl)sulfanyl]-N-[5-(4-methanesulfonylphenyl)-1,3,4-thiadiazol-2-yl]acetamide LC-MS (ES): 465.0 (M+H), $^1$H NMR (400 MHz, DMSO-$d_6$) δ 8.22 (d, 2H), 8.06 (d, 2H), 4.23 (s, 2H), 4.07 (q, 2H), 3.28 (s, 3H), 2.01 (m, 1H), 1.29 (t, 3H), 0.98 (d, 2H), 0.89 (m, 2H).

Example 8

Example 8 was prepared from intermediate 22 and 18 in a manner analogous to example 5

Intermediate 22 2-chloro-N-[5-(4-methanesulfonyl-phenyl)-1,3,4-thiadiazol-2-yl]acetamide Intermediate 18 4,5-diethyl-4H-1,2,4-triazole-3-thiol

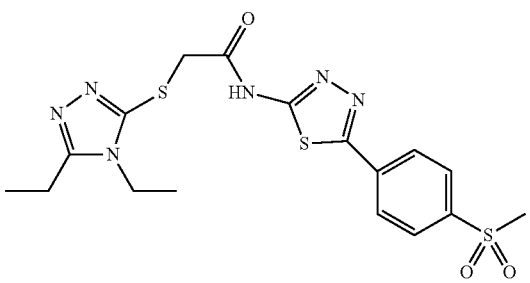 [SMILES: CCc1nnc(SCC(=O)Nc2nnc(-c3ccc(S(C)(=O)=O)cc3)s2)n1CC]

2-[(diethyl-4H-1,2,4-triazol-3-yl)sulfanyl]-N-[5-(4-methanesulfonyl phenyl)-1,3,4-thiadiazol-2-yl]acetamide LC-MS (ES): 453.0 (M+H), $^1$H NMR (400 MHz, DMSO-$d_6$) δ 8.22 (d, 2H), 8.06 (d, 2H), 4.27 (s, 2H), 3.94 (q, 2H), 3.28 (s, 3H), 2.73 (q, 2H), 1.24 (m, 6H).

Example 9

Example 9 was prepared from intermediate 20 and 5 in a manner analogous to example 5

Intermediate 20 2-chloro-N-[5-(4-methoxyphenyl)-1,3,4-thiadiazol-2-yl]-acetamide Intermediate 5 4-ethyl-5-(4-fluorophenyl)-4H-1,2,4-triazole-3-thiol

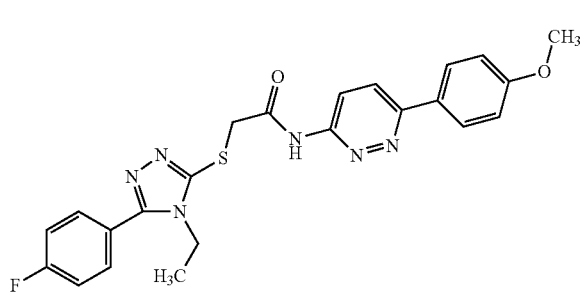 [SMILES: CCn1c(SCC(=O)Nc2ccc(-c3ccc(OC)cc3)nn2)nnc1-c1ccc(F)cc1]

2-{[4-ethyl-5-(4-fluorophenyl)-4H-1,2,4-triazol-3-yl]sulfanyl}-N-[6-(4-methoxyphenyl)pyridazin-3-yl] acetamide LC-MS (ES): 465.1 (M+H), $^1$H NMR (400 MHz, DMSO-$d_6$) δ 11.50 (s, 1H), 8.30 (d, 1H), 8.19 (d, 1H), 8.07 (d, 2H), 7.71 (dd, 2H), 7.41 (t, 2H), 7.09 (d, 2H), 4.34 (s, 2H), 4.03 (q, 2H), 3.83 (s, 3H), 1.23 (t, 3H).

Example 10

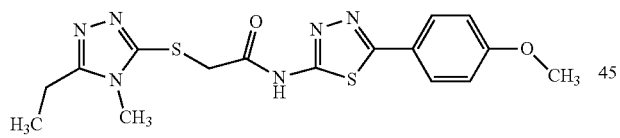

2-[(5-ethyl-4-methyl-4H-1,2,4-triazol-3-yl)sulfanyl]-N-[5-(4-methoxyphenyl)-1,3,4-thiadiazol-2-yl]acetamide A mixture of 2-chloro-N-[5-(4-methoxyphenyl)-1,3,4-thiadiazol-2-yl]-acetamide Intermediate 20 (85.1 mg, 0.30 mmol), Potassium carbonate (165 mg, 1.2 mmol and 5-ethyl-4-methyl-4H-1,2,4-triazole-3-thiol Intermediate 9 (43 mg, 0.30 mmol) in dimethylformamide (1 ml) was heated at 80° C. over night. The mixture was diluted with 6 ml of water and acidified with hydrochloric acid to pH 6 (0.2M). The suspension was centrifuged and the solid was washed three times (3×6 ml) with water to give 22 mg. LC-MS (ES): 391.1 (M+H), $^1$H NMR (400 MHz, DMSO-$d_6$) δ 12.87 (s, 1H), 7.87 (d, 2H), 7.08 (d, 2H), 4.15 (s, 2H), 3.83 (s, 3H), 3.49 (s, 3H), 2.70 (q, 2H), 1.21 (t, 3H).

Example 11

Example 11 was prepared from intermediate 20 and 3 in a manner analogous to example 10

Intermediate 20 2-chloro-N-[5-(4-methoxyphenyl)-1,3,4-thiadiazol-2-yl]-acetamide Intermediate 3 5-methyl-4-phenyl-4H-1,2,4-triazole-3-thiol

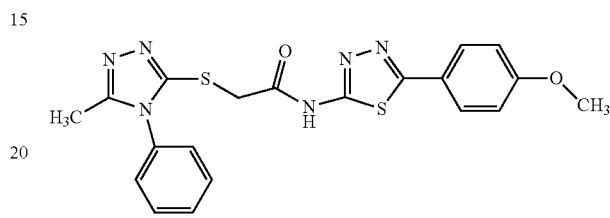

N-[5-(4-methoxyphenyl)-1,3,4-thiadiazol-2-yl]-2-[(5-methyl-4-phenyl-4H-1,2,4-triazol-3-yl)sulfanyl] acetamide Yield: 50 mg LC-MS (ES): 439.2 (M+H), $^1$H NMR (400 MHz, DMSO-$d_6$) δ 12.88 (s, 1H), 7.88 (d, 2H), 7.60 (d, 3H), 7.50-7.45 (m, 2H), 7.08 (d, 2H), 4.20 (s, 2H), 3.83 (s, 3H), 2.20 (s, 3H).

Example 12

Example 12 was prepared from intermediate 25 and 18 in a manner analogous to example 10

Intermediate 25 2-chloro-N-{5-[4-(methylsulfanyl) phenyl])-1,3,4-thiadiazol-2-yl]-acetamide Intermediate 18 4,5-diethyl-4H-1,2,4-triazole-3-thiol
Intermediate 5

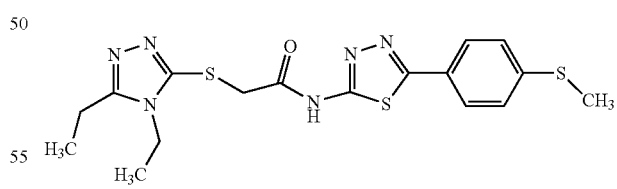

2-[(diethyl-4H-1,2,4-triazol-3-yl)sulfanyl]-N-{5-[4-(methylsulfanyl)phenyl])-1,3,4-thiadiazol-2-yl]acetamide Yield: 70 mg LC-MS (ES): 421.1 (M+H), $^1$H NMR (400 MHz, DMSO-$d_6$) δ 12.95 (s, 1H), 7.86 (d, 2H), 7.38 (d, 2H), 4.23 (s, 2H), 3.93 (q, 2H), 2.71 (q, 2H), 2.53 (s, 3H), 1.23 (t, 6H).

Example 13

Example 13 was prepared from intermediate 26 and 18 in a manner analogous to example 10

Intermediate 26 2-chloro-N-{5-[4-(2-methyl-propoxy)phenyl]-1,3,4-thiadiazol-2-yl}acetamide Intermediate 18 4,5-diethyl-4H-1,2,4-triazole-3-thiol

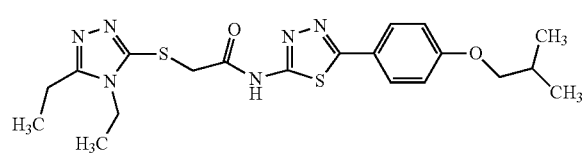 [SMILES: CCc1nnc(SCC(=O)Nc2nnc(-c3ccc(OCC(C)C)cc3)s2)n1CC]

2-[(diethyl-4H-1,2,4-triazol-3-yl)sulfanyl]-N-{5-[4-(2-methyl propoxy)phenyl]-1,3,4-thiadiazol-2-yl}acetamide Yield: 20 mg LC-MS (ES): 447.2 (M+H), $^1$H NMR (400 MHz, DMSO-$d_6$) δ 7.85 (d, 2H), 7.07 (d, 2H), 4.22 (s, 2H), 3.93 (q, 2H), 3.82 (d, 2H), 2.71 (q, 2H), 2.04 (heptet, 1H), 1.23 (t, 6H), 0.99 (d, 6H).

Example 14

Example 14 was prepared from intermediate 27 and 18 in a manner analogous to example 10

Intermediate 27 2-chloro-N-[5-(4-ethylphenyl)-1,3,4-thiadiazol-2-yl]acetamide

Intermediate 18 4,5-diethyl-4H-1,2,4-triazole-3-thiol

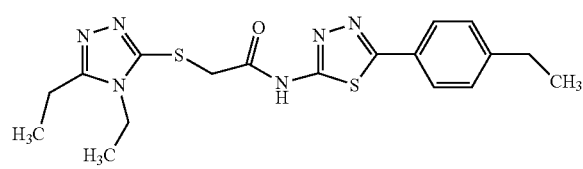 [SMILES: CCc1ccc(-c2nnc(NC(=O)CSc3nnc(CC)n3CC)s2)cc1]

2-[(diethyl-4H-1,2,4-triazol-3-yl)sulfanyl]-N-[5-(4-ethylphenyl)-1,3,4-thiadiazol-2-yl]acetamide Yield: 45 mg LC-MS (ES): 403.2 (M+H), $^1$H NMR (400 MHz, DMSO-$d_6$) δ 12.94 (s, 1H), 7.84 (d, 2H), 7.37 (d, 2H), 4.23 (s, 2H), 3.93 (q, 2H), 2.75-2.63 (m, 4H), 1.27-1.17 (m, 9H).

Example 15

Example 15 was prepared from intermediate 28 and 18 in a manner analogous to example 10

Intermediate 28 2-chloro-N-[5-(4-propylphenyl)-1,3,4-thiadiazol-2-yl]acetamide

Intermediate 18 4,5-diethyl-4H-1,2,4-triazole-3-thiol

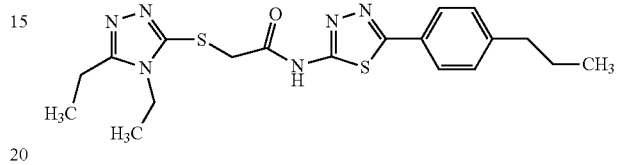

2-[(diethyl-4H-1,2,4-triazol-3-yl)sulfanyl]-N-[5-(4-propylphenyl)-1,3,4-thiadiazol-2-yl]acetamide Yield: 40 mg LC-MS (ES): 417.2 (M+H), $^1$H NMR (400 MHz, DMSO-$d_6$) δ 12.94 (s, 1H), 7.84 (d, 2H), 7.34 (d, 2H), 4.23 (s, 2H), 3.93 (q, 2H), 2.71 (q, 2H), 2.61 (t, 2H), 1.62 (h, 2H), 1.23 (t, 6H), 0.90 (t, 3H).

Example 16

Example 16 was prepared from intermediate 29 and 18 in a manner analogous to example 10

Intermediate 29 2-chloro-N-[5-(4-butylphenyl)-1,3,4-thiadiazol-2-yl]acetamide

Intermediate 18 4,5-diethyl-4H-1,2,4-triazole-3-thiol

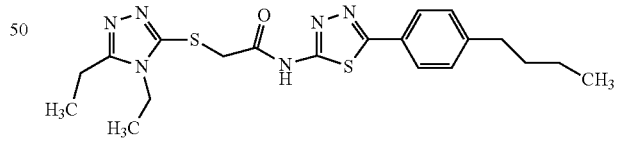

2-[(diethyl-4H-1,2,4-triazol-3-yl)sulfanyl]-N-[5-(4-butylphenyl)-1,3,4-thiadiazol-2-yl]acetamide Yield: 35 mg LC-MS (ES): 431.2 (M+H), $^1$H NMR (400 MHz, DMSO-$d_6$) δ 12.93 (s, OH), 7.83 (d, 2H), 7.34 (d, 2H), 4.23 (s, 2H), 3.93 (q, 2H), 2.75-2.60 (m, 4H), 1.58 (p, 2H), 1.31 (p, 2H), 1.23 (t, 6H), 0.90 (t, 3H).

Example 17

Example 17 was prepared from intermediate 30 and 18 in a manner analogous to example 10

Intermediate 30 2-chloro-N-(5-phenyl-1,3,4-thiadiazol-2-yl)acetamide

Intermediate 18 4,5-diethyl-4H-1,2,4-triazole-3-thiol

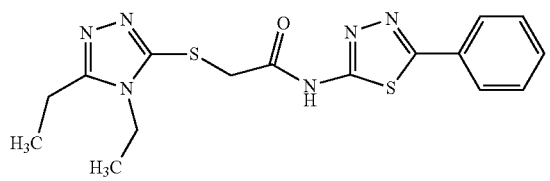 [SMILES: CCc1nnc(SCC(=O)Nc2nnc(-c3ccccc3)s2)n1CC]

2-[(diethyl-4H-1,2,4-triazol-3-yl)sulfanyl]-N-(5-phenyl-1,3,4-thiadiazol-2-yl)acetamide Yield: 25 mg LC-MS (ES): 375.1 (M+H), $^1$H NMR (400 MHz, DMSO-$d_6$) δ 12.98 (s, 1H), 7.98-7.89 (m, 2H), 7.56-7.51 (m, 3H), 4.24 (s, 2H), 3.93 (q, 2H), 2.70 (q, 2H), 1.23 (t, 6H).

Example 18

Example 18 was prepared from intermediate 31 and 18 in a manner analogous to example 10

Intermediate 31 2-chloro-N-[5-(2,3-dihydro-1-benzofuran-5-yl)-1,3,4-thiadiazol-2-yl]acetamide Intermediate 18 4,5-diethyl-4H-1,2,4-triazole-3-thiol

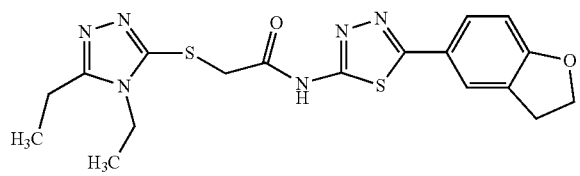 [SMILES: CCc1nnc(SCC(=O)Nc2nnc(-c3ccc4c(c3)CCO4)s2)n1CC]

2-[(diethyl-4H-1,2,4-triazol-3-yl)sulfanyl]-N-[5-(2,3-dihydro-1-benzofuran-5-yl)-1,3,4-thiadiazol-2-yl]acetamide Yield: 50 mg LC-MS (ES): 417.1 (M+H), $^1$H NMR (400 MHz, DMSO-$d_6$) δ 12.85 (s, 1H), 7.81 (s, 1H), 7.67 (d, 1H), 6.88 (d, 1H), 4.61 (t, 2H), 4.22 (s, 2H), 3.93 (q, 2H), 3.25 (t, 2H), 2.71 (q, 2H), 1.23 (t, 6H).

Example 19

Example 19 was prepared from intermediate 32 and 18 in a manner analogous to example 10

Intermediate 32 2-chloro-N-{5-[4-(2-methylpropyl)phenyl]-1,3,4-thiadiazol-2-yl}acetamide Intermediate 18 4,5-diethyl-4H-1,2,4-triazole-3-thiol

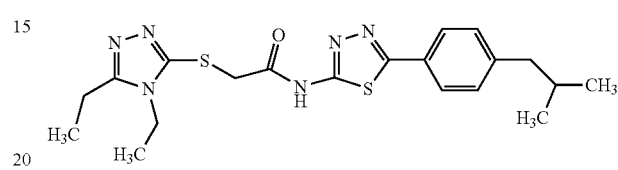

2-[(diethyl-4H-1,2,4-triazol-3-yl)sulfanyl]-N-{5-[4-(2-methylpropyl)phenyl]-1,3,4-thiadiazol-2-yl}acetamide Yield: 32 mg LC-MS (ES): 431.2 (M+H), $^1$H NMR (400 MHz, DMSO-$d_6$) δ 12.94 (s, 1H), 7.84 (d, 2H), 7.31 (d, 2H), 4.23 (s, 2H), 3.93 (q, 2H), 2.71 (q, 2H), 2.52 (d, 2H), 1.87 (hept, 1H), 1.23 (t, 6H), 0.88 (d, 6H).

Example 20

Example 20 was prepared from intermediate 33 and 18 in a manner analogous to example 10

Intermediate 33 2-chloro-N-{5-[4-(propan-2-yl)phenyl]-1,3,4-thiadiazol-2-yl}acetamide Intermediate 18 4,5-diethyl-4H-1,2,4-triazole-3-thiol

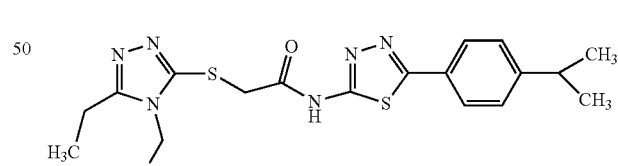

2-[(diethyl-4H-1,2,4-triazol-3-yl)sulfanyl]-N-{5-[4-(propan-2-yl)phenyl]-1,3,4-thiadiazol-2-yl}acetamide Yield: 43 mg LC-MS (ES): 417.2 (M+H), $^1$H NMR (400 MHz, DMSO-$d_6$) δ 12.94 (s, 1H), 7.85 (d, 2H), 7.40 (d, 2H), 4.23 (s, 2H), 3.93 (q, 2H), 2.95 (m, 1H), 2.71 (q, 2H), 1.24 (t, 12H).

Example 21

Example 21 was prepared from intermediate 34 and 18 in a manner analogous to example 10

Intermediate 34 2-chloro-N-[5-(4-hydroxyphenyl)-1,3,4-thiadiazol-2-yl]acetamide

Intermediate 18 4,5-diethyl-4H-1,2,4-triazole-3-thiol

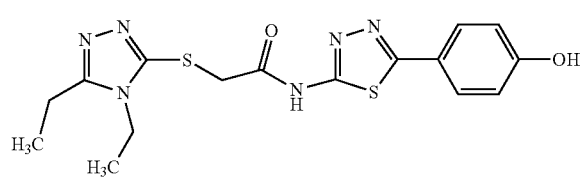 [SMILES: CCc1nnc(SCC(=O)Nc2nnc(-c3ccc(O)cc3)s2)n1CC]

2-[(diethyl-4H-1,2,4-triazol-3-yl)sulfanyl]-N-[5-(4-hydroxyphenyl)-1,3,4-thiadiazol-2-yl]acetamide Yield: 43 mg LC-MS (ES): 391.1 (M+H), $^1$H NMR (400 MHz, DMSO-$d_6$) δ 12.84 (s, 1H), 10.07 (s, 1H), 7.75 (d, 2H), 6.88 (d, 2H), 4.22 (s, 2H), 3.93 (q, 2H), 2.75-2.67 (m, 2H), 1.23 (t, 6H).

Example 22

Example 22 was prepared from intermediate 30 and 4 in a manner analogous to example 10

Intermediate 30 2-chloro-N-(5-phenyl-1,3,4-thiadiazol-2-yl)acetamide

Intermediate 4 4-ethyl-5-(2-methoxyethyl)-1,2,4-triazolidine-3-thiol

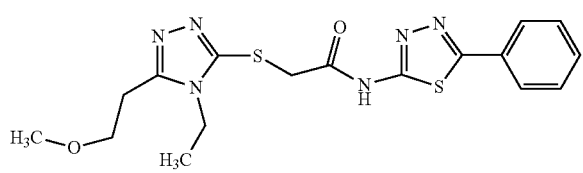 [SMILES: CCn1c(CCOC)nnc1SCC(=O)Nc1nnc(-c2ccccc2)s1]

2-{[4-ethyl-5-(2-methoxyethyl)-4H-1,2,4-triazol-3-yl]sulfanyl}-N-(5-phenyl-1,3,4-thiadiazol-2-yl)acetamide Yield: 25 mg LC-MS (ES): 405.2 (M+H), $^1$H NMR (400 MHz, DMSO-$d_6$) 512.98 (s, 1H), 7.94 (dd, 2H), 7.55-7.50 (m, 3H), 4.26 (s, 2H), 3.96 (q, 2H), 3.65 (t, 2H), 3.24 (s, 3H), 2.96 (t, 2H), 1.24 (t, 3H).

Example 23

Example 23 was prepared from intermediate 35 and 4 in a manner analogous to example 10

Intermediate 35 2-chloro-N-{5-[4-(propan-2-yloxy)phenyl]-1,3,4-thiadiazol-2-yl}acetamide Intermediate 4 4-ethyl-5-(2-methoxyethyl)-1,2,4-triazolidine-3-thiol

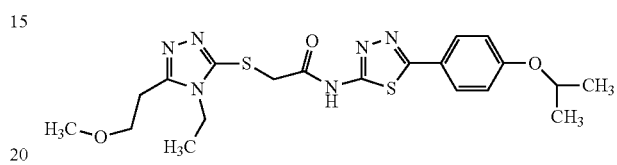

2-{[4-ethyl-5-(2-methoxyethyl)-4H-1,2,4-triazol-3-yl]sulfanyl}-N-{5-[4-(propan-2-yloxy)phenyl]-1,3,4-thiadiazol-2-yl}acetamide Yield: 35 mg LC-MS (ES): 463.2 (M+H), $^1$H NMR (400 MHz, DMSO-$d_6$) δ 12.89 (s, 1H), 7.84 (d, 2H), 7.04 (d, 2H), 4.71 (p, 1H), 4.24 (s, 2H), 3.96 (q, 2H), 3.65 (t, 2H), 3.24 (s, 3H), 2.96 (t, 2H), 1.29 (d, 6H), 1.23 (t, 3H).

Example 24

Example 24 was prepared from intermediate 28 and 4 in a manner analogous to example 10

Intermediate 28 2-chloro-N-[5-(4-propylphenyl)-1,3,4-thiadiazol-2-yl]acetamide

Intermediate 4 4-ethyl-5-(2-methoxyethyl)-1,2,4-triazolidine-3-thiol

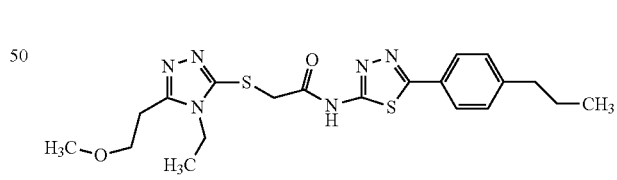

2-{[4-ethyl-5-(2-methoxyethyl)-4H-1,2,4-triazol-3-yl]sulfanyl}-N-[5-(4-propylphenyl)-1,3,4-thiadiazol-2-yl]acetamide Yield: 27 mg LC-MS (ES): 447.2 (M+H), $^1$H NMR (400 MHz, DMSO-$d_6$) δ 12.95 (s, 1H), 7.84 (d, 2H), 7.35 (d, 2H), 4.25 (s, 2H), 3.96 (q, 2H), 3.65 (t, 2H), 3.24 (s, 3H), 2.96 (t, 2H), 2.61 (t, 2H), 1.62 (h, 2H), 1.23 (t, 3H), 0.91 (t, 3H).

Example 25

Example 25 was prepared from intermediate 36 and 18 in a manner analogous to example 10

Intermediate 36 2-chloro-N-[5-(4-ethoxyphenyl)-1,3,4-thiadiazol-2-yl]acetamide

Intermediate 18 4,5-diethyl-4H-1,2,4-triazole-3-thiol

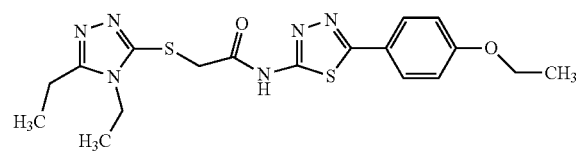

2-[(diethyl-4H-1,2,4-triazol-3-yl)sulfanyl]-N-[5-(4-ethoxyphenyl)-1,3,4-thiadiazol-2-yl]acetamide Yield: 50 mg LC-MS (ES): 419.2 (M+H), $^1$H NMR (400 MHz, DMSO-$d_6$) δ 12.89 (s, 1H), 7.85 (d, 2H), 7.06 (d, 2H), 4.22 (s, 2H), 4.10 (q, 2H), 3.93 (q, 2H), 2.71 (q, 2H), 1.35 (t, 3H), 1.23 (t, 6H).

Example 26

Example 26 was prepared from intermediate 37 and 18 in a manner analogous to example 10

Intermediate 37 2-chloro-N-{5-[4-(2-fluoroethoxy)phenyl]-1,3,4-thiadiazol-2-yl}acetamide Intermediate 18 4,5-diethyl-4H-1,2,4-triazole-3-thiol

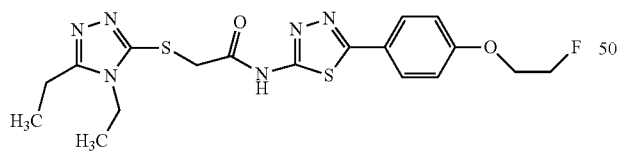

2-[(diethyl-4H-1,2,4-triazol-3-yl)sulfanyl]-N-{5-[4-(2-fluoroethoxy)phenyl]-1,3,4-thiadiazol-2-yl}acetamide Yield: 50 mg LC-MS (ES): 437.2 (M+H), $^1$H NMR (400 MHz, DMSO-$d_6$) δ 12.90 (s, 1H), 7.88 (d, 2H), 7.11 (d, 2H), 4.86-4.79 (m, 1H), 4.74-4.67 (m, 1H), 4.39-4.33 (m, 1H), 4.32-4.25 (m, 1H), 4.22 (s, 2H), 3.93 (q, 2H), 2.71 (q, 2H), 1.23 (t, 6H).

Example 27

Example 27 was prepared from intermediate 36 and 15 in a manner analogous to example 10

Intermediate 36 2-chloro-N-[5-(4-ethoxyphenyl)-1,3,4-thiadiazol-2-yl]acetamide

Intermediate 15 4-ethyl-5-(propan-2-yl)-4H-1,2,4-triazole-3-thiol

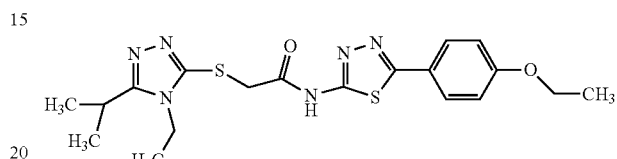

N-[5-(4-ethoxyphenyl)-1,3,4-thiadiazol-2-yl]-2-{[4-ethyl-5-(propan-2-yl)-4H-1,2,4-triazol-3-yl]sulfanyl}acetamide Yield: 60 mg LC-MS (ES): 433.2 (M+H), $^1$H NMR (400 MHz, DMSO-$d_6$) δ 12.89 (s, 1H), 7.85 (d, 2H), 7.06 (d, 2H), 4.24 (s, 2H), 4.10 (q, 2H), 3.95 (q, 2H), 3.07 (h, 1H), 1.35 (t, 3H), 1.24 (m, 9H).

Example 28

Example 28 was prepared from intermediate 37 and 15 in a manner analogous to example 10

Intermediate 37 2-chloro-N-{5-[4-(2-fluoroethoxy)phenyl]-1,3,4-thiadiazol-2-yl}acetamide Intermediate 15 4-ethyl-5-(propan-2-yl)-4H-1,2,4-triazole-3-thiol

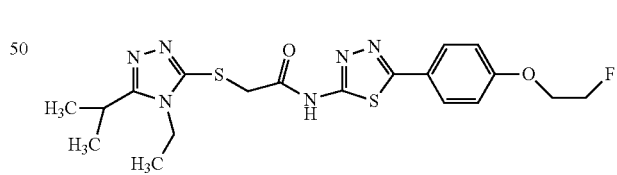

2-{[4-ethyl-5-(propan-2-yl)-4H-1,2,4-triazol-3-yl]sulfanyl}-N-{5-[4-(2-fluoroethoxy)phenyl]-1,3,4-thiadiazol-2-yl}acetamide Yield: 40 mg LC-MS (ES): 451.2 (M+H), $^1$H NMR (400 MHz, DMSO-$d_6$) δ 12.91 (s, 1H), 7.88 (d, 2H), 7.11 (d, 2H), 4.86-4.79 (m, 1H), 4.74-4.67 (m, 1H), 4.39-4.33 (m, 1H), 4.32-4.25 (m, 1H), 4.24 (s, 2H), 3.95 (q, 2H), 3.07 (hept, 1H), 1.24 (m, 9H)

Example 29

Example 29 was prepared from intermediate 35 and 15 in a manner analogous to example 10

Intermediate 35 2-chloro-N-{5-[4-(propan-2-yloxy)phenyl]-1,3,4-thiadiazol-2-yl}acetamide Intermediate 15 4-ethyl-5-(propan-2-yl)-4H-1,2,4-triazole-3-thiol

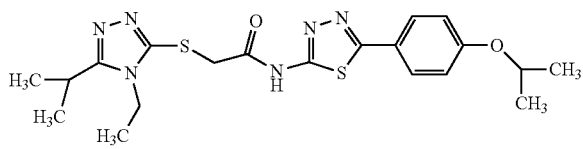

2-{[4-ethyl-5-(propan-2-yl)-4H-1,2,4-triazol-3-yl]sulfanyl}-N-{5-[4-(propan-2-yloxy)phenyl]-1,3,4-thiadiazol-2-yl}acetamide Yield: 40 mg LC-MS (ES): 447.2 (M+H), $^1$H NMR (400 MHz, DMSO-$d_6$) δ 12.88 (s, 1H), 7.84 (d, 2H), 7.04 (d, 2H), 4.71 (hept, 1H), 4.24 (s, 2H), 4.00-3.90 (q, 2H), 3.07 (hept, 1H), 1.27 (m, 15H).

Example 30

Example 30 was prepared from intermediate 38 and 18 in a manner analogous to example 10

Intermediate 38 2-chloro-N-{5-[4-(2-methoxyethoxy)phenyl]-1,3,4-thiadiazol-2-yl}acetamide Intermediate 18 4,5-diethyl-4H-1,2,4-triazole-3-thiol

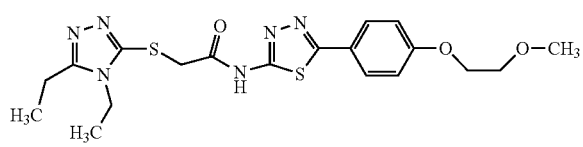 [SMILES: CCc1nnc(SCC(=O)Nc2nnc(-c3ccc(OCCOC)cc3)s2)n1CC]

2-[(diethyl-4H-1,2,4-triazol-3-yl)sulfanyl]-N-{5-[4-(2-methoxyethoxy)phenyl]-1,3,4-thiadiazol-2-yl}acetamide Yield: 24 mg LC-MS (ES): 449.2 (M+H), $^1$H NMR (400 MHz, DMSO-$d_6$) δ 12.89 (s, 1H), 7.86 (d, 2H), 7.08 (d, 2H), 4.22 (s, 2H), 4.17 (m, 2H), 3.93 (q, 2H), 3.68 (m, 2H), 2.71 (q, 2H), 1.23 (t, 6H).

Example 31

Example 31 was prepared from intermediate 38 and 15 in a manner analogous to example 10

Intermediate 38 2-chloro-N-{5-[4-(2-methoxyethoxy)phenyl]-1,3,4-thiadiazol-2-yl}acetamide Intermediate 15 4-ethyl-5-(propan-2-yl)-4H-1,2,4-triazole-3-thiol

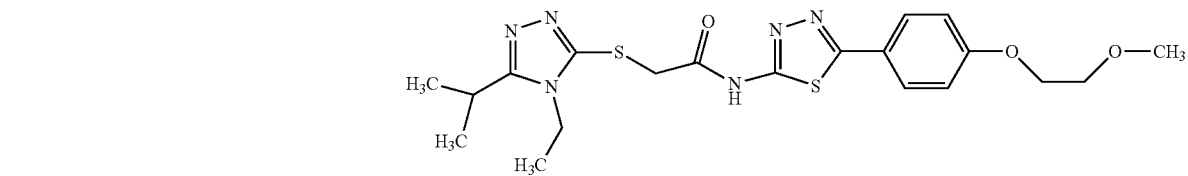 [SMILES: CCn1c(SCC(=O)Nc2nnc(-c3ccc(OCCOC)cc3)s2)nnc1C(C)C]

2-{[4-ethyl-5-(propan-2-yl)-4H-1,2,4-triazol-3-yl]sulfanyl}-N-{5-[4-(2-methoxyethoxy) phenyl]-1,3,4-thiadiazol-2-yl}acetamide Yield: 15 mg LC-MS (ES): 463.2 (M+H), $^1$H NMR (400 MHz, DMSO-$d_6$) δ 12.89 (s, 1H), 7.86 (d, 2H), 7.08 (d, 2H), 4.24 (s, 2H), 4.22-4.15 (m, 2H), 3.95 (q, 2H), 3.70-3.66 (m, 2H), 3.07 (p, 1H), 1.24 (m, 9H).

Example 32

N-[5-(4-cyanophenyl)-1,3,4-thiadiazol-2-yl]-2-[(4,5-diethyl-4H-1,2,4-triazol-3-yl)sulfanyl]acetamide To a suspension of 2-chloro-N-(5-(4-cyanophenyl)-1,3,4-thiadiazol-2-yl)acetamide Intermediate 39 (95 mg, 0.34 mmol) in acetonitrile (4.3 mL), 4,5-diethyl-4H-1,2,4-triazole-3-thiol Intermediate 18 (54 mg, 0.34 mmol) and triethylamine (57 µL, 0.41 mmol) were added. The reaction mixture was heated under reflux for 6 hours, then cooled to room temperature. The resulting precipitate was filtered off, washed with acetonitrile and DCM to give 106 mg (78%) of the title compound.

LC-MS (ES): 400.1 (M+H), $^1$H NMR (400 MHz, DMSO-$d_6$) δ 13.15 (s, 1H), 8.16-8.11 (m, 2H), 8.01-7.97 (m, 2H), 4.26 (s, 2H), 3.93 (q, 2H), 2.72 (q, 2H), 1.24 (td, 6H).

Example 33

Example 33 was prepared from intermediate 40 and 18 in a manner analogous to example 32

Intermediate 40 2-chloro-N-(5-(4-(trifluoromethyl)phenyl)-1,3,4-thiadiazol-2-yl)acetamide Intermediate 18 4,5-diethyl-4H-1,2,4-triazole-3-thiol

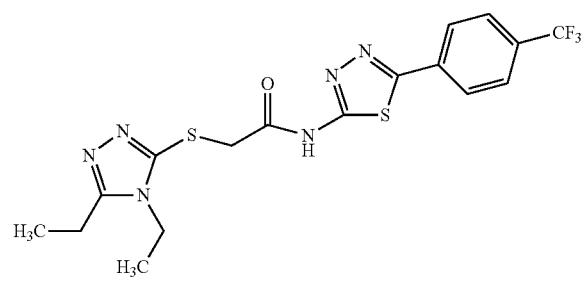 [SMILES: CCc1nnc(SCC(=O)Nc2nnc(-c3ccc(C(F)(F)F)cc3)s2)n1CC]

2-[(4,5-diethyl-4H-1,2,4-triazol-3-yl)sulfanyl]-N-[5-(4-(trifluoromethyl)phenyl)-1,3,4-thiadiazol-2-yl]acetamide LC-MS (ES): 443.1 (M+H), $^1$H NMR (400 MHz, DMSO-$d_6$) δ 13.13 (s, 1H), 8.17 (d, 2H), 7.89 (d, 2H), 4.27 (s, 2H), 3.94 (q, 2H), 2.72 (q, 2H), 1.24 (td, 6H).

Example 34

Example 34 was prepared from intermediate 35 and 18 in a manner analogous to example 32

Intermediate 35 2-chloro-N-(5-(4-isopropoxyphenyl)-1,3,4-thiadiazol-2-yl)acetamide Intermediate 18 4,5-diethyl-4H-1,2,4-triazole-3-thiol

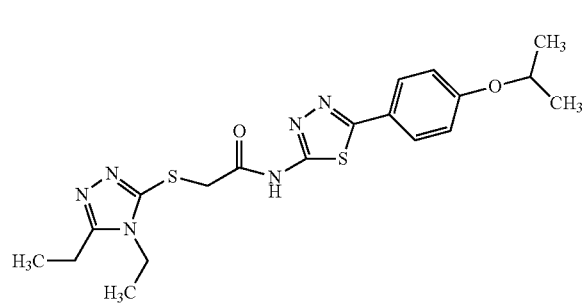 [SMILES: CCc1nnc(SCC(=O)Nc2nnc(-c3ccc(OC(C)C)cc3)s2)n1CC]

2-[(4,5-diethyl-4H-1,2,4-triazol-3-yl)sulfanyl]-N-[5-(4-isopropoxyphenyl)-1,3,4-thiadiazol-2-yl]acetamide LC-MS (ES): 433.2 (M+H), $^1$H NMR (400 MHz, DMSO-$d_6$) δ 12.90 (s, 1H), 7.89-7.81 (m, 2H), 7.09-7.00 (m, 2H), 4.71 (m, 1H), 4.24 (s, 2H), 3.93 (q, 2H), 2.72 (q, 2H), 1.30 (d, 6H), 1.27-1.20 (m, 6H).

Example 35

Example 35 was prepared from intermediate 41 and 18 in a manner analogous to example 32

Intermediate 41 2-chloro-N-(5-(4-chlorophenyl)-1,3,4-thiadiazol-2-yl)acetamide

Intermediate 18 4,5-diethyl-4H-1,2,4-triazole-3-thiol

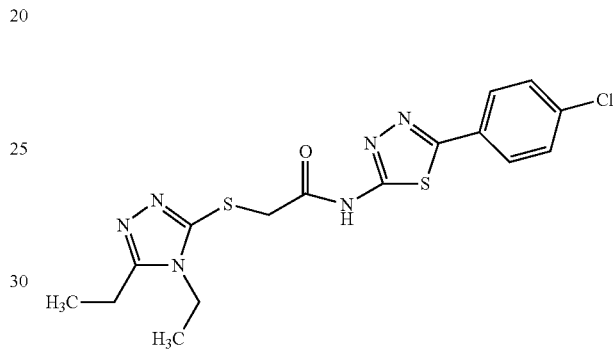

N-[5-(4-chlorophenyl)-1,3,4-thiadiazol-2-yl]-2-[(4,5-diethyl-4H-1,2,4-triazol-3-yl)sulfanyl]acetamide LC-MS (ES): 409.1 (M+H), $^1$H NMR (400 MHz, DMSO-$d_6$) δ 13.04 (s, 1H), 8.00-7.94 (m, 2H), 7.62-7.57 (m, 2H), 4.25 (s, 2H), 3.93 (q, 2H), 2.72 (q, 2H), 1.24 (td, 6H).

Example 36

Example 36 was prepared from intermediate 20 and 6 in a manner analogous to example 32

Intermediate 20 2-chloro-N-(5-(4-methoxyphenyl)-1,3,4-thiadiazol-2-yl)acetamide

Intermediate 6 4-cyclopropyl-5-ethyl-4H-1,2,4-triazole-3-thiol

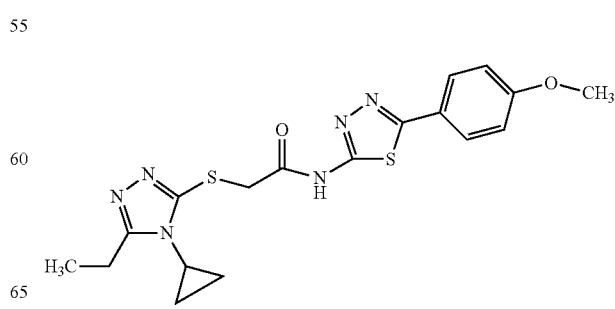

2-[(4-cyclopropyl-5-ethyl-4H-1,2,4-triazol-3-yl)sulfanyl]-N-[5-(4-methoxyphenyl)-1,3,4-thiadiazol-2-yl]acetamide LC-MS (ES): 417.2 (M+H), $^1$H NMR (400 MHz, DMSO-$d_6$) δ 12.93 (s, 1H), 7.91-7.83 (m, 2H), 7.13-7.03 (m, 2H), 4.31 (s, 2H), 3.83 (s, 3H), 3.14 (m, 1H), 2.76 (q, 2H), 1.25 (t, 3H), 1.14-1.05 (m, 2H), 1.02 (m, 2H).

Example 37

Example 37 was prepared from intermediate 20 and 7 in a manner analogous to example 32

Intermediate 20 2-chloro-N-(5-(4-methoxyphenyl)-1,3,4-thiadiazol-2-yl)acetamide

Intermediate 7 4-ethyl-5-(3-fluorobenzyl)-4H-1,2,4-triazole-3-thiol

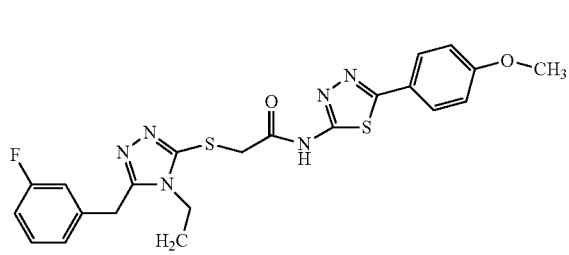 [SMILES: CCn1c(Cc2cccc(F)c2)nnc1SCC(=O)Nc1nnc(-c2ccc(OC)cc2)s1]

2-[(4-ethyl-5-(3-fluorobenzyl)-4H-1,2,4-triazol-3-yl)sulfanyl]-N-[5-(4-methoxyphenyl)-1,3,4-thiadiazol-2-yl]acetamide LC-MS (ES): 485.2 (M+H), $^1$H NMR (400 MHz, DMSO-$d_6$) δ 12.92 (s, 1H), 7.91-7.84 (m, 2H), 7.40-7.32 (m, 1H), 7.09 (td, 5H), 4.26 (s, 2H), 4.21 (s, 2H), 3.92 (q, 2H), 3.83 (s, 3H), 1.02 (t, 3H).

Example 38

Example 38 was prepared from intermediate 34 and 16 in a manner analogous to example 32

Intermediate 34 2-chloro-N-(5-(4-hydroxyphenyl)-1,3,4-thiadiazol-2-yl)acetamide

Intermediate 16 5-cyclopropyl-4-ethyl-4H-1,2,4-triazole-3-thiol

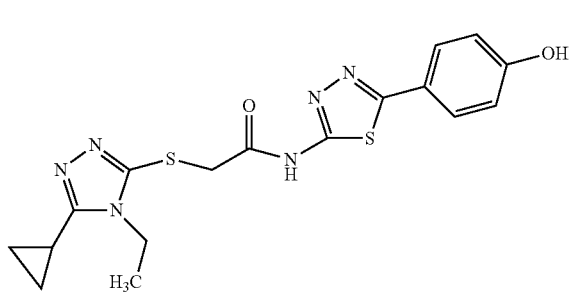 [SMILES: CCn1c(SCC(=O)Nc2nnc(-c3ccc(O)cc3)s2)nnc1C1CC1]

2-[(5-cyclopropyl-4-ethyl-4H-1,2,4-triazol-3-yl)sulfanyl]-N-[5-(4-hydroxyphenyl)-1,3,4-thiadiazol-2-yl]acetamide LC-MS (ES): 403.1 (M+H), $^1$H NMR (400 MHz, DMSO-$d_6$) δ 12.83 (s, 1H), 10.10 (s, 1H), 7.76 (d, 2H), 6.89 (d, 2H), 4.19 (s, 2H), 4.06 (q, 2H), 2.00 (m, 1H), 1.29 (t, 3H), 0.98 (m, 2H), 0.88 (m, 2H).

Example 39

Example 39 was prepared from intermediate 22 and 6 in a manner analogous to example 32

Intermediate 22 2-chloro-N-(5-(4-(methylsulfonyl)phenyl)-1,3,4-thiadiazol-2-yl)acetamide Intermediate 6 4-cyclopropyl-5-ethyl-4H-1,2,4-triazole-3-thiol

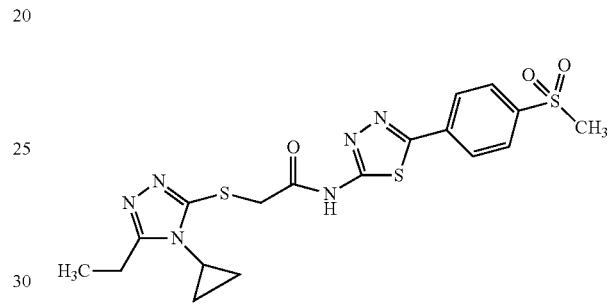

2-[(4-cyclopropyl-5-ethyl-4H-1,2,4-triazol-3-yl)sulfanyl]-N-[5-(4-(methylsulfonyl)phenyl)-1,3,4-thiadiazol-2-yl]acetamide LC-MS (ES): 451.2 (M+H), $^1$H NMR (400 MHz, DMSO-$d_6$) δ 13.17 (s, 1H), 8.22 (d, 2H), 8.06 (d, 2H), 4.34 (s, 2H), 3.29 (s, 3H), 3.14 (m, 1H), 2.76 (q, 2H), 1.24 (t, 3H), 1.17-1.06 (m, 2H), 1.06-0.95 (m, 2H)

Example 40

Example 40 was prepared from intermediate 20 and 8 in a manner analogous to example 32

Intermediate 20 2-chloro-N-(5-(4-methoxyphenyl)-1,3,4-thiadiazol-2-yl)acetamide

Intermediate 8 3-(3-ethyl-5-mercapto-4H-1,2,4-triazol-4-yl)propan-1-ol

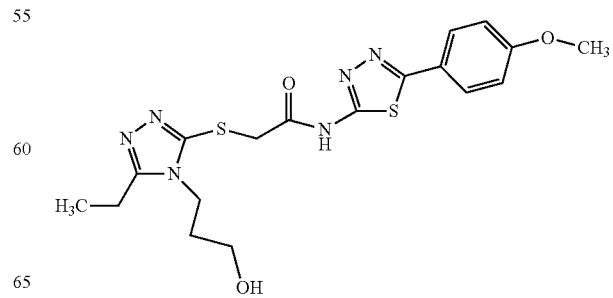

2-[(5-ethyl-4-(3-hydroxypropyl)-4H-1,2,4-triazol-3-yl)sulfanyl]-N-[5-(4-methoxyphenyl)-1,3,4-thiadiazol-2-yl]acetamide LC-MS (ES): 435.2 (M+H), $^1$H NMR (400 MHz, DMSO-$d_6$) δ 12.92 (s, 1H), 7.91-7.85 (m, 2H), 7.12-7.04 (m, 2H), 4.72 (t, 1H), 4.24 (s, 2H), 3.95 (t, 2H), 3.83 (s, 3H), 3.41 (q, 2H), 2.72 (q, 2H), 1.77 (p, 2H), 1.24 (t, 3H).

Example 41

Example 41 was prepared from intermediate 22 and 2 in a manner analogous to example 32

Intermediate 22 2-chloro-N-(5-(4-(methylsulfonyl)phenyl)-1,3,4-thiadiazol-2-yl)acetamide Intermediate 2
5-ethyl-4-methyl-4H-1,2,4-triazole-3-thiol

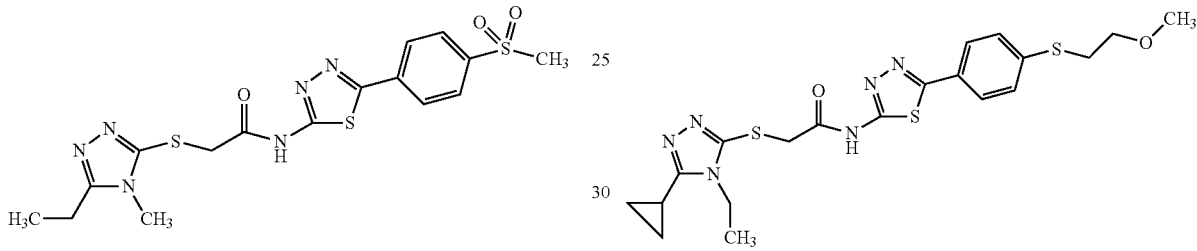

2-[(5-ethyl-4-methyl-4H-1,2,4-triazol-3-yl)sulfanyl]-N-[5-(4-(methylsulfonyl)phenyl)-1,3,4-thiadiazol-2-yl]acetamide LC-MS (ES): 439.1 (M+H), $^1$H NMR (400 MHz, DMSO-$d_6$) δ 13.13 (s, 1H), 8.26-8.16 (m, 2H), 8.10-8.04 (m, 2H), 4.20 (s, 2H), 3.50 (s, 3H), 3.29 (s, 3H), 2.70 (q, 2H), 1.21 (t, 3H).

Example 42

Example 42 was prepared from intermediate 22 and 10 in a manner analogous to example 32

Intermediate 22 2-chloro-N-(5-(4-(methylsulfonyl)phenyl)-1,3,4-thiadiazol-2-yl)acetamide Intermediate 10
5-ethyl-4-isopropyl-4H-1,2,4-triazole-3-thiol

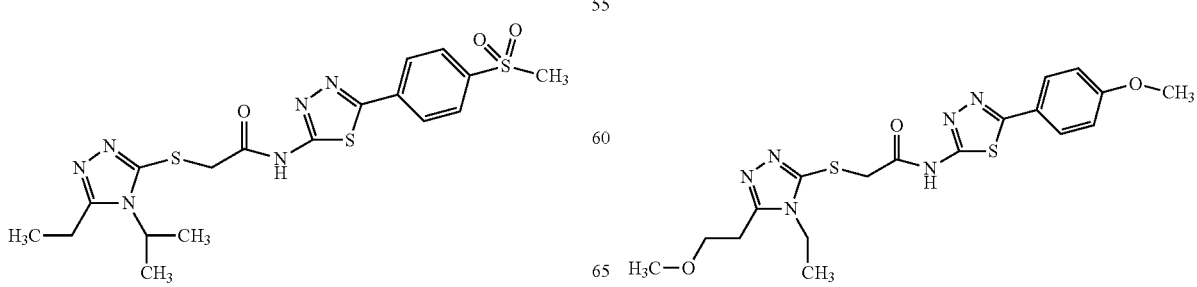

2-[(5-ethyl-4-isopropyl-4H-1,2,4-triazol-3-yl)sulfanyl]-N-[5-(4-(methylsulfonyl)phenyl)-1,3,4-thiadiazol-2-yl]acetamide LC-MS (ES): 467.2 (M+H), $^1$H NMR (400 MHz, DMSO-$d_6$) δ 13.17 (s, 1H), 8.22 (d, 2H), 8.07 (d, 2H), 4.51 (hept, 1H), 4.33 (s, 2H), 3.29 (s, 3H), 2.75 (q, 2H), 1.47 (d, 6H), 1.22 (t, 3H).

Example 43

Example 43 was prepared from intermediate 38 and 16 in a manner analogous to example 32

Intermediate 38 2-chloro-N-(5-(4-(2-methoxyethoxy)phenyl)-1,3,4-thiadiazol-2-yl)acetamide Intermediate 16
5-cyclopropyl-4-ethyl-4H-1,2,4-triazole-3-thiol

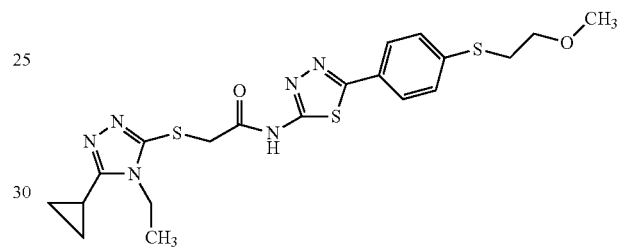

2-[(5-cyclopropyl-4-ethyl-4H-1,2,4-triazol-3-yl)sulfanyl]-N-[5-(4-(2-methoxyethoxy)phenyl)-1,3,4-thiadiazol-2-yl]acetamide LC-MS (ES): 461.2 (M+H), $^1$H NMR (400 MHz, DMSO-$d_6$) δ 12.89 (s, 1H), 7.86 (d, 2H), 7.08 (d, 2H), 4.20 (s, 2H), 4.19-4.14 (m, 2H), 4.06 (q, 2H), 3.71-3.66 (m, 2H), 3.32 (s, 3H), 2.00 (m, 1H), 1.29 (t, 3H), 0.98 (m, 2H), 0.88 (m, 2H).

Example 44

Example 44 was prepared from intermediate 20 and 4 in a manner analogous to example 32

Intermediate 20 2-chloro-N-(5-(4-methoxyphenyl)-1,3,4-thiadiazol-2-yl)acetamide

Intermediate 4 4-ethyl-5-(2-methoxyethyl)-4H-1,2,4-triazole-3-thiol

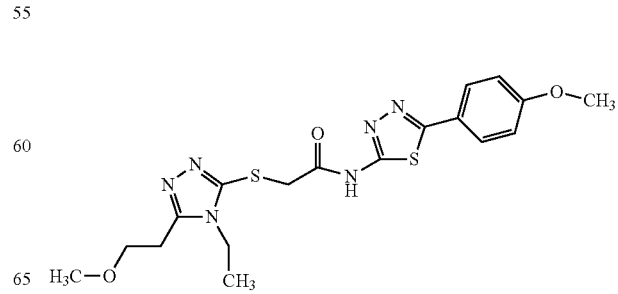

2-[(4-ethyl-5-(2-methoxyethyl)-4H-1,2,4-triazol-3-yl)sulfanyl]-N-[5-(4-methoxyphenyl)-1,3,4-thiadiazol-2-yl]acetamide LC-MS (ES): 435.2 (M+H), ¹H NMR (400 MHz, DMSO-d₆) δ 12.92 (s, 1H), 7.90-7.86 (m, 2H), 7.10-7.06 (m, 2H), 4.26 (s, 2H), 3.97 (q, 2H), 3.83 (s, 3H), 3.66 (t, 2H), 3.24 (s, 3H), 2.97 (t, 2H), 1.24 (t, 3H).

Example 45

Example 45 was prepared from intermediate 22 and 11 in a manner analogous to example 32

Intermediate 22 2-chloro-N-(5-(4-(methylsulfonyl)phenyl)-1,3,4-thiadiazol-2-yl)acetamide Intermediate 11 5-cyclopentyl-4-ethyl-4H-1,2,4-triazole-3-thiol

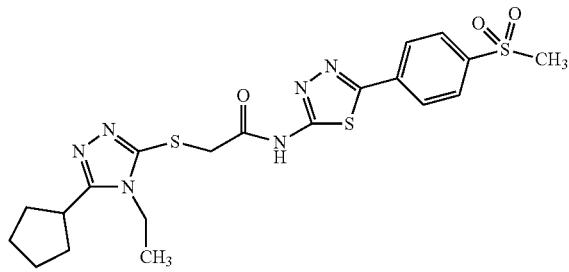 [SMILES: CCn1c(SCC(=O)Nc2nnc(-c3ccc(S(C)(=O)=O)cc3)s2)nnc1C1CCCC1]

(2-[(5-cyclopentyl-4-ethyl-4H-1,2,4-triazol-3-yl)sulfanyl]-N-[5-(4-methanesulfonylphenyl)-1,3,4-thiadiazol-2-yl]acetamide)

LC-MS (ES): 493.2 (M+H), ¹H NMR (400 MHz, DMSO-d₆) δ 13.15 (s, 1H), 8.26-8.18 (m, 2H), 8.09-8.03 (m, 2H), 4.27 (s, 2H), 3.97 (q, 2H), 3.29 (s, 3H), 3.17 (m, 1H), 2.06-1.93 (m, 2H), 1.84-1.54 (m, 6H), 1.29-1.21 (t, 3H).

Example 46

Example 46 was prepared from intermediate 20 and 12 in a manner analogous to example 32

Intermediate 20 2-chloro-N-(5-(4-methoxyphenyl)-1,3,4-thiadiazol-2-yl)acetamide

Intermediate 12 5-ethyl-4-(2-methoxyethyl)-4H-1,2,4-triazole-3-thiol

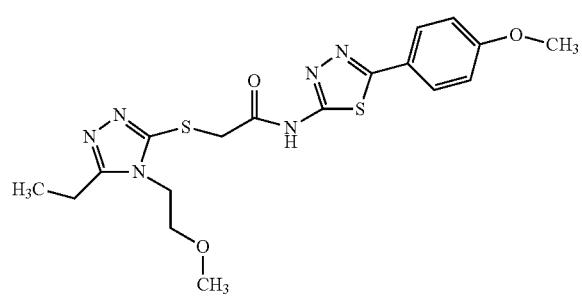 [SMILES: CCc1nnc(SCC(=O)Nc2nnc(-c3ccc(OC)cc3)s2)n1CCOC]

2-[(5-ethyl-4-(2-methoxyethyl)-4H-1,2,4-triazol-3-yl)sulfanyl]-N-[5-(4-methoxyphenyl)-1,3,4-thiadiazol-2-yl]acetamide LC-MS (ES): 435.2 (M+H), ¹H NMR (400 MHz, DMSO-d₆) δ 12.91 (s, 1H), 7.88 (d, 2H), 7.08 (d, 2H), 4.21 (s, 2H), 4.09 (t, 2H), 3.83 (s, 3H), 3.55 (t, 2H), 3.22 (s, 3H), 2.71 (q, 2H), 1.23 (t, 3H).

Example 47

Example 47 was prepared from intermediate 20 and 13 in a manner analogous to example 32

Intermediate 20 2-chloro-N-(5-(4-methoxyphenyl)-1,3,4-thiadiazol-2-yl)acetamide

Intermediate 13 5-ethyl-4-(2-methoxypropyl)-4H-1,2,4-triazole-3-thiol

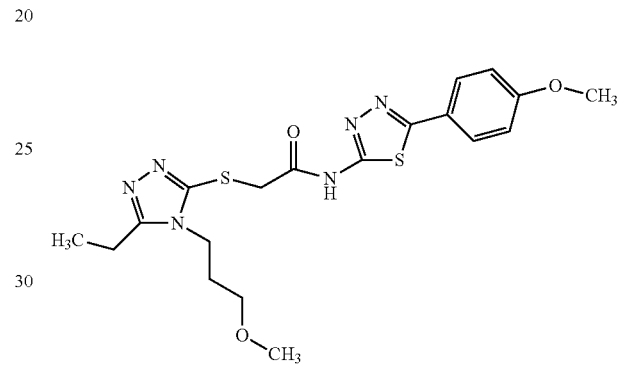

2-{[5-ethyl-4-(3-methoxypropyl)-4H-1,2,4-triazol-3-yl]sulfanyl}-N-[5-(4-methoxyphenyl)-1,3,4-thiadiazol-2-yl]acetamide LC-MS (ES): 449.2 (M+H), ¹H NMR (400 MHz, DMSO-d₆) δ 12.92 (s, 1H), 7.89-7.84 (m, 2H), 7.11-7.04 (m, 2H), 4.24 (s, 2H), 3.98-3.91 (m, 2H), 3.83 (s, 3H), 3.31 (t, 2H), 3.23 (s, 3H), 2.70 (q, 2H), 1.94-1.81 (m, 2H), 1.24 (t, 3H).

Example 48

Example 48 was prepared from intermediate 20 and 14 in a manner analogous to example 32

Intermediate 20 2-chloro-N-(5-(4-methoxyphenyl)-1,3,4-thiadiazol-2-yl)acetamide

Intermediate 14 4-ethyl-5-(morpholin-4-ylmethyl)-4H-1,2,4-triazole-3-thiol

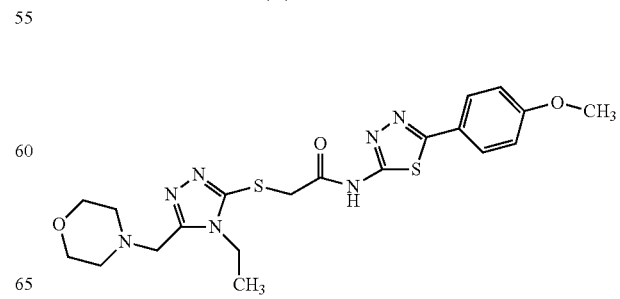

2-{[4-ethyl-5-(morpholin-4-ylmethyl)-4H-1,2,4-triazol-3-yl]sulfanyl}-N-[5-(4-methoxyphenyl)-1,3,4-thiadiazol-2-yl]acetamide LC-MS (ES): 476.2 (M+H), $^1$H NMR (400 MHz, DMSO-$d_6$) δ 12.92 (s, 1H), 7.87 (d, 1H), 7.08 (d, 2H), 4.27 (s, 2H), 4.04 (q, 2H), 3.83 (s, 3H), 3.64 (s, 2H), 3.53 (t, 4H), 2.36 (t, 4H), 1.31 (t, 3H).

Example 49

Example 49 was prepared from intermediate 42 and 18 in a manner analogous to example 32

Intermediate 42 2-chloro-N-[5-(pyridin-2-yl)-1,3,4-thiadiazol-2-yl]acetamide

Intermediate 18 4,5-diethyl-4H-1,2,4-triazole-3-thiol

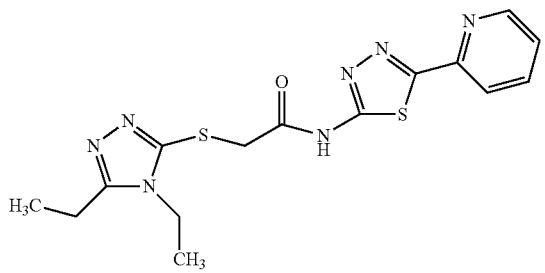 [SMILES: CCc1nnc(SCC(=O)Nc2nnc(-c3ccccn3)s2)n1CC]

2-[(4,5-diethyl-4H-1,2,4-triazol-3-yl)sulfanyl]-N-[5-(pyridin-2-yl)-1,3,4-thiadiazol-2-yl]acetamide LC-MS (ES): 376.1 (M+H), $^1$H NMR (400 MHz, DMSO-$d_6$) δ 13.03 (s, 1H), 8.67 (d, 1H), 8.21 (d, 1H), 8.00 (td, 1H), 7.53 (dd, 1H), 4.26 (s, 2H), 3.94 (q, 2H), 2.72 (q, 2H), 1.24 (td, 6H).

Biological Evaluation
Calcein Quenching Fluostar Assay

A calcein quenching fluostar assay was performed in order to investigate the biological activity of the newly synthesized examples 1 to 57. This type of assay is disclosed in *J. Biol. Chem.*, 2011, 286, 44319-44325 and *Am. J. Physiol. Renal Physiol.* (2010), 298, F224-230.

The buffers used in the assay were prepared with the following compounds and quantities.

500 ml of 4× buffer:
3.2 mM $MgSO_4.7H_2O$ (0.395 g)
20 mM KCl (0.746 g)
7.2 mM $CaCl_2.2H_2O$ (0.530 g)
100 mM NaHepes (13.02 g)
pH 7.4 w. HCl
Tetracyclin Stock:

|  | Wash buffer (μl) | Sucrose buffer (μl) |
|---|---|---|
| 4× buffer | 80000 | 35000 |
| NaCl (1M) | 34080 | 14910 |
| $H_2O$ | 199520 | 18970 |
| Probenecid | 6400 | 2800 |
| Sucrose (1M) | 0 | 68320 |
| Total | 320000 | 140000 |

The total probenecid required to prepare the wash buffer and sucrose buffer is 6400+2800=9200 μl. An additional 500 μl of probenecid (5 plates at 100 μl each) is also required. Therefore, the total probenecid required is 9200 μl+500 μl=9700 μl. Sufficient probenecid is prepared using:
690 mg probenecid;
4850 μl NaOH 1M;
1213 μl 4× buffer; and
3638 μl $H_2O$.

Assay Experimental Protocol:

1) Two days prior to commencement of the assay, seed 10,000 cells/well of 96 well black clear bottom plate (Greiner Poly-lysin plate). A 1:1 mix of Dulbecco's Modified Eagle's Medium: Nutrient Mixture F-12 (DMEM: F12) was obtained from Gibco. Tetracycline stock of 5 mg/ml in 96% ethanol is used. Medium: DMEM/F12/10% Donor Bovine Serum, Human AQP9 cell line+1:270,000 tetracyclin, mouse AQP9 cell line+1:2,700,000 tetracycline.

2) Day of assay: Flick/slam off the medium and add 50 μl/well of loading solution: 5 ml DMEM/F12/10% Donor Bovine Serum, 25 μl Calcein AM—from freshly dissolved aliquot in 50 μl DMSO (VWR #734-1434), and 100 μl Probenecid.

3) Incubate the well for 90 minutes at 37° C.
4) Perform one wash with 75 μl wash buffer.
5) Add 75 μl of an example compound prepared in wash buffer per well.

Example compounds are prepared in 500 μl U bottom PP plates (NUNC). 2.7 μl Substance in DMSO are added to row A; 180 μl of wash buffer+1% DMSO are added to rows B—H. 90 μl from row A are transferred and mixed with all other wells (up to row G) to make a 3-fold dilution series.

6) Assay in FLUOstar Optima at 25° C. Settings buffer addition at 135 μl/seconds, add 75 μl/well, record time course for 30 seconds, add sucrose buffer 3.6 seconds into recording.

7) Normalization to initial in Excel.
8) Fit to "exponential decay" function in GraphPad Prism 5.0, then arrange half live shrinking values according to wells and fit dose-response curves.

The assay results displayed in Table 1 below.

TABLE 1

$EC_{50}$ (nM) and $pEC_{50}$ (nM) values of examples1 to 49 in the inhibition of human aquaporin 9. The example compounds were used as 1 mM stock solutions in DMSO as described above.

| Compound according to Example # | $EC_{50}$ (nM) | $pEC_{50}$ (nM) |
|---|---|---|
| 1 | 173 | 6.8 |
| 2 | 59 | 7.2 |
| 3 | 195 | 6.7 |
| 4 | 175 | 6.8 |
| 5 | 455 | 6.3 |
| 6 | 192 | 6.7 |
| 7 | 105 | 7.0 |
| 8 | 66 | 7.2 |
| 9 | 87 | 7.1 |
| 10 | 101 | 7.0 |
| 11 | 394 | 6.4 |
| 12 | 57 | 7.2 |
| 13 | 101 | 7.0 |
| 14 | 65 | 7.2 |
| 15 | 57 | 7.2 |
| 16 | 179 | 6.7 |
| 17 | 127 | 6.9 |
| 18 | 124 | 6.9 |
| 19 | 94 | 7.0 |

TABLE 1-continued

EC$_{50}$ (nM) and pEC$_{50}$ (nM) values of examples1 to 49 in the inhibition of human aquaporin 9. The example compounds were used as 1 mM stock solutions in DMSO as described above.

| Compound according to Example # | EC$_{50}$ (nM) | pEC$_{50}$ (nM) |
|---|---|---|
| 20 | 79 | 7.1 |
| 21 | 224 | 7.2 |
| 22 | 249 | 6.1 |
| 23 | 39 | 7.4 |
| 24 | 41 | 7.4 |
| 25 | 42 | 7.4 |
| 26 | 43 | 7.4 |
| 27 | 69 | 7.2 |
| 28 | 44 | 7.4 |
| 29 | 90 | 7.0 |
| 30 | 21 | 7.7 |
| 31 | 37 | 7.4 |
| 32 | 43 | 7.4 |
| 33 | 119 | 6.9 |
| 34 | 55 | 7.3 |
| 35 | 54 | 7.3 |
| 36 | 51 | 7.3 |
| 37 | 132 | 6.9 |
| 38 | 81 | 7.1 |
| 39 | 135 | 6.9 |
| 40 | 168 | 6.8 |
| 41 | 490 | 6.3 |
| 42 | 76 | 7.1 |
| 43 | 52 | 7.3 |
| 44 | 457 | 7.4 |
| 45 | 40 | 7.0 |
| 46 | 112 | 6.8 |
| 47 | 159 | 6.6 |
| 48 | 230 | 6.6 |
| 49 | 224 | 6.8 |

In summary, compounds of the present invention have been found to display a high level of human aquaporin 9 inhibition. The compounds of the present invention are thus deemed to be highly useful in the treatment of diseases influence by aquaporin modulation, in particular diabetes and rheumatoid arthritis.

The invention claimed is:

1. A compound according to Formula (I), wherein Formula (I) is:

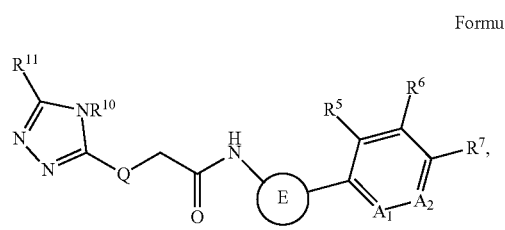

Formula (I)

or a pharmaceutically acceptable salt or stereoisomer thereof, wherein

Q is S, —CH$_2$—, or O;

E is a 5-membered heteroaryl or a 6-membered heteroaryl, wherein E is selected from the group consisting of:

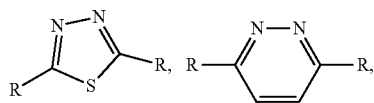

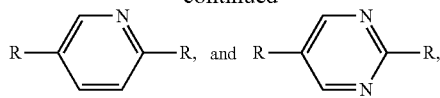

wherein R denotes the attachment points to the rest of the molecule;

A$_1$ and A$_2$ are independently selected from the group consisting of CH, CR$^2$ and N;

R$^2$ is selected from the group consisting of H, F, Cl, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy;

R$^5$ is selected from the group consisting of H, F, Cl, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy;

R$^6$ is selected from the group consisting of H, F, Cl, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy;

R$^7$ is selected from the group consisting of H, halogen, CF$_3$, CN, OH, C$_1$-C$_6$ alkyl, C$_3$-C$_6$ cycloalkyloxy, C$_3$-C$_6$ cycloalkyl, C$_1$-C$_6$ alkyloxy, O(CH$_2$)$_m$O(CH$_2$)$_n$CH$_3$, O(CH$_2$)$_m$N(R$^{4a}$)(R$^{4b}$), C(O)N(R$^{4a}$)(R$^{4b}$), SR$^{4a}$, S(O)$_2$N(R$^{4a}$)(R$^{4b}$), S(O$_2$)(R$^{4a}$), S(O)(N R$^{4a}$)(R$^{4b}$), O(CH$_2$)$_n$—heterocycloalkyl, OSO$_2$CH$_3$ and halogenated alkyl or alkoxy;

m is an integer selected from the group consisting of 1, 2, and 3;

n is an integer selected from the group consisting of 0, 1, and 2;

R$^{4a}$ and R$^{4b}$ are independently selected from the group consisting of H, C$_1$-C$_6$ alkyl, and C$_3$-C$_6$ cycloalkyl;

R$^{10}$ is selected from the group consisting of C$_1$-C$_6$ alkyl, C$_1$-C$_6$ alkylene-aryl, C$_1$-C$_6$ alkylene-OR$^{12a}$, C$_1$-C$_6$ alkylene-N(R$^{12a}$)(R$^{12b}$), C$_1$-C$_6$ alkylene-C(O)N(R$^{12a}$)(R$^{12b}$), C$_1$-C$_6$ alkylene-C(O)OR$^{12a}$, C$_1$-C$_3$ alkylene-C$_3$-C$_6$ cycloalkyl, C$_1$-C$_3$ alkylene-C$_3$-C$_6$ heterocycloalkyl, C$_3$-C$_5$ cycloalkyl, and aryl or heteroaryl, the aryl or heteroaryl optionally substituted with at least one group selected from the group consisting of halogen, CF$_3$, CN, OH, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy;

R$^{11}$ is selected from the group consisting of C$_1$-C$_6$ alkyl, C$_1$-C$_6$ alkylene-aryl, C$_3$-C$_6$ cycloalkyl, C$_1$-C$_3$ alkylene-C$_3$-C$_6$ heterocycloalkyl, C$_1$-C$_6$ alkylene-OR$^{12a}$, and aryl or heteroaryl, the aryl or heteroaryl optionally substituted with at least one group selected from the group consisting of halogen, CF$_3$, CN, OH, C$_1$-C$_6$ alkyl, C$_1$-C$_3$ alkylene-C$_3$-C$_6$ cycloalkyl, C$_3$-C$_6$ cycloalkyl, and C$_1$-C$_6$ alkyloxy;

R$^{12a}$ and R$^{12b}$ are independently selected from the group consisting of H, C$_1$-C$_4$ alkyl, and cyclopropyl, with the proviso that when Q is S and E is 1,3,4-thiadiazole, then R$_{11}$ is not aryl or heteroaryl; and with the proviso that the compound is not any of the following:

2-[[5-ethyl-4-[(tetrahydro-2-furanyl)methyl]-4H-1,2,4-triazol-3-yl]thio]-N-[5-(4-methoxyphenyl)-1,3,4-thiadiazol-2-yl]-acetamide;

2-[(5-cyclopentyl-4-methyl-4H-1,2,4-triazol-3-yl)thio]-N-[5-(4-methoxyphenyl)-1,3,4-thiadiazol-2-yl]-acetamide;

N-[5-(4-methoxyphenyl)-1,3,4-thiadiazol-2-yl]-2-[[5-methyl-4-(4-methylphenyl)-4H-1,2,4-triazol-3-yl]thio]-acetamide;

2-[[5-[(4-chlorophenyl)methyl]-4-ethyl-4H-1,2,4-triazol-3-yl]thio]-N-[5-(4-methoxyphenyl)-1,3,4-thiadiazol-2-yl]-acetamide;
2-[(5-cyclopropyl-4-propyl-4H-1,2,4-triazol-3-yl)thio]-N-[5-(4-methoxyphenyl)-1,3,4-thiadiazol-2-yl]-acetamide;
2-[[4-(2,5-dimethylphenyl)-5-methyl-4H-1,2,4-triazol-3-yl]thio]-N-(5-phenyl-1,3,4-thiadiazol-2-yl)-acetamide;
2-[[5-methyl-4-(phenylmethyl)-4H-1,2,4-triazol-3-yl]thio]-N-(5-phenyl-1,3,4-thiadiazol-2-yl)-acetamide;
2-[[4-(4-methoxyphenyl)-5-methyl-4H-1,2,4-triazol-3-yl]thio]-N-(5-phenyl-1,34-thiadiazol-2-yl)-acetamide;
2-[(5-cyclopentyl-4-methyl-4H-1,2,4-triazol-3-yl)thio]-N-(5-phenyl-1,3,4-thiadiazol-2-yl)-acetamide;
2-[[5-[(4-chlorophenyl)methyl]-4-ethyl-4H-1,2,4-triazol-3-yl]thio]-N-(5-phenyl-1,3,4-thiadiazol-2-yl)-acetamide;
2-[(5-cyclopropyl-4-ethyl-4H-1,2,4-triazol-3-yl)thio]-N-(5-phenyl-1,3,4-thiadiazol-2-yl)-acetamide;
2-[(5-cyclopropyl-4-propyl-4H-1,2,4-triazol-3-yl)thio]-N-(5-phenyl-1,3,4-thiadiazol-2-yl)-acetamide;
2-[[5-(2-cyclohexylethyl)-4-methyl-4H-1,2,4-triazol-3-yl]thio]-N-(5-phenyl-1,3,4-thiadiazol-2-yl)-acetamide;
2-[[5-ethyl-4-[(tetrahydro-2-furanyl)methyl]-4H-1,2,4-triazol-3-yl]thio]-N-(5-phenyl-1,3,4-thiadiazol-2-yl)-acetamide;
2-[[4-ethyl-5-(4-morpholinylmethyl)-4H-1,2,4-triazol-3-yl]thio]-N-(5-phenyl-1,3,4-thiadiazol-2-yl)-acetamide;
2-[[4-methyl-5-(phenylmethyl)-4H-1,2,4-triazol-3-yl]thio]-N-(5-phenyl-1,3,4-thiadiazol-2-yl)-acetamide;
2-[[4-methyl-5-(4-morpholinylmethyl)-4H-1,2,4-triazol-3-yl]thio]-N-(5-phenyl-1,3,4-thiadiazol-2-yl)-acetamide;
2-[[5-(4-morpholinylmethyl)-4-phenyl-4H-1,2,4-triazol-3-yl]thio]-N-(5-phenyl-1,3,4-thiadiazol-2-yl)-acetamide; and
2-[[4-ethyl-5-(phenylmethyl)-4H-1,2,4-triazol-3-yl]thio]-N-(5-phenyl-1,3,4-thiadiazol-2-yl)-acetamide.

2. The compound of claim 1, wherein $R^5$, $R^6$, and $R^7$ are H.

3. The compound of claim 1, wherein at least one of $R^5$ and $R^6$ is H or F.

4. The compound of claim 1, wherein $R^7$ is —O—CH$_2$—CH$_2$—F or —S-Me.

5. The compound of claim 1, with the proviso that when Q is S and E is 1,3,4-thiadiazole, then $A^1$ and $A^2$ are not CH, $R^5$ and $R^6$ are not H, and $R^7$ is not H or OMe.

6. The compound of claim 1, selected from the group consisting of:
2-[(5-ethyl-4-phenyl-4H-1,2,4-triazol-3-yl)sulfanyl]-N-[5-(4-methoxyphenyl)-1,3,4-thiadiazol-2-yl]acetamide;
2-[(diethyl-4H-1,2,4-triazol-3-yl)sulfanyl]-N-[5-(4-methoxyphenyl)-1,3,4-thiadiazol-2-yl]acetamide;
2-[(5-benzyl-4-ethyl-4H-1,2,4-triazol-3-yl)sulfanyl]-N-[5-(4-methoxyphenyl)-1,3,4-thiadiazol-2-yl]acetamide;
2-{[4-ethyl-5-(4-fluorophenyl)-4H-1,2,4-triazol-3-yl]oxy}-N-[5-(4-methoxyphenyl)-1,3,4-thiadiazol-2-yl]acetamide;
2-[(4-ethyl-5-methyl-4H-1,2,4-triazol-3-yl)sulfanyl]-N-[5-(4-methanesulfonylphenyl)-1,3,4-thiadiazol-2-yl]acetamide;
2-{[4-ethyl-5-(propan-2-yl)-4H-1,2,4-triazol-3-yl]sulfanyl}-N-[5-(4-methanesulfonylphenyl)-1,3,4-thiadiazol-2-yl]acetamide;
2-[(5-cyclopropyl-4-ethyl-4H-1,2,4-triazol-3-yl)sulfanyl]-N-[5-(4-methanesulfonylphenyl)-1,3,4-thiadiazol-2-yl]acetamide;
2-[(diethyl-4H-1,2,4-triazol-3-yl)sulfanyl]-N-[5-(4-methanesulfonylphenyl)-1,34-thiadiazol-2-yl]acetamide;
2-{[4-ethyl-5-(4-fluorophenyl)-4H-1,2,4-triazol-3-yl]sulfanyl}-N-[6-(4-methoxyphenyl)pyridazin-3-yl]acetamide;
2-[(5-ethyl-4-methyl-4H-1,2,4-triazol-3-yl)sulfanyl]-N-[5-(4-methoxyphenyl)-1,3,4-thiadiazol-2-yl]acetamide;
N-[5-(4-methoxyphenyl)-1,3,4-thiadiazol-2-yl]-2-[(5-methyl-4-phenyl-4H-1,2,4-triazol-3-yl)sulfanyl]acetamide;
2-[(diethyl-4H-1,2,4-triazol-3-yl)sulfanyl]-N-{5-[4-(methylsulfanyl)phenyl]-1,3,4-thiadiazol-2-yl}acetamide;
2-[(diethyl-4H-1,2,4-triazol-3-yl)sulfanyl]-N-{5-[4-(2-methylpropoxy)phenyl]-1,3,4-thiadiazol-2-yl}acetamide;
2-[(diethyl-4H-1,2,4-triazol-3-yl)sulfanyl]-N-[5-(4-ethylphenyl)-1,3,4-thiadiazol-2-yl]acetamide;
2-[(diethyl-4H-1,2,4-triazol-3-yl)sulfanyl]-N-[5-(4-propylphenyl)-1,3,4-thiadiazol-2-yl]acetamide;
2-[(diethyl-4H-1,2,4-triazol-3-yl)sulfanyl]-N-[5-(4-butylphenyl)-1,3,4-thiadiazol-2-yl]acetamide;
2-[(diethyl-4H-1,2,4-triazol-3-yl)sulfanyl]-N-(5-phenyl-1,3,4-thiadiazol-2-yl)acetamide;
2-[(diethyl-4H-1,2,4-triazol-3-yl)sulfanyl]-N-{5[4-(2-methylpropyl)phenyl]-1,3,4-thiadiazol-2-yl}acetamide;
2-[(diethyl-4H-1,2,4-triazol-3-yl)sulfanyl]-N-{5-[4-(propan-2-yl)phenyl]-1,3,4-thiadiazol-2-yl}acetamide;
2-[(diethyl-4H-1,2,4-triazol-3-yl)sulfanyl]-N-{5-(4-hydroxyphenyl)-1,3,4-thiadiazol-2-yl}acetamide;
2-{[4-ethyl-5-(2-methoxyethyl)-4H-1,2,4-triazol-3-yl]sulfanyl}-N-(5-phenyl-1,3,4-thiadiazol-2-yl)acetamide;
2-{[4-ethyl-5-(2-methoxyethyl)-4H-1,2,4-triazol-3-yl]sulfanyl}-N-{5-[4-(propan-2-yloxy)phenyl]-1,3,4-thiadiazol-2-yl}acetamide;
2-{[4-ethyl-5-(2-methoxyethyl)-4H-1,2,4-triazol-3-yl]sulfanyl}-N-{5-(4-(propylphenyl-1,3,4-thiadiazol-2-yl}acetamide;
2-[(diethyl-4H-1,2,4-triazol-3-yl)sulfanyl]-N-[5-(4-ethoxyphenyl)-1,3,4-thiadiazol-2-yl]acetamide;
2-[(diethyl-4H-1,2,4-triazol-3-yl)sulfanyl]-N-{5-[4-(2-fluoroethoxy)phenyl]-1,3,4-thiadiazol-2-yl}acetamide;
N-[5-(4-ethoxyphenyl)-1,3,4-thiadiazol-2-yl]-2-{[4-ethyl-5-(propan-2-yl)-4H-1,2,4-triazol-3-yl]sulfanyl}acetamide;
2-{[4-ethyl-5-(propan-2-yl)-4H-1,2,4-triazol-3-yl]sulfanyl}-N-{5-[4-(2-fluoroethoxy)phenyl]-1,3,4-thiadiazol-2-yl}acetamide;
2-{[4-ethyl-5-(propan-2-yl)-4H-1,2,4-triazol-3-yl]sulfanyl}-N-{5-[4-(propan-2-yloxy)phenyl]-1,3,4-thiadiazol-2-yl}acetamide;
2-[(diethyl-4H-1,2,4-triazol-3-yl)sulfanyl]-N-{5-[4-(2-methoxyethoxy)phenyl]-1,3,4-thiadiazol-2-yl}acetamide;
2-{[4-ethyl-5-(propan-2-yl)-4H-1,2,4-triazol-3-yl]sulfanyl}-N-{5-[4-(2-methoxyethoxy) phenyl]-1,3,4-thiadiazol-2-yl}acetamide;
N-[5-(4-cyanophenyl)-1,3,4-thiadiazol-2-yl]-2-[(4,5-diethyl-4H-1,2,4-triazol-3-yl)sulfanyl]acetamide;

2-[(4,5-diethyl-4H-1,2,4-triazol-3-yl)sulfanyl]-N-[5-(4-(trifluoromethyl)phenyl)-1,3,4-thiadiazol-2-yl]acetamide;
2-[(4,5-diethyl-4H-1,2,4-triazol-3-yl)sulfanyl]-N-[5-(4-isopropoxyphenyl)-1,3,4-thiadiazol-2-yl]acetamide;
N-[5-(4-chlorophenyl)-1,3,4-thiadiazol-2-yl]-2-[(4,5-diethyl-4H-1,2,4-triazol-3-yl)sulfanyl]acetamide;
2-[(4-cyclopropyl-5-ethyl-4H-1,2,4-triazol-3-yl)sulfanyl]-N-[5-(4-methoxyphenyl)-1,3,4-thiadiazol-2-yl]acetamide;
2-[(4-ethyl-5-(3-fluorobenzyl)-4H-1,2,4-triazol-3-yl)sulfanyl]-N-[5-(4-methoxyphenyl)-1,3,4-thiadiazol-2-yl] acetamide;
2-[(5-cyclopropyl-4-ethyl-4H-1,2,4-triazol-3-yl)sulfanyl]-N-[5-(4-hydroxyphenyl)-1,3,4-thiadiazol-2-yl]acetamide;
2-[(4-cyclopropyl-5-ethyl-4H-1,2,4-triazol-3-yl)sulfanyl]-N-[5-(4-(methylsulfonyl)phenyl)-1,3,4-thiadiazol-2-yl]acetamide;
2-[(5-ethyl-4-(3-hydroxypropyl)-4H-1,2,4-triazol-3-yl) sulfanyl]-N-[5-(4-methoxyphenyl)-1,3,4-thiadiazol-2-yl]acetamide;
2-[(5-ethyl-4-methyl-4H-1,2,4-triazol-3-yl)sulfanyl]-N-[5-(4-(methylsulfonyl)phenyl)-1,3,4-thiadiazol-2-yl] acetamide;
2-[(5-ethyl-4-isopropyl-4H-1,2,4-triazol-3-yl)sulfanyl]-N-[5-(4-(methylsulfonyl)phenyl)-1,3,4-thiadiazol-2-yl]acetamide;
2-[(5-cyclopropyl-4-ethyl-4H-1,2,4-triazol-3-yl)sulfanyl]-N-[5-(4-(2-methoxyethoxy)phenyl)-1,3,4-thiadiazol-2-yl]acetamide;
2-[(4-ethyl-5-(2-methoxyethyl)-4H-1,2,4-triazol-3-yl) sulfanyl]-N-[5-(4-methoxyphenyl)-1,3,4-thiadiazol-2-yl]acetamide;
(2-[(5-cyclopentyl-4-ethyl-4H-1,2,4-triazol-3-yl)sulfanyl]-N-[5-(4-methanesulfonylphenyl)-1,3,4-thiadiazol-2-yl]acetamide);
2-[(5-ethyl-4-(2-methoxyethyl)-4H-1,2,4-triazol-3-yl) sulfanyl]-N-[5-(4-methoxyphenyl)-1,3,4-thiadiazol-2-yl]acetamide;
2-{[5-ethyl-4-(3-methoxypropyl)-4H-1,2,4-triazol-3-yl] sulfanyl}-N-[5-(4-methoxyphenyl)-1,3,4-thiadiazol-2-yl]acetamide;
2-{[4-ethyl-5-(morpholin-4-ylmethyl)-4H-1,2,4-triazol-3-yl]sulfanyl}-N-[5-(4-methoxyphenyl)-1,3,4-thiadiazol-2-yl]acetamide; and
2-[(4,5-diethyl-4H-1,2,4-triazol-3-yl)sulfanyl]-N-[5-(pyridin-2-yl)-1,3,4-thiadiazol-2-yl]acetamide.

7. A method of treating a disease selected from the group consisting of diabetes, atherosclerosis, disuse osteoporosis, non-alcoholic fatty liver disease, acute kidney injury, kidney ischemia-reperfusion injury, and an inflammatory disease in a subject in need thereof, comprising administering the compound of claim 1 to the subject.

8. The method of claim 7, wherein the disease is diabetes.

9. The method of claim 7, wherein the disease is an inflammatory disease.

10. A pharmaceutical composition comprising the compound of claim 1 and a pharmaceutically acceptable carrier, excipient or diluent.

11. The pharmaceutical composition of claim 10, wherein the pharmaceutical composition is in tablet or capsule form.

12. The method of claim 7, wherein the administration is oral.

13. The method of claim 9, wherein the inflammatory disease is inflammatory bowel disease, psoriasis, allergic contact dermatitis, or rheumatoid arthritis.

14. The method of claim 7, wherein the compound of claim 1 is in a pharmaceutical composition comprising a pharmaceutically acceptable carrier, excipient or diluent.

15. A compound according to Formula (I), wherein Formula (I) is:

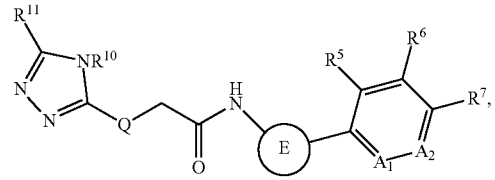

Formula (I)

or a pharmaceutically acceptable salt or stereoisomer thereof, wherein

Q is S, —$CH_2$—, or O;

E is a 5-membered heteroaryl or a 6-membered heteroaryl, wherein E is selected from the group consisting of:

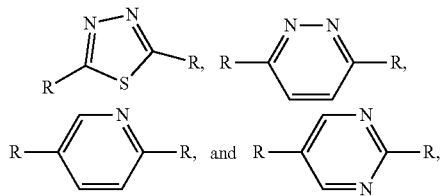

wherein R denotes the attachment points to the rest of the molecule;

$A_1$ and $A_2$ are independently selected from the group consisting of CH, $CR^2$ and N;

$R^2$ is selected from the group consisting of H, F, Cl, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^5$ is selected from the group consisting of H, F, Cl, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^6$ and $R^7$ are bridged to form a 5- or 6-membered ring comprising one or two heteroatoms selected from the group consisting of O, S and N;

m is an integer selected from the group consisting of 1, 2, and 3;

n is an integer selected from the group consisting of 0, 1, and 2;

$R^{4a}$ and $R^{4b}$ are independently selected from the group consisting of H, $C_1$-$C_6$ alkyl, and $C_3$-$C_6$ cycloalkyl;

$R^{10}$ is selected from the group consisting of $C_1$-$C_6$ alkyl, $C_1$-$C_6$ alkylene-aryl, $C_1$-$C_6$ alkylene-$OR^{12a}$, $C_1$-$C_6$ alkylene-$N(R^{12a})(R^{12b})$, $C_1$-$C_6$ alkylene-$C(O)N(R^{12a})$ $(R^{12b})$, $C_1$-$C_6$ alkylene-$C(O)OR^{12a}$, $C_1$-$C_3$ alkylene-$C_3$-$C_6$ cycloalkyl, $C_1$-$C_3$ alkylene-$C_3$-$C_6$ heterocycloalkyl, $C_3$-$C_5$ cycloalkyl, and aryl or heteroaryl, the aryl or heteroaryl optionally substituted with at least one group selected from the group consisting of halogen, $CF_3$, CN, OH, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^{11}$ is selected from the group consisting of $C_1$-$C_6$ alkyl, $C_1$-$C_6$ alkylene-aryl, $C_3$-$C_6$ cycloalkyl, $C_1$-$C_3$ alkylene-$C_3$-$C_6$ heterocycloalkyl, $C_1$-$C_6$ alkylene-$OR^{12a}$, and aryl or heteroaryl, the aryl or heteroaryl optionally substituted with at least one group selected from the group consisting of halogen, $CF_3$, CN, OH, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^{12a}$ and $R^{12b}$ are independently selected from the group consisting of H, $C_1$-$C_4$ alkyl, and cyclopropyl, with the proviso that when Q is S and E is 1,3,4-thiadiazole, then $R_{11}$ is not aryl or heteroaryl.

16. The compound of claim 15, wherein $R^6$ and $R^7$ are bridged to form a 5- or 6-membered ring comprising one or two heteroatoms selected from O.

17. The compound of claim 15, wherein $R^6$ and $R^7$ are bridged to form a 5-membered ring according to —$CH_2$—$CH_2$—O—.

18. The compound of claim 15, wherein $R^5$ is H, $A^1$ and $A^2$ are C, and $R^6$ and $R^7$ are bridged to form a 5-membered ring according to —$CH_2$—$CH_2$—O— to form a 2,3-dihydro-1-benzofuran moiety.

19. The compound of claim 15, wherein $R^6$ and $R^7$ are bridged to form a 6-membered ring according to —O—$CH_2$—$CH_2$—O—.

20. The compound of claim 15, wherein $R^5$ is H, $A^1$ and $A^2$ are C, and $R^6$ and $R^7$ are bridged to form a 6-membered ring according to —O—$CH_2$—$CH_2$—O— to form a 1,4-benzodioxane moiety.

21. The compound of claim 15, wherein the compound is 2-[(diethyl-4H-1,2,4-triazol-3-yl)sulfanyl]-N-[5-(2,3-dihydro-1-benzofuran-5-yl)-1,3,4-thiadiazol-2-yl]acetamide.

22. A method of treating a disease selected from the group consisting of diabetes, atherosclerosis, disuse osteoporosis, non-alcoholic fatty liver disease, acute kidney injury, kidney ischemia-reperfusion injury, and an inflammatory disease in a subject in need thereof, comprising administering the compound of claim 15 to the subject.

23. The method of claim 22, wherein the disease is diabetes.

24. The method of claim 22, wherein the disease is an anti-inflammatory disease.

25. The method of claim 24, wherein the inflammatory disease is inflammatory bowel disease, psoriasis, allergic contact dermatitis, or rheumatoid arthritis.

26. The method of claim 22, wherein the compound of claim 24 is in a pharmaceutical composition comprising a pharmaceutically acceptable carrier, excipient or diluent.

27. The method of claim 22, wherein the administration is oral.

28. A pharmaceutical composition comprising the compound of claim 15 and a pharmaceutically acceptable carrier, excipient or diluent.

29. The pharmaceutical composition of claim 28, wherein the pharmaceutical composition is in tablet or capsule form.

* * * * *